(12) United States Patent
Akishiba et al.

(10) Patent No.: US 10,107,998 B2
(45) Date of Patent: Oct. 23, 2018

(54) OPTICAL-SCANNING-HEIGHT MEASURING DEVICE

(71) Applicant: Keyence Corporation, Osaka (JP)

(72) Inventors: Yuji Akishiba, Osaka (JP); Tatsuro Homma, Osaka (JP)

(73) Assignee: Keyence Corporation, Osaka (JP)

( * ) Notice: Subject to any disclaimer, the term of this patent is extended or adjusted under 35 U.S.C. 154(b) by 0 days.

(21) Appl. No.: 15/808,913

(22) Filed: Nov. 10, 2017

(65) Prior Publication Data

US 2018/0180863 A1 Jun. 28, 2018

(30) Foreign Application Priority Data

Dec. 28, 2016 (JP) .................................. 2016-256612

(51) Int. Cl.
| | | |
|---|---|---|
| *G01B 11/02* | (2006.01) | |
| *G02B 21/00* | (2006.01) | |
| *G01N 21/95* | (2006.01) | |
| *G02B 26/12* | (2006.01) | |
| *G02B 27/00* | (2006.01) | |

(52) U.S. Cl.
CPC ............ *G02B 21/002* (2013.01); *G01N 21/95* (2013.01); *G02B 26/123* (2013.01); *G02B 26/127* (2013.01); *G02B 27/0031* (2013.01)

(58) Field of Classification Search
CPC ................ G02B 21/002; G02B 26/127; G02B 27/0031; G02B 26/123; G01N 21/95; G01B 11/24; G01B 11/02; G01B 9/02; G01B 9/02034
See application file for complete search history.

(56) References Cited

U.S. PATENT DOCUMENTS

| | | | |
|---|---|---|---|
| 6,485,413 B1 * | 11/2002 | Boppart | ............ A61B 1/00096 |
| | | | 356/450 |
| 7,242,485 B2 | 7/2007 | Akishiba | |
| 8,102,537 B2 | 1/2012 | Akishiba | |

(Continued)

FOREIGN PATENT DOCUMENTS

| | | |
|---|---|---|
| JP | 2005-098833 | 4/2005 |
| JP | 2010-043954 | 2/2010 |
| JP | 2012-021856 | 2/2012 |
| JP | 2014-085269 | 5/2014 |

OTHER PUBLICATIONS

U.S. Appl. No. 15/808,911, filed Nov. 10, 2017 (173 pages).

(Continued)

*Primary Examiner* — Mohamed K Amara
(74) *Attorney, Agent, or Firm* — Kilyk & Bowersox, P.L.L.C.

(57) ABSTRACT

To provide an optical-scanning-height measuring device capable of quickly and highly accurately measuring the height of the surface of a measurement object while being compactly configured. In order to obtain interference light appropriate for calculation of height, an optical path length of the reference light is adjusted in the reference section 250. Movable sections 252a and 252b supported by a supporting section 251 move on linearly extending two linear guides 251g, whereby the optical path length of the reference light changes. When the optical path length of the reference light is adjusted, the movable sections 252a and 252b are moved in opposite directions each other.

7 Claims, 31 Drawing Sheets

(56) References Cited

U.S. PATENT DOCUMENTS

| | | | | |
|---|---|---|---|---|
| 2003/0090677 A1* | 5/2003 | Evans | ................ | G01B 11/2441 |
| | | | | 356/512 |
| 2005/0219496 A1* | 10/2005 | Oshida | ................ | G02B 26/123 |
| | | | | 355/67 |
| 2006/0082781 A1* | 4/2006 | Chan | ................ | G01B 11/2441 |
| | | | | 356/495 |
| 2007/0097367 A1* | 5/2007 | Sakamoto | ........... | G03F 7/70341 |
| | | | | 356/400 |
| 2011/0102761 A1* | 5/2011 | Yoshimoto | .......... | G03F 7/70725 |
| | | | | 355/72 |
| 2013/0218008 A1* | 8/2013 | Itsuji | .................... | A61B 5/0073 |
| | | | | 600/425 |
| 2014/0253914 A1* | 9/2014 | Miyamoto | ........... | G01B 11/002 |
| | | | | 356/244 |
| 2015/0165550 A1* | 6/2015 | Fry | ...................... | B23K 26/032 |
| | | | | 219/121.68 |
| 2016/0039045 A1* | 2/2016 | Webster | ............... | B23K 26/032 |
| | | | | 356/496 |
| 2016/0131474 A1* | 5/2016 | Saeki | .................. | G01B 9/0205 |
| | | | | 356/511 |
| 2018/0011031 A1* | 1/2018 | Maznev | ............... | G10K 11/002 |

OTHER PUBLICATIONS

U.S. Appl. No. 15/808,914, filed Nov. 10, 2017 (182 pages).
U.S. Appl. No. 15/808,915, filed Nov. 10, 2017 (171 pages).
U.S. Appl. No. 15/696,199, filed Sep. 6, 2017 (86 pages).

* cited by examiner

FIG. 9A  SETTING MODE
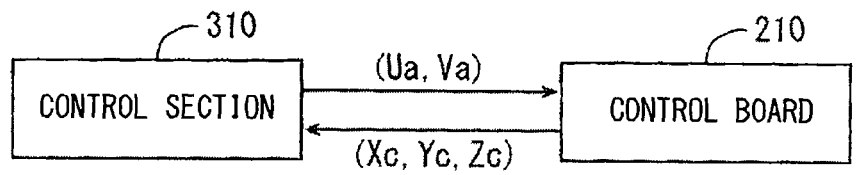
FIG. 9B  MEASUREMENT MODE
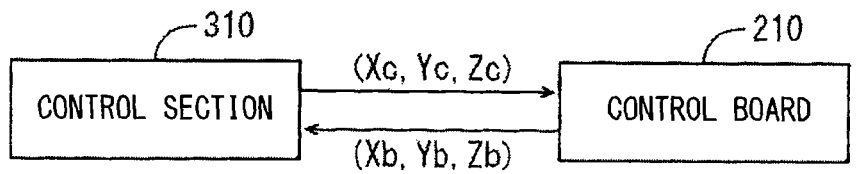
FIG. 9C  HEIGHT GAUGE MODE
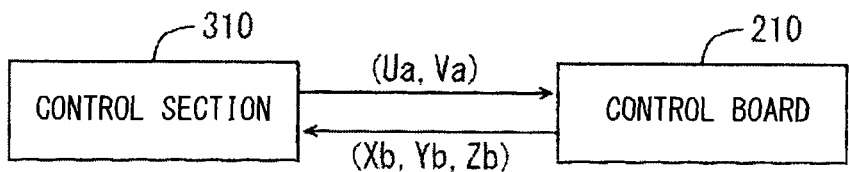

OPTICAL-SCANNING-HEIGHT MEASURING DEVICE

CROSS-REFERENCE TO RELATED APPLICATIONS

The present application claims foreign priority based on Japanese Patent Application No. 2016-256612, filed Dec. 28, 2016, the contents of which is incorporated herein by reference.

BACKGROUND OF THE INVENTION

1. Field of the Invention

The present invention relates to an optical-scanning-height measuring device that measures a surface shape of a measurement object.

2. Description of Related Art

An optical-scanning-height measuring device is used to measure a surface shape of a measurement object For example, in a dimension measuring device described in JP-A-2014-85269, light irradiated from a low-coherence light source is split into measurement light and reference light by a beam splitter. The measurement light is deflected by a measurement-object scanning optical system and irradiated on the surface of a measurement object. The reference light is guided by a reference-light scanning optical system and reflected by a corner cube prism while an optical path length in the reference-light scanning optical system being changed. A surface position of a measurement point of the measurement object is calculated on the basis of interference of the measurement light reflected by the measurement object and the reference light reflected by the corner cube prism.

SUMMARY OF THE INVENTION

In the reference-light scanning optical system explained above, in order to change an optical path length of the reference light in the reference-light scanning optical system, a linear motion stage reciprocatingly moves on a linear guide rail together with the corner cube prism.

In order to quickly measure a surface shape of the measurement object, it is necessary to increase moving speed of the linear motion stage. In this case, vibration of the entire dimension measuring device increases. In order to prevent such vibration, it is necessary to increase a shape measuring device in size and weight. Therefore, it is difficult to quickly measure the height of the surface of the measurement object while compactly configuring the shape measuring device.

An object of the present invention is to provide an optical-scanning-height measuring device capable of quickly and highly accurately measuring the height of the surface of a measurement object while being compactly configured.

(1) An optical-scanning-height measuring device according to the present invention includes: a position-information acquiring section configured to receive designation of a measurement point; a light emitting section configured to emit temporally low-coherent light; a dividing section configured to divide the light emitted from the light emitting section and output a part of the divided light as measurement light and output another part of the divided light as reference light; a deflecting section configured to deflect the measurement light output from the dividing section and irradiate the measurement light on a measurement object; a driving control section configured to control the deflecting section to irradiate light on a portion of the measurement object corresponding to the measurement point received by the position-information acquiring section; a detecting section configured to detect a deflecting direction of the deflecting section or an irradiation position of the measurement light deflected by the deflecting section; a reference body configured to reflect the reference light output from the dividing section to return to the dividing section; a movable section configured to move along a first movement axis to thereby change an optical path of the reference light leading from the dividing section to the reference body; a supporting section configured to movably support the movable section on the first movement axis; a movable-section-position detecting section configured to detect a relative position of the movable section with respect to the supporting section; an interference-light generating section configured to generate interference light of the measurement light irradiated on the measurement object by the deflecting section to return to the dividing section from the measurement object and the reference light reflected by the reference body to return to the dividing section; a light receiving section configured to receive the generated interference light and generate a light reception signal indicating a received light amount of the interference light; a distance-information calculating section configured to calculate a distance between the dividing section and the measurement object on the basis of the position of the movable section detected by the movable-section-position detecting section and the received light amount of the interference light in the light reception signal output by the light receiving section; a calculating section configured to calculate height of a portion of the measurement object corresponding to the designated measurement point on the basis of the deflecting direction of the deflecting section and the irradiation position of the measurement light deflected by the deflecting section detected by the detecting section and the distance calculated by the distance-information calculating section; a balancing section movably supported on a second movement axis extending substantially in parallel to the first movement axis with respect to the supporting section; and a reference driving section configured to move the movable section and the balancing section with respect to the supporting section in opposite directions each other during the movement of the movable section.

In the optical-scanning-height measuring device, the designation of the measurement point is received by the position-information acquiring section. The low-coherent light emitted from the light emitting section is divided into the measurement light and the reference light by the dividing section. The measurement light output from the dividing section is irradiated on the portion of the measurement object corresponding to the designated measurement point. At this point, the deflecting direction of the measurement light deflected by the deflecting section or the irradiation position of the measurement light deflected by the deflecting direction is detected by the detecting section. On the other hand, the reference light output from the dividing section is reflected by the reference body and returns to the dividing section. The movable section supported by the supporting section moves along the first movement axis, whereby the optical path length of the reference light leading from the dividing section to the reference body changes. At this point, the relative position of the movable section with respect to the supporting section is detected.

The interference light of the measurement light returning from the measurement object to the dividing section and the reference light returning from the reference body to the dividing section is generated. The generated interference light is received by the light receiving section and the light reception signal is generated. The light reception signal output from the light receiving section indicates the received light amount of the interference light. The distance between the dividing section and the measurement object is calculated by the distance-information calculating section on the basis of the received light amount of the interference light and the position of the movable section detected when the received light amount is acquired. The height of the portion of the measurement object corresponding to the designated measurement point is calculated by the height calculating section on the basis of the deflecting direction of the defecting section or the irradiation position of the measurement light deflected by the deflecting section detected by the detecting section and the distance calculated by the distance-information calculating section.

With the configuration explained above, the movable section and the balancing section are moved with respect to the supporting section in the opposite directions each other by the reference driving section during the movement of the movable section. In this case, even if the movable section intermittently repeats movement and stop, the position of the center of gravity of the optical-scanning-height measuring device hardly changes. Therefore, the optical-scanning-height measuring device does not unstably vibrate. It is unnecessary to increase the optical-scanning-height measuring device in size and weight. It is possible to move the movable section at high speed. As a result, it is possible to quickly and highly accurately measure the height of the surface of the measurement object while compactly configuring the optical-scanning-height measuring device.

(2) The optical-scanning-height measuring device may further include one or a plurality of reflecting members configured to reflect the reference light output from the dividing section to guide the reference light to the reference body and reflect the reference light reflected by the reference body to return the reference light to the dividing section. A part of the reference body and the one or plurality of reflecting members may be attached to the movable section.

In this case, since the reference light is reflected by the one or plurality of reflecting members between the dividing section and the reference body, by appropriately disposing the one or plurality of reflecting members, it is possible to compactly configure the optical-scanning-height measuring device while securing a large optical path length of the reference light. Since a part of the reference body and the one or plurality of reflecting members are attached to the movable section, it is possible to easily change the optical path length of the reference light between the dividing section and the reference body according to the movement of the movable section.

(3) At least a remaining part of the reference body and the one or plurality of reflecting members may be attached to the balancing section. The movable-section-position detecting section may further detect a relative position of the balancing section with respect to the supporting section. The distance-information calculating section may calculate a distance between the deflecting section and the measurement object on the basis of the position of the movable section and the position of the balancing section detected by the movable-section-position detecting section and the light reception signal output by the light receiving section.

With the configuration explained above, the movable section and the balancing section move close to or away from each other in a direction along the first and second movement axes during the movement of the movable section. Consequently, when the movable section and the balancing section move close to each other, a part of the reference body and the one or plurality of reflecting members and at least the remaining part of the reference body and the one or plurality of reflecting members move close to each other. Consequently, it is possible to sufficiently reduce the optical path length of the reference light. When the movable section and the balancing section move away from each other, a part of the reference body and the one or plurality of reflecting members and at least the remaining part of the reference body and the one or plurality of reflecting members move away from each other. Consequently, it is possible to sufficiently increase the optical path length of the reference light.

As a result, an adjustable range of the optical path length of the reference light is expanded. It is possible to more quickly change the optical path length of the reference light.

(4) A total of weight of a part of the reference body and the one or plurality of reflecting members and weight of the movable section may be set to be in a fixed range from a total of weight of at least the remaining part of the reference body and the one or plurality of reflecting members and weight of the balancing section. Consequently, the position of the center of gravity of the optical-scanning-height measuring device during the movement of the movable section is more stabilized.

(5) The reference body may be a corner cube reflector.

The corner cube reflector reflects light in an original direction irrespective of an incident direction. With the configuration explained above, since the corner cube reflector is used as the reference body, it is possible to accurately and easily set an optical path of the reference light between the dividing section and the reference body.

(6) The distance-information calculating section may calculate a difference between an optical path length of the measurement light irradiated on the measurement object by the deflecting section and returning from the measurement object to the dividing section and an optical path length of the reference light reflected by the reference body to return to the dividing section and calculate a distance between the deflecting section and the measurement object on the basis of a result of the calculation. The driving control section may control the reference driving section such that an optical path length of the reference light leading from the dividing section to the reference body is maintained when the difference calculated by the distance-information calculating section is equal to or smaller than a threshold decided in advance and control the reference driving section such that the optical path length of the reference light leading from the dividing section to the reference body changes when the difference calculated by the distance-information calculating section is larger than the threshold decided in advance.

In this case, a difference between an optical path length of the measurement light output from the dividing section and returning to the dividing section and an optical path length of the reference light output from the dividing section and returning to the dividing section is calculated on the basis of the light reception signal output by the light receiving section. When the calculated difference is equal to or smaller than the threshold, the optical path length of the reference light leading from the dividing section to the reference body is maintained. When the calculated difference is larger than the threshold, the optical path length of the reference light leading from the dividing section to the reference body is changed. In this way, the movable section is moved according to the calculated difference. Consequently, it is possible to easily adjust the optical path length of the reference light to an appropriate size. As a result, a measurable range by the optical-scanning-height measuring device is expanded.

(7) The optical-scanning-height measuring device may further include a focusing section. The focusing section may include: a lens disposed on an optical path of the measurement light from the dividing section to the deflecting section; a lens moving section configured to move the lens on the optical path of the measurement light to thereby adjust a position of a focus of the measurement light irradiated on the measurement object; and a lens control section configured to control the lens moving section on the basis of the distance calculated by the distance-information calculating section to focus the measurement light on a surface of the measurement object.

In this case, since the measurement light is focused on the surface of the measurement object, measurement accuracy of the optical-scanning-height measuring device is improved.

According to the present invention, it is possible to quickly and highly accurately measure the height of the surface of the measurement object while compactly configuring the optical-scanning-height measuring device.

BRIEF DESCRIPTION OF THE DRAWINGS

FIGS. 9A to 9C are diagrams showing contents of data transmitted between a control section and a control board in operation modes.

DESCRIPTION OF EMBODIMENTS

(1) Overall Configuration of an Optical-Scanning-Height Measuring Device

Figure 1:
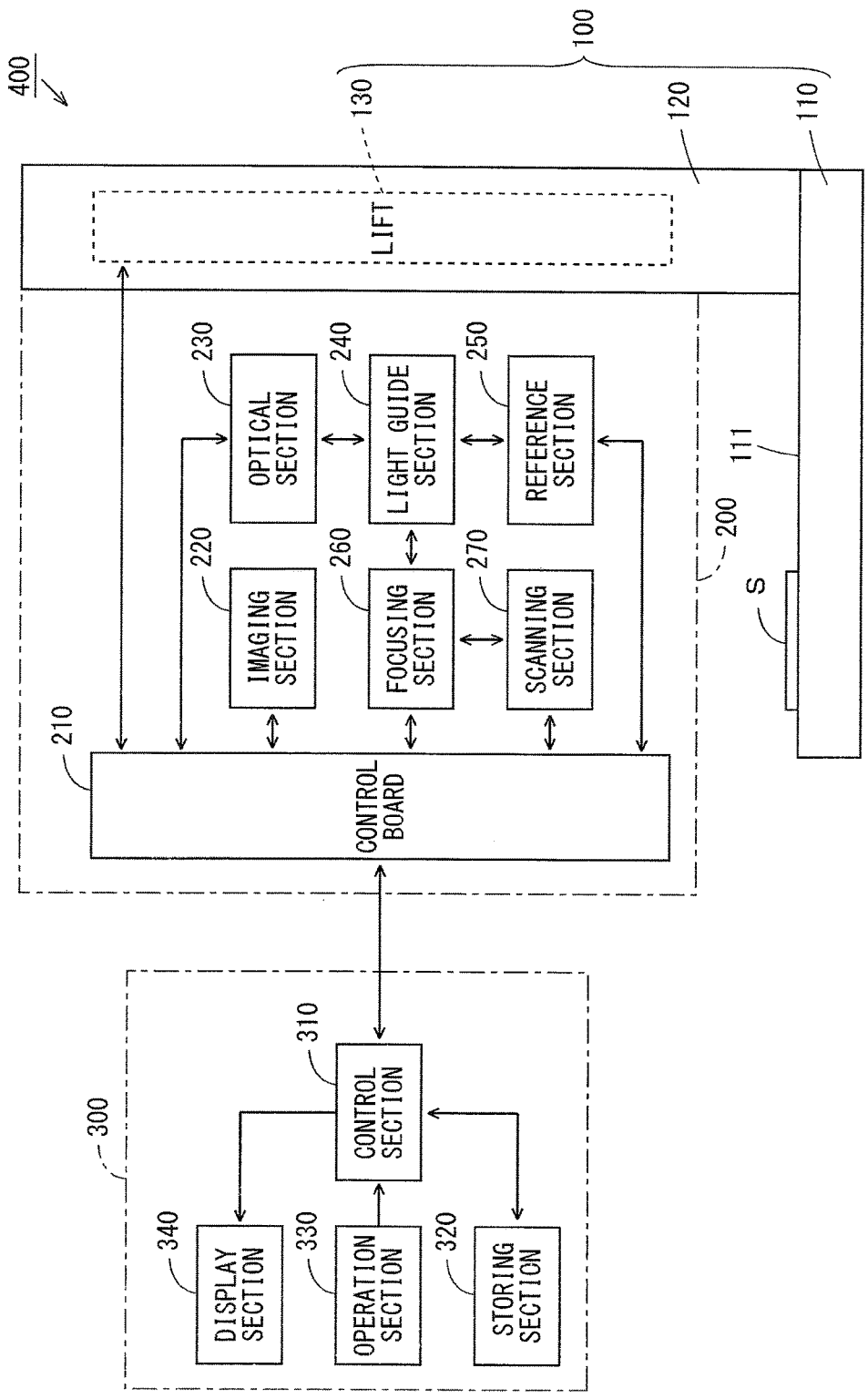
FIG. 1 is a block diagram showing an overall configuration of an optical-scanning-height measuring device according to an embodiment of the present invention.
Figure 2:
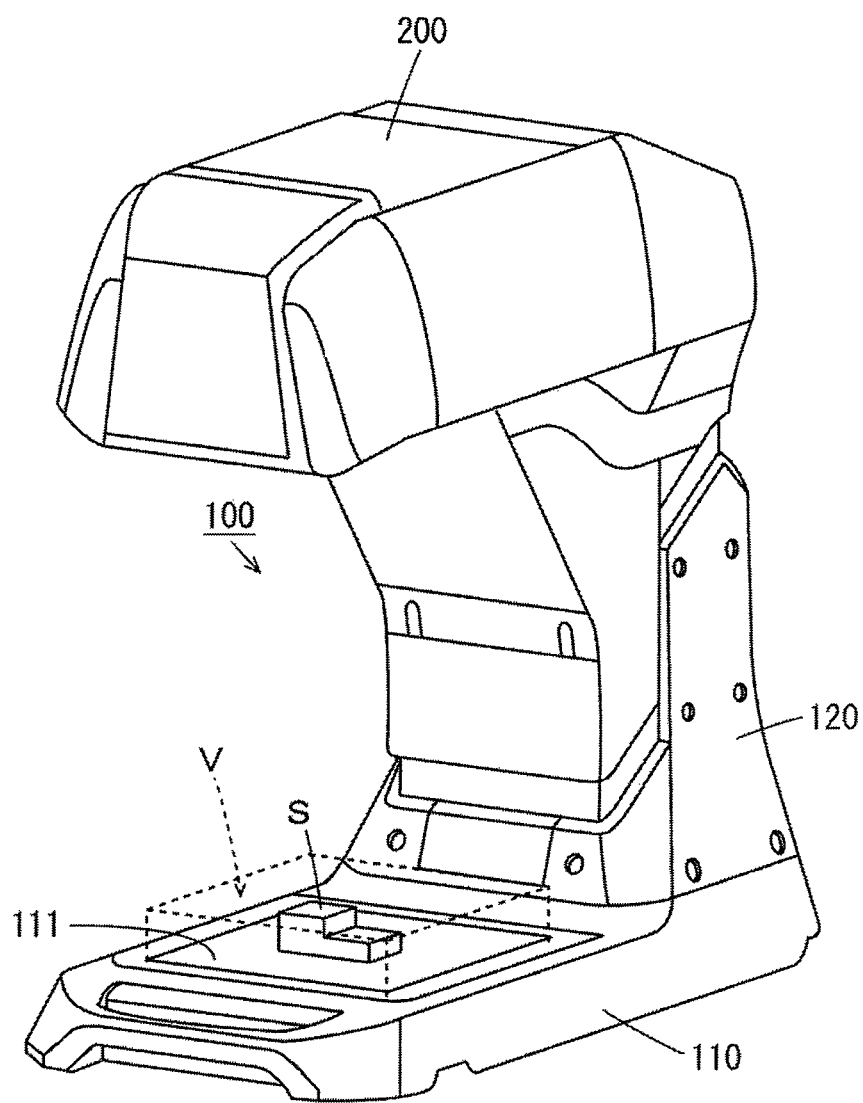
FIG. 2 is an exterior perspective view showing a stand section shown in FIG. 1.

An optical-scanning-height measuring device according to an embodiment of the present invention is explained below with reference to the drawings. FIG. 1 is a block diagram showing an overall configuration of the optical-scanning-height measuring device according to the embodiment of the present invention. FIG. 2 is an exterior perspective view showing a stand section 100 shown in FIG. 1. As shown in FIG. 1, an optical-scanning-height measuring device 400 includes the stand section 100, a measurement head 200, and a processing device 300.

The stand section 100 has an L shape in longitudinal cross section and includes a setting section 110, a holding section 120, and a lift 130. The setting section 110 has a horizontal flat shape and is set on a setting surface. As shown in FIG. 2, a square optical surface plate 111 on which a measurement object S (FIG. 1) is placed is provided on the upper surface of the setting section 110. A measurement region V where the measurement object S can be measured by the measurement head 200 is defined above the optical surface plate 111. In FIG. 2, the measurement region V is indicated by a dotted line.

In the optical surface plate 111, a plurality of screw holes are formed to be arranged at equal intervals in two directions orthogonal to each other. Consequently, it is possible to fix the measurement object S to the optical surface plate 111 using a clamp member and a screw member in a state in which the surface of the measurement object S is located in the measurement region V.

The holding section 120 is provided to extend upward from one end portion of the setting section 110. The measurement head 200 is attached to the upper end portion of the holding section 120 to be opposed to the upper surface of the optical surface plate 111. In this case, since the measurement head 200 and the setting section 110 are held by the holding section 120, it is easy to handle the optical-scanning-height measuring device 400. Since the measurement object S is placed on the optical surface plate 111 on the setting section 110, it is possible to easily locate the measurement object S in the measurement region V.

As shown in FIG. 1, the lift 130 is provided on the inside of the holding section 120. The lift 130 can move the measurement head 200 in the up-down direction (the height direction of the measurement object S) with respect to the measurement object S on the optical surface plate 111. The measurement head 200 includes a control board 210, an imaging section 220, an optical section 230, a light guide section 240, a reference section 250, a focusing section 260, and a scanning section 270. The control board 210 includes, for example, a CPU (central processing unit), a ROM (read only memory), and a RAM (random access memory). The control board 210 may be configured by a microcomputer.

The control board 210 is connected to the processing device 300. The control board 210 controls the operations of the lift 130, the imaging section 220, the optical section 230, the reference section 250, the focusing section 260, and the scanning section 270 on the basis of a command by the processing section 300. The control board 210 gives various kinds of information acquired from the imaging section 220, the optical section 230, the reference section 250, the focusing section 260, and the scanning section 270 to the processing device 300. The imaging section 220 generates image data of the measurement object S by imaging the measurement object S placed on the optical surface plate 111 and gives the generated image data to the control board 210.

The optical section 230 emits emission light having temporally low coherency to the light guide section 240. The light guide section 240 divides the emission light from the optical section 230 into reference light and measurement light, guides the reference light to the reference section 250, and guides the measurement light to the focusing section 260. The reference section 250 reflects the reference light to the light guide section 240. The focusing section 260 focuses the measurement light that passes through the focusing section 260. The scanning section 270 scans the measurement light focused by the focusing section 260 to thereby irradiate the measurement light on a desired portion of the measurement object S.

A part of the measurement light irradiated on the measurement object S is reflected by the measurement object S and guided to the light guide section 240 through the scanning section 270 and the focusing section 260. The light guide section 240 generates interference light of the reference light reflected by the reference section 250 and the measurement light reflected by the measurement object S and guides the interference light to the optical section 230. The optical section 230 detects a received light amount for each of wavelengths of the interference light and gives a signal indicating a result of the detection to the control board 210. Details of the measurement head 200 are explained below.

The processing device 300 includes a control section 310, a storing section 320, an operation section 330, and a display section 340. The control section 310 includes, for example, a CPU. The storing section 320 includes, for example, a ROM, a RAM, and a HDD (hard disk drive). A system program is stored in the storing section 320. The storing section 320 is used for storage of various data and processing of the data.

The control section 310 gives, on the basis of the system program stored in the storing section 320, a command for controlling the operations of the imaging section 220, the optical section 230, the reference section 250, the focusing section 260, and the scanning section 270 of the measurement head 200 to the control board 210. The control section 310 acquires various kinds of information from the control board 210 of the measurement head 200 and causes the storing section 320 to store the various kinds of information.

The operation section 330 includes a pointing device such as a mouse, a touch panel, a trackball, or a joystick and a keyboard. The operation section 330 is operated by a user in order to give an instruction to the control section 310. The display section 340 includes, for example, an LCD (liquid crystal display) panel or an organic EL (electroluminescence) panel. The display section 340 displays an image based on image data stored in the storing section 320, a measurement result, and the like.

(2) The Lift and the Light Guide Section

Figure 3:
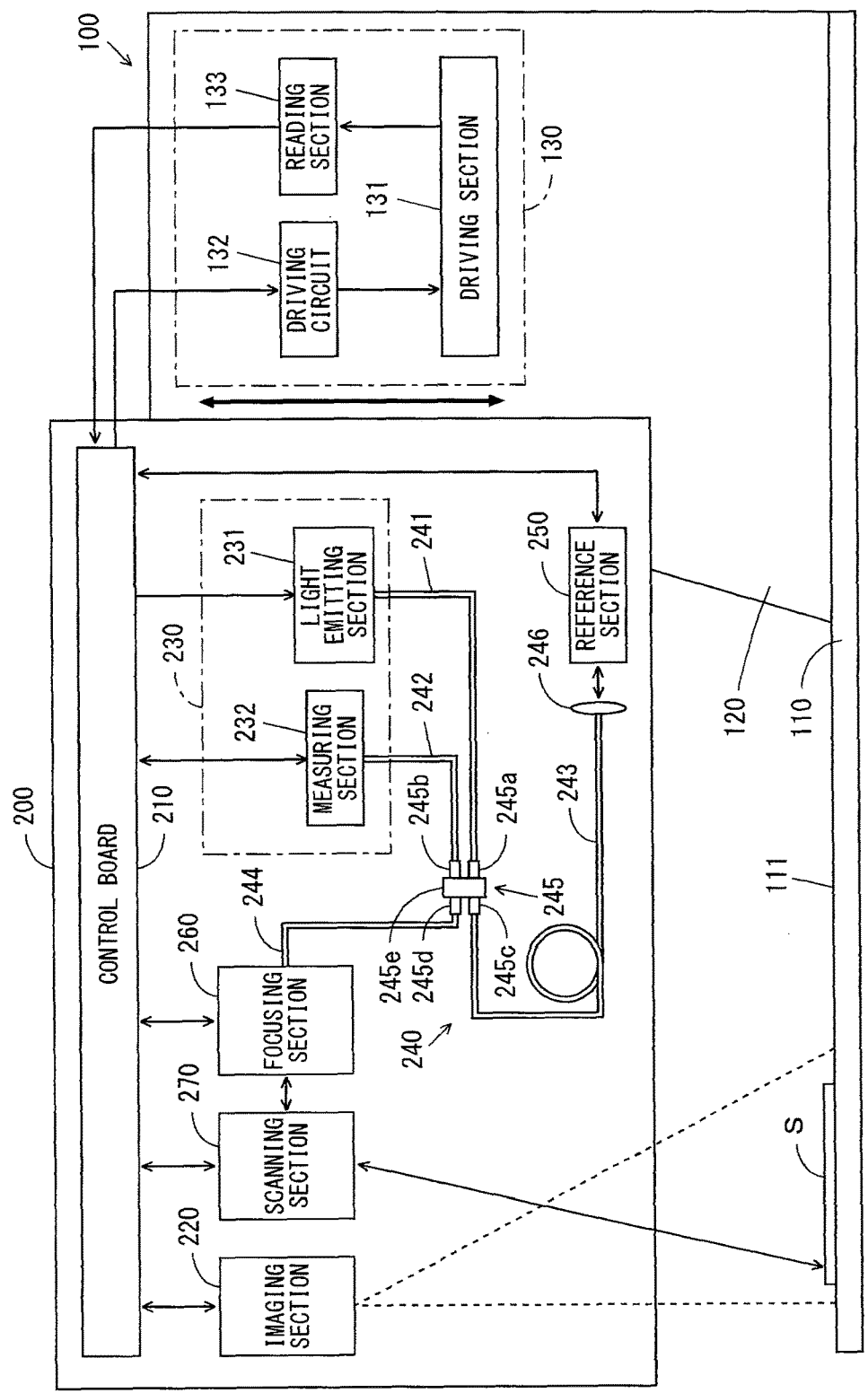
FIG. 3 is a block diagram showing the configurations of the stand section and a measurement head.

FIG. 3 is a block diagram showing the configurations of the stand section 100 and the measurement head 200. In FIG. 3, detailed configurations of the lift 130, the optical section 230, and the light guide section 240 are shown. As shown in FIG. 3, the lift 130 includes a driving section 131, a driving circuit 132, and a reading section 133.

The driving section 131 is, for example, a motor. As indicated by a thick arrow in FIG. 3, the driving section 131 moves the measurement head 200 in the up-down direction with respect to the measurement object S on the optical surface plate 111. Consequently, it is possible to adjust an optical path length of measurement light over a wide range. The optical path length of the measurement light is the length of an optical path from the time when the measurement light is output from a port 245d of the light guide section 240 explained below until the measurement light reflected by the measurement object S is input to the port 245d.

The driving circuit 132 is connected to the control board 210. The driving circuit 132 drives the driving section 131 on the basis of the control by the control board 210. The reading section 133 is, for example, an optical linear encoder. The reading section 133 reads a driving amount of the driving section 131 to thereby detect a position in the up-down direction of the measurement head 200. The reading section 133 gives a result of the detection to the control board 210.

The optical section 230 includes a light emitting section 231 and a measuring section 232. The light emitting section 231 includes, for example, an SLD (super luminescent diode) as a light source and emits emission light having relatively low coherency. Specifically, the coherency of the emission light is higher than the coherency of light or white light emitted by an LED (light emitting diode) and lower than the coherency of laser light. Therefore, the emission light has a wavelength band width smaller than the wavelength band width of the light or the white light emitted by the LED and larger than the wavelength band width of the laser light. The emission light from the optical section 230 is input to the light guide section 240.

Figure 4:
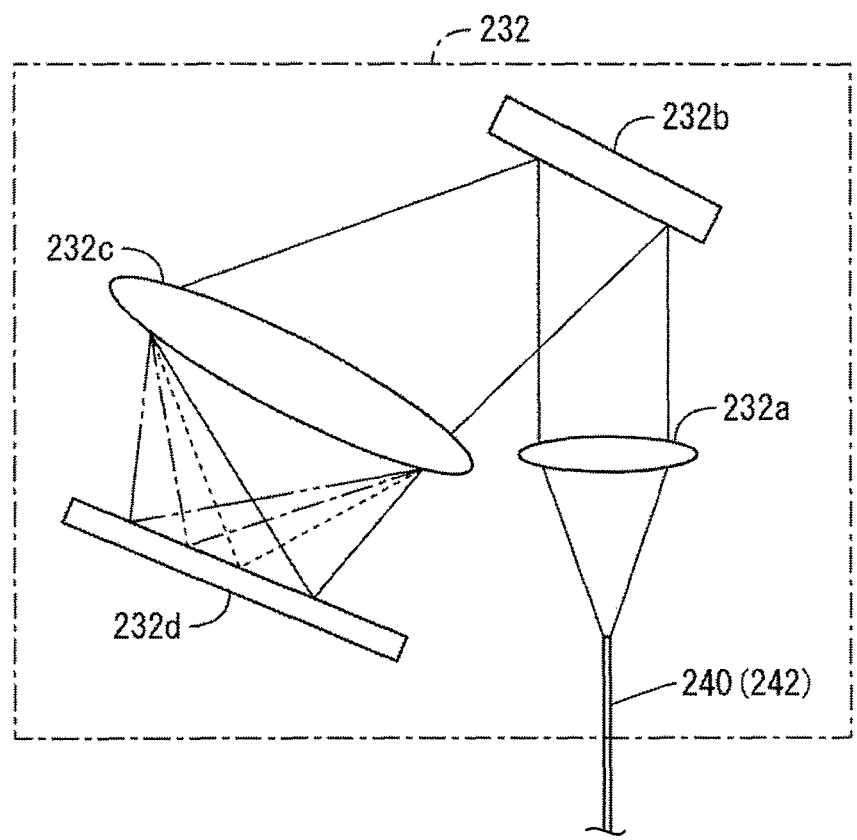
FIG. 4 is a schematic diagram showing the configuration of a measuring section.

Interference light from the light guide section 240 is output to the measuring section 232. FIG. 4 is a schematic diagram showing the configuration of the measuring section 232. As shown in FIG. 4, the measuring section 232 includes lenses 232a and 232c, a spectral section 232b, and a light receiving section 232d. Interference light output from an optical fiber 242 of the light guide section 240 explained below passes through the lens 232a to thereby be substantially collimated and made incident on the spectral section 232b. The spectral section 232b is, for example, a reflective diffraction grating. Light made incident on the spectral section 232b is spectrally dispersed to reflect at angles different for each of wavelengths and passes through the lens 232c to thereby be focused on one-dimensional positions different for each of the wavelengths.

The light receiving section 232d includes, for example, an imaging element (a one-dimensional line sensor) in which a plurality of pixels are one-dimensionally arrayed. The imaging element may be a multi-division PD (photodiode), a CCD (charge coupled device) camera, or a CMOS (complementary metal oxide semiconductor) image sensor or may be other elements. The light receiving section 232d is disposed such that a plurality of pixels of the imaging element respectively receive lights in a different focusing positions different for each of wavelengths formed by the lens 232c.

Analog electric signals corresponding to received light amounts (hereinafter referred to as light reception signals) are output from the pixels of the light receiving section 232d and given to the control board 210 shown in FIG. 3. Consequently, the control board 210 acquires data indicating a relation between the pixels of the light receiving section 232d (the wavelength of interference light) and the received light amount. The control board 210 performs a predetermined arithmetic operation and predetermined processing on the data to thereby calculate height of a portion of the measurement object S.

As shown in FIG. 3, the light guide section 240 includes four optical fibers 241, 242, 243, and 244, a fiber coupler 245, and a lens 246. The fiber coupler 245 has a so-called 2×2 configuration and includes four ports 245a, 245b, 245c, and 245d and a main body section 245e. The ports 245a and 245b and the ports 245c and 245d are provided in the main body section 245e to be opposed to each other across the main body section 245e.

The optical fiber 241 is connected between the light emitting section 231 and the port 245a. The optical fiber 242 is connected between the measuring section 232 and the port 245b. The optical fiber 243 is connected between the reference section 250 and the port 245c. The optical fiber 244 is connected between the focusing section 260 and the port 245d. Note that, in this embodiment, the optical fiber 243 is longer than the optical fibers 241, 242, and 244. The lens 246 is disposed on an optical path of the optical fiber 243 and the reference section 250.

The emission light from the light emitting section 231 is divided by the light guide section 240 and output as measurement light and reference light. Specifically, the emission light from the light emitting section 231 is input to the port 245a through the optical fiber 241. A part of the emission light input to the port 245a is output from the port 245c as reference light. The reference light passes through the optical fiber 243 and the lens 246 to thereby be substantially collimated and guided to the reference section 250. The reference light reflected by the reference section 250 is input to the port 245c through the lens 246 and the optical fiber 243.

Another part of the emission light input to the port 245a is output from the port 245d as measurement light. The measurement light is irradiated on the measurement object S through the optical fiber 244, the focusing section 260, and the scanning section 270. A part of the measurement light reflected by the measurement object S is input to the port 245d through the scanning section 270, the focusing section 260, and the optical fiber 244.

Interference light is generated by the reference light returning from the reference section 250 and input to the port 245c and the measurement light returning from the measurement object S and input to the port 245d. The generated interference light is output from the port 245b and guided to the measuring section 232 through the optical fiber 242.

(3) The Reference Section

Figure 5:
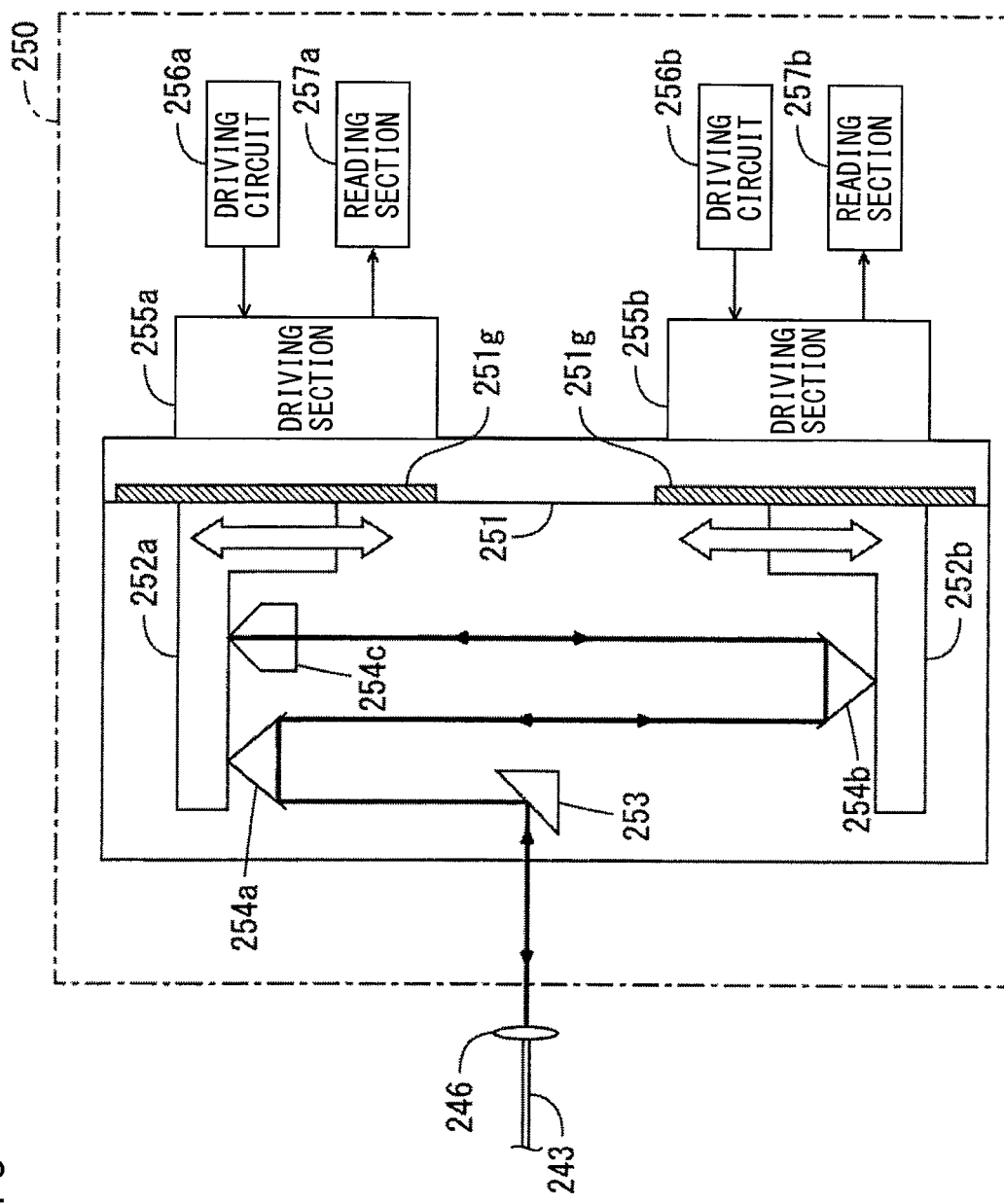
FIG. 5 is a schematic diagram showing the configuration of a reference section.

FIG. 5 is a schematic diagram showing the configuration of the reference section 250. As shown in FIG. 5, the reference section 250 includes a supporting section 251, movable sections 252a and 252b, reflecting members 253, 254a, 254b, and 254c, driving sections 255a and 255b, driving circuits 256a and 256b, and reading sections 257a and 257b.

The supporting section 251 is fixed to a main body of the measurement head 200. Linearly extending two linear guides 251g are attached to the supporting section 251. The two linear guides 251g are fixed to the supporting section 251 such that both of the linear guides 251g extend in one direction and are arranged side by side in one direction. More specifically, the two linear guides 251g are fixed to the supporting section 251 such that the two linear guides 251g are parallel to each other and one linear guide 251g is located on an extended line of the other linear guide 251g. The movable section 252a and 252b are respectively attached to the two linear guides 251g and supported by the supporting section 251 to be capable of moving on the linear guides 251g corresponding to the movable sections 252a and 252b along a direction in which the linear guides 251g extend.

The reflecting member 253 is attached to the supporting section 251 and fixed. The reflecting members 254a and 254c are attached to the movable section 252a. The reflecting member 254b is attached to the movable section 252b. The reflecting member 254c is used as a reference body. In this embodiment, the reflecting member 254c is configured by a corner cube reflector. The corner cube reflector reflects light in an original direction irrespective of an incident direction. Therefore, it is possible to accurately and easily set an optical path of the reference light in the reference section 250. Note that the reflecting member 254c is not limited to the corner cube reflector. A reflection prism or the like may be used.

The reference light output from the optical fiber 243 is substantially collimated by passing through the lens 246 and thereafter sequentially reflected by the reflecting member 253, the reflecting member 254a, the reflecting member 254b, and the reflecting member 254c. The reference light reflected by the reflecting member 254c is sequentially reflected by the reflecting member 254b, the reflecting member 254a, and the reflecting member 253 and input to the optical fiber 243 through the lens 246.

The driving sections 255a and 255b are, for example, voice coil motors. As indicated by white arrows in FIG. 5, the driving sections 255a and 255b move the movable sections 252a and 252b with respect to the supporting section 251 along the direction in which the linear guides 251g extend. In this case, in a direction parallel to the moving direction of the movable sections 252a and 252b, the distance between the reflecting member 253 and the reflecting member 254a, the distance between the reflecting member 254a and the reflecting member 254b, and the distance between the reflecting member 254b and the reflecting member 254c change. Consequently, it is possible to adjust an optical path length of the reference light. Note that the driving sections 255a and 255b may be configured by other driving mechanisms such as stepping motors or piezoelectric motors instead of the voice coil motors.

The optical path length of the reference light is the length of an optical path from the time when the reference light is output from the port 245c shown in FIG. 3 until the reference light reflected by the reflecting member 254c is input to the port 245d. When a difference between the optical path length of the reference light and the optical path length of the measurement light is equal to or smaller than a fixed value, interference light of the reference light and the measurement light is output from the port 245b shown in FIG. 3.

The driving circuits 256a and 256b are connected to the control board 210 shown in FIG. 3. The driving circuits 256a and 256b respectively operate the driving sections 255a and 255b on the basis of the control by the control board 210. At this point, the driving circuits 256a and 256b move the movable sections 252a and 252b with respect to the supporting section 251 in opposite directions each other. In this case, even if the movable sections 252a and 252b intermittently repeat movement and stop, the position of the center of gravity of the optical-scanning-height measuring device 400 hardly changes. Consequently, the position of the center of gravity of the optical-scanning-height measuring device 400 is stabilized during the movement of the movable sections 252a and 252b.

The reading sections 257a and 257b are, for example, optical linear encoders. The reading section 257a reads a driving amount of the driving section 255a to thereby detect a relative position of the movable section 252a with respect to the supporting section 251 and gives a result of the detection to the control board 210. The reading section 257b reads a driving amount of the driving section 255b to thereby detect a relative position of the movable section 252b with respect to the supporting section 251 and gives a result of the detection to the control board 210.

In the reference section 250 explained above, a total of the weight of one movable section 252a and the weight of the reflecting members 254a and 254c attached to the movable section 252a is desirably set to be in a fixed range from a total of the weight of the other movable section 252b and the weight of the reflecting member 254b attached to the movable section 252b. The fixed range is a range in which two total values can be regarded as equal or substantially equal. In this case, the position of the center of gravity of the optical-scanning-height measuring device 400 is further stabilized during the movement of the movable sections 252a and 252b.

(4) The Focusing Section

Figure 6:
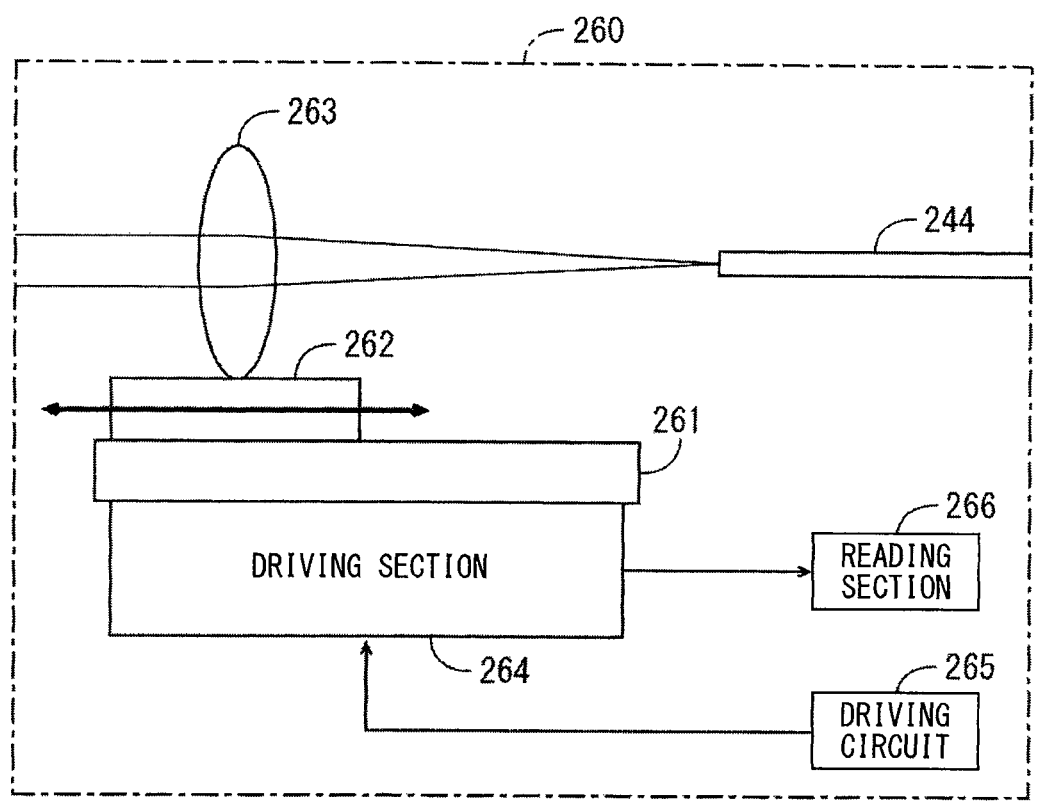
FIG. 6 is a schematic diagram showing the configuration of a focusing section.

FIG. 6 is a schematic diagram showing the configuration of the focusing section 260. As shown in FIG. 6, the focusing section 260 includes a fixed section 261, a movable section 262, a movable lens 263, a driving section 264, a driving circuit 265, and a reading section 266. The movable section 262 is attached to the fixed section 261 to be capable of moving along one direction. The movable lens 263 is attached to the movable section 262. The movable lens 263 is used as an objective lens and focuses the measurement light that passes through the movable lens 263.

The measurement light output from the optical fiber 244 is guided to the scanning section 270 shown in FIG. 3 through the movable lens 263. A part of the measurement light reflected by the measurement object S shown in FIG. 3 passes through the scanning section 270 and thereafter is input to the optical fiber 244 through the movable lens 263.

The driving section 264 is, for example, a voice coil motor. As indicated by a thick arrow in FIG. 6, the driving section 264 moves the movable section 262 in one direction (a traveling direction of the measurement light) with respect to the fixed section 261 on an optical path of the measurement light. Consequently, it is possible to locate a focus of the measurement light on the surface of the measurement object S.

The driving circuit 265 is connected to the control board 210 shown in FIG. 3. The driving circuit 265 operates the driving section 264 on the basis of the control by the control board 210. The reading section 266 is, for example, an optical linear encoder. The reading section 266 reads a driving amount of the driving section 264 to thereby detect a relative position of the movable section 262 (the movable lens 263) with respect to the fixed section 261. The reading section 266 gives a result of the detection to the control board 210.

Figure 10:
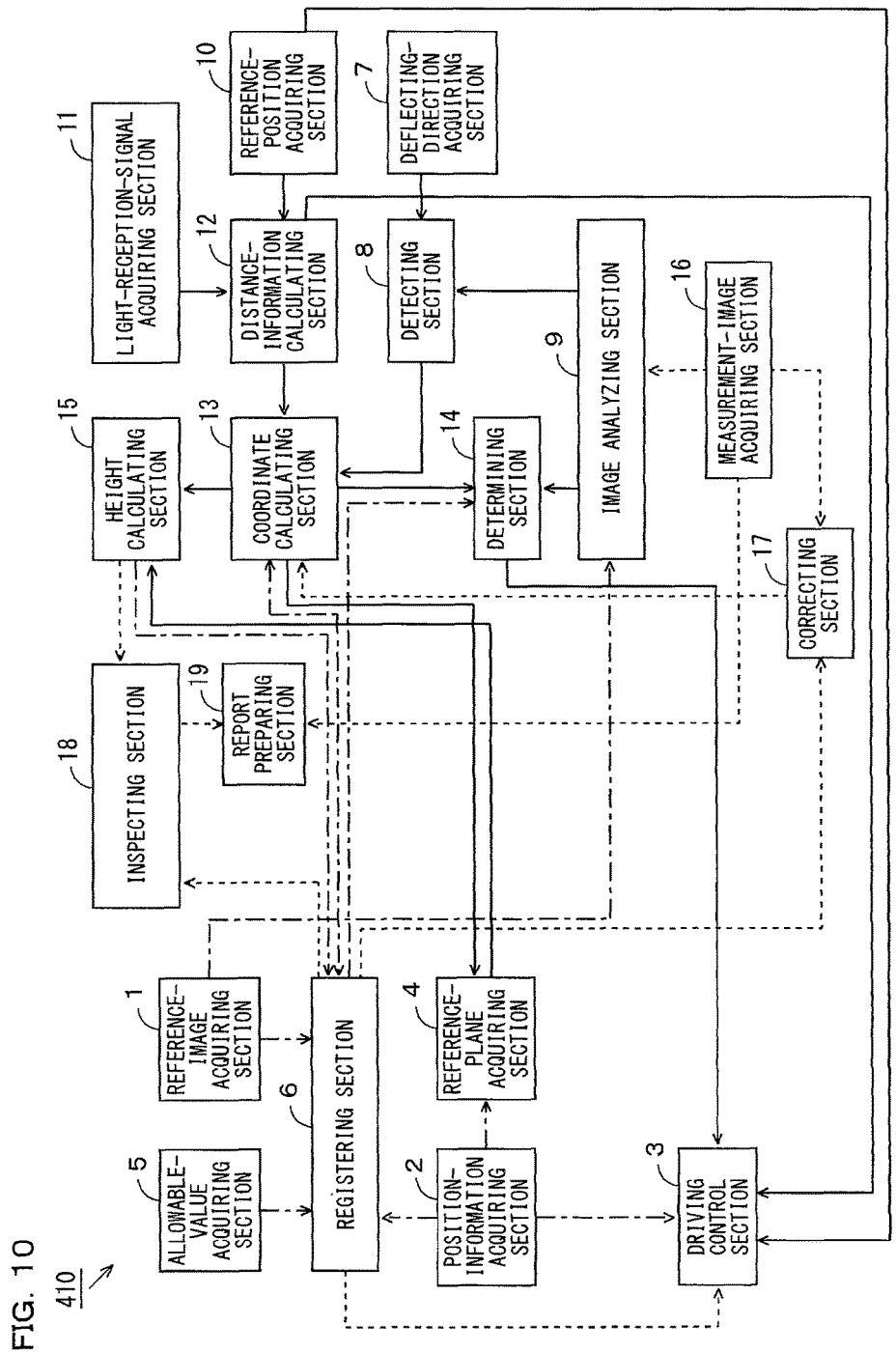
FIG. 10 is a block diagram showing a control system of the optical-scanning-height measuring device shown in FIG. 1.

The control board 210 controls the driving circuit 265 to focus the measurement light on the surface of the measurement object S on the basis of the detection result of the reading section 266 and distance information calculated by a distance-information calculating section 12 (FIG. 10). In this way, the measurement light is focused on the surface of the measurement object. Consequently, measurement accuracy of the optical-scanning-height measuring device is improved.

Note that a collimator lens that collimates the measurement light output from the optical fiber 244 may be disposed between the optical fiber 244 and the movable lens 263. In this case, the measurement light made incident on the movable lens 263 is collimated. A beam diameter of the measurement light does not change irrespective of a moving position of the movable lens 263. Therefore, it is possible to form the movable lens 263 small.

(5) The Scanning Section

Figure 7:
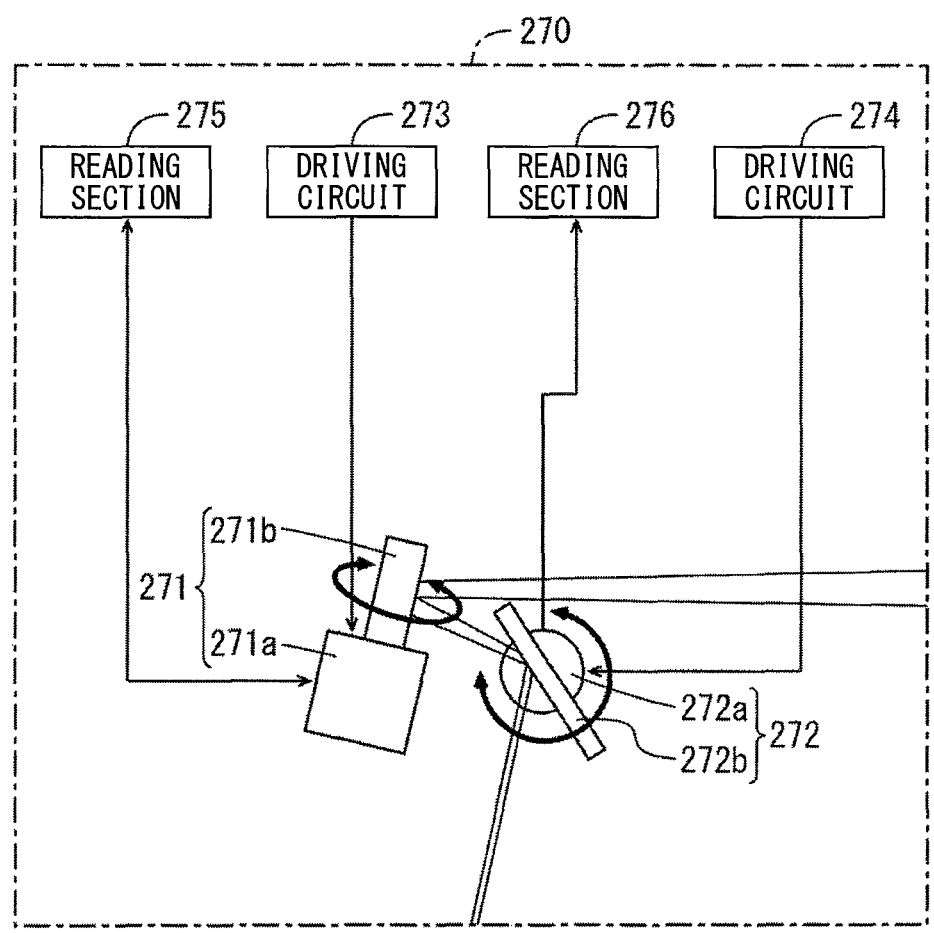
FIG. 7 is a schematic diagram showing the configuration of a scanning section.

FIG. 7 is a schematic diagram showing the configuration of the scanning section 270. As shown in FIG. 7, the scanning section 270 includes deflecting sections 271 and 272, driving circuits 273 and 274, and reading sections 275 and 276. The deflecting section 271 is configured by, for example, a galvanometer mirror and includes a driving section 271a and a reflecting section 271b. The driving section 271a is, for example, a motor having a rotating shaft in a substantially perpendicular direction. The reflecting section 271b is attached to the rotating shaft of the driving section 271a. The measurement light passed through the optical fiber 244 to the focusing section 260 shown in FIG. 3 is guided to the reflecting section 271b. The driving section 271a rotates, whereby a reflection angle of the measurement light reflected by the reflecting section 271b changes in a substantially horizontal plane.

Like the deflecting section 271, the deflecting section 272 is configured by, for example, a galvanometer mirror and includes a driving section 272a and a reflecting section 272b. The driving section 272a is, for example, a motor including a rotating shaft in the horizontal direction. The reflecting section 272b is attached to the rotating shaft of the driving section 272a. The measurement light reflected by the reflecting section 271b is guided to the reflecting section 272b. The driving section 272a is rotated, whereby a reflection angle of the measurement light reflected by the reflecting section 272b changes in a substantially perpendicular surface.

In this way, the driving sections 271a and 272a rotate, whereby the measurement light is scanned in two directions orthogonal to each other on the surface of the measurement object S shown in FIG. 3. Consequently, it is possible to irradiate the measurement light on any position on the surface of the measurement object S. The measurement light irradiated on the measurement object S is reflected on the surface of the measurement object S. A part of the reflected measurement light is sequentially reflected by the reflecting section 272b and the reflecting section 271b and thereafter guided to the focusing section 260 shown in FIG. 3.

The driving circuits 273 and 274 are connected to the control board 210 shown in FIG. 3. The driving circuits 273 and 274 respectively drive the driving sections 271a and 272a on the basis of the control by the control board 210. The reading sections 275 and 276 are, for example, an optical rotary encoder. The reading section 275 reads a driving amount of the driving section 271a to thereby detect an angle of the reflecting section 271b and gives a result of the detection to the control board 210. The reading section 276 reads a driving amount of the driving section 272a to thereby detect an angle of the reflecting section 272b and gives a result of the detection to the control board 210.

(6) Operation Modes

Figure 8:
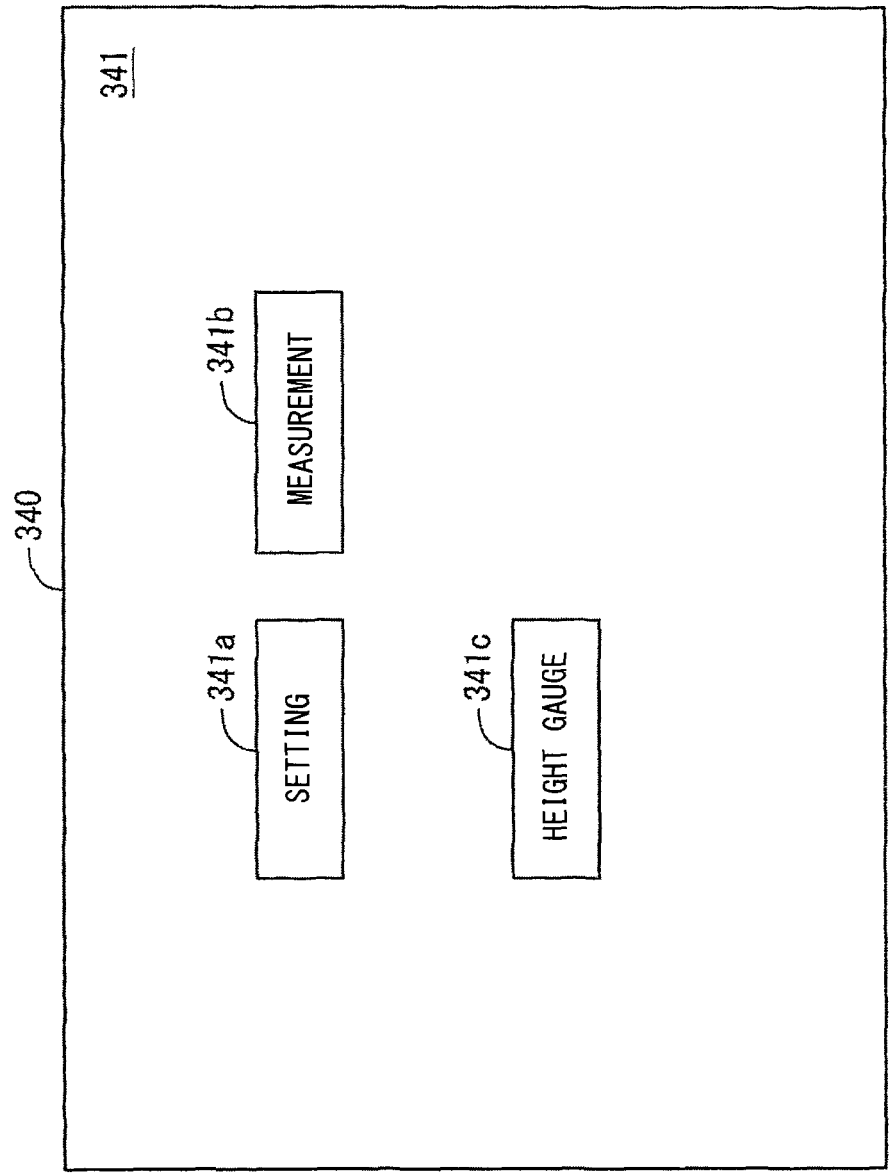
FIG. 8 is a diagram showing an example of a selection screen displayed on a display section of the optical-scanning-height measuring device.

The optical-scanning-height measuring device 400 shown in FIG. 1 operates in an operation mode selected from a plurality of operation modes by the user. Specifically, the operation modes include a setting mode, a measurement mode, and a height gauge mode. FIG. 8 is a diagram showing an example of a selection screen 341 displayed on the display section 340 of the optical-scanning-height measuring device 400.

As shown in FIG. 8, on the selection screen 341 of the display section 340, a setting button 341a, a measurement button 341b, and a height gauge button 341c are displayed. The user operates the setting button 341a, the measurement button 341b, and the height gauge button 341c using the operation section 330 shown in FIG. 1, whereby the optical-scanning-height measuring device 400 operates respectively in the setting mode, the measurement mode, and the height gauge mode.

In the following explanation, among users, a skilled user who manages measurement work of the measurement object S is referred to as measurement manager as well and a user who performs the measurement work of the measurement object S under the management of the measurement manager is referred to as measurement operator as appropriate. The setting mode is mainly used by the measurement manager. The measurement mode is mainly used by the measurement operator.

In the optical-scanning-height measuring device 400, a three-dimensional coordinate system peculiar to a space including the measurement region V shown in FIG. 2 is defined in advance by an X axis, a Y axis, and a Z axis. The X axis and the Y axis are parallel to the optical surface plate 111 shown in FIG. 2 and orthogonal to each other. The Z axis is orthogonal to the X axis and the Y axis. In the operation modes, data of a coordinate specified by the coordinate system and data of a plane coordinate on an image acquired by imaging of the imaging section 220 are transmitted between the control section 310 and the control board 210. FIGS. 9A to 9C are diagrams showing contents of data transmitted between the control section 310 and the control board 210 in the operation modes.

In the setting mode, the measurement manager can register information concerning a desired measurement object S in the optical-scanning-height measuring device 400. Specifically, the measurement manager places the desired measurement object S on the optical surface plate 111 shown in FIG. 2 and images the measurement object S with the imaging section 220 shown in FIG. 3. The measurement manager designates, on the image, as a measurement point, a portion that should be measured of the measurement object S displayed on the display section 340 shown in FIG. 1. In this case, as shown in FIG. 9A, the control section 310 gives a plane coordinate (Ua, Va) specified by the designated measurement point designated on the image to the control board 210.

The control board 210 specifies a three-dimensional coordinate (Xc, Yc, Zc) of a position corresponding to the plane coordinate (Ua, Va) in the measurement region V shown in FIG. 2 and gives the specified three-dimensional coordinate (Xc, Yc, Zc) to the control section 310. The control section 310 causes the storing section 320 shown in FIG. 1 to store the three-dimensional coordinate (Xc, Yc, Zc) given by the control board 210. The control section 310 calculates height of the portion corresponding to the measurement point on the basis of information such as the three-dimensional coordinate (Xc, Yc, Zc) stored in the storing section 320 and a reference plane explained below and causes the storing section 320 to store a result of the calculation.

The measurement mode is used to measure the height of the portion corresponding to the measurement point concerning the measurement object S of the same type as the measurement object S, the information of which is registered in the optical-scanning-height measuring device 400 in the setting mode. Specifically, the measurement operator places, on the optical surface plate 111, the measurement object S of the same type as the measurement object S, the information of which is registered in the optical-scanning-height measuring device 400 in the setting mode, and images the measurement object S with the imaging section 220. In this case, as shown in FIG. 9B, the control section 310 gives the three-dimensional coordinate (Xc, Yc, Zc) stored in the storing section 320 in the setting mode to the control board 210.

The control board 210 calculates a three-dimensional coordinate (Xb, Yb, Zb) of the portion of the measurement object S corresponding to the measurement point on the basis of the acquired three-dimensional coordinate (Xc, Yc, Zc). The control board 210 gives the calculated three-dimensional coordinate (Xb, Yb, Zb) to the control section 310. The control section 310 calculates height of the portion corresponding to the measurement point on the basis of information such as the three-dimensional coordinate (Xb, Yb, Zb) given by the control board 210 and the reference plane explained below. The control section 310 causes the display section 340 shown in FIG. 1 to display a result of the calculation.

In this way, in the measurement mode, the measurement operator can acquire the height of the portion that should be measured of the measurement object S without designating the portion. Therefore, even when the measurement operator is not skilled, it is possible to easily and accurately measure a shape of a desired portion of the measurement object. The three-dimensional coordinate (Xc, Yc, Zc) is stored in the storing section 320 in the setting mode. Therefore, in the measurement mode, it is possible to quickly specify the portion corresponding to the measurement point on the basis of the stored three-dimensional coordinate (Xc, Yc, Zc).

In this embodiment, in the setting mode, the three-dimensional coordinate (Xc, Yc, Zc) corresponding to the plane coordinate (Ua, Va) is specified and stored in the storing section 320. However, the present invention is not limited to this. In the setting mode, a plane coordinate (Xc, Yc) corresponding to the plane coordinate (Ua, Va) may be specified and a component Zc of the Z axis may be not specified. In this case, the specified plane coordinate (Xc, Yc) is stored in the storing section 320. In the measurement mode, the plane coordinate (Xc, Yc) stored in the storing section 320 is given to the control board 210.

The height gauge mode is used by the user to designate a desired portion of the measurement object S as the measurement point on the screen and measure height of the portion while confirming the measurement object S on the screen. Specifically, the user places the desired measurement object S on the optical surface plate 111 and images the measurement object S with the imaging section 220. The user designates, as the measurement point, a portion that should be measured on an image of the measurement object S displayed on the display section 340. In this case, as shown in FIG. 9C, the control section 310 gives the plane coordinate (Ua, Va) specified by the designated measurement point on the image to the control board 210.

The control board 210 specifies a three-dimensional coordinate (Xc, Yc, Zc) of the position corresponding to the plane coordinate (Ua, Va) in the measurement region V shown in FIG. 2 and calculates, on the basis of the specified three-dimensional coordinate (Xc, Yc, Zc), a three-dimensional coordinate (Xb, Yb, Zb) of the portion of the measurement object S corresponding to the measurement point. The control board 210 gives the calculated three-dimensional coordinate (Xb, Yb, Zb) to the control section 310. The control section 310 calculates height of the portion corresponding to the measurement point on the basis of information such as the three-dimensional coordinate (Xb, Yb, Zb) given by the control board 210 and the reference plane explained below and causes the display section 340 to display a result of the calculation.

In the storing section 320 shown in FIG. 1, coordinate conversion information and position conversion information are stored in advance. The coordinate conversion information indicates plane coordinates (Xc, Yc) corresponding to plane coordinates (Ua, Va) in positions in the height direction (the Z-axis direction) in the measurement region V. The control board 210 can irradiate the measurement light on a desired position in the measurement region V by controlling positions of the movable sections 252a and 252b shown in FIG. 5 and angles of the reflecting sections 271b and 272b shown in FIG. 7. The position conversion information indicates a relation between the coordinates in the measurement region V and the positions of the movable sections 252a and 252b and the angles of the reflecting sections 271b and 272b.

A control system configured by the control section 310 and the control board 210 can specify a three-dimensional coordinate (Xc, Yc, Zc) and a three-dimensional coordinate (Xb, Yb, Zb) of a position corresponding to the measurement position by using the coordinate conversion information and the position conversion information. Details of the coordinate conversion information and the position conversion information are explained below.

(7) A Control System of the Optical-Scanning-Height Measuring Device (a) Overall Configuration of the Control System FIG. 10 is a block diagram showing a control system of the optical-scanning-height measuring device 400 shown in FIG. 1. As shown in FIG. 10, a control system 410 includes a reference-image acquiring section 1, a position-information acquiring section 2, a driving control section 3, a reference-plane acquiring section 4, an allowable-value acquiring section 5, a registering section 6, a deflecting-direction acquiring section 7, a detecting section 8, and an image analyzing section 9. The control system 410 further includes a reference-position acquiring section 10, a light-reception-signal acquiring section 11, a distance-information calculating section 12, a coordinate calculating section 13, a determining section 14, a height calculating section 15, a measurement-image acquiring section 16, a correcting section 17, an inspecting section 18, and a report preparing section 19.

The control board 210 and the control section 310 shown in FIG. 1 execute the system program stored in the storing section 320, whereby functions of the components of the control system 410 are realized. In FIG. 10, a flow of common processing in all the operation modes is indicated by a solid line, a flow of processing in the setting mode is indicated by an alternate long and short dash line, and a flow of processing in the measurement mode is indicated by a dotted line. The same applies in FIG. 35 referred to below. A flow of processing in the height gauge mode is substantially equal to a flow of processing in the setting mode. In the following explanation, to facilitate understanding, the components of the control system 410 in the setting mode and the measurement mode are separately explained.

(b) The Setting Mode

The measurement administrator places a desired measurement object S on the optical surface plate 111 shown in FIG. 2 and images the measurement object S with the imaging section 220 shown in FIG. 3. The reference-image acquiring section 1 acquires, as reference image data, image data generated by the imaging section 220 and causes the display section 340 shown in FIG. 1 to display, as a reference image, an image based on the acquired reference image data. The reference image displayed on the display section 340 may be a still image or may be a moving image that is sequentially updated. The measurement manager can designate, as the reference point, a portion that should be measured and designate a reference point on the reference image displayed on the display section 340. The reference point is a point for deciding a reference plane serving as a reference in calculating height of the measurement object S.

The position-information acquiring section 2 receives designation of the measurement point on the reference image acquired by the reference-image acquiring section 1 and acquires a position (the plane coordinate (Ua, Va) explained above) of the received measurement point. The position-information acquiring section 2 receives designation of a reference point using the reference image and acquires a position of the received reference point. The position-information acquiring section 2 is also capable of receiving a plurality of measurement points and capable of receiving a plurality of reference points.

The driving control section 3 acquires a position of the measurement head 200 from the reading section 133 of the lift 130 shown in FIG. 3 and controls the driving circuit 132 shown in FIG. 3 on the basis of the acquired position of the measurement head 200. Consequently, the measurement head 200 is moved to a desired position in the up-down direction. The driving control section 3 acquires a position of the movable lens 263 from the reading section 266 of the focusing section 260 shown in FIG. 6 and controls the driving circuit 265 shown in FIG. 6 on the basis of the acquired position of the movable lens 263. Consequently, the movable lens 263 is moved such that the measurement light is focused near the surface of the measurement object S.

The driving control section 3 controls the driving circuits 273 and 274 shown in FIG. 7 and the driving circuits 256a and 256b shown in FIG. 5 on the basis of the position conversion information stored in the storing section 320 shown in FIG. 1 and the position acquired by the position-information acquiring section 2. Consequently, the angles of the reflecting sections 271b and 272b of the deflecting sections 271 and 272 shown in FIG. 7 are adjusted. The measurement light is irradiated on the portions of the measurement object S corresponding to the measurement point and the reference point.

The driving control section 3 adjusts, according to the change in the optical path length of the measurement light, the optical path length of the reference light to reduce a difference between the optical path length of the measurement light and the optical path length of the reference light to a fixed value or less. More specifically, in the driving control section 3, a threshold concerning the difference between the optical path length of the measurement light and the optical path length of the reference light is set in advance such that appropriate interference light is obtained. Therefore, when the difference between the optical path length of the measurement light and the optical path length of the reference light calculated by the distance-information calculating section 12 explained below is equal to or smaller than the threshold, the driving control section 3 controls the driving circuits 256a and 256b shown in FIG. 5 to maintain the optical path length of the reference light. On the other hand, when the difference between the optical path length of the measurement light and the optical path length of the reference light is larger than the threshold, the driving control section 3 controls the driving circuits 256a and 256b shown in FIG. 5 to change the optical path length of the reference light. Consequently, it is possible to easily adjust the optical path length of the reference light to appropriate size. Therefore, a measurable height range of the measurement object S is expanded.

According to the operation of the driving control section explained above, coordinates of the portions of the measurement object S corresponding to the measurement point and the reference point are calculated by the coordinate calculating section 13 as explained below. Details of the operation of the driving control section 3 are explained below. In the following explanation, processing for calculating a coordinate of the portion of the measurement object S corresponding to the measurement point is explained. However, processing for calculating a coordinate of the portion of the measurement object S corresponding to the reference point is the same as the processing for calculating a coordinate of the portion of the measurement object S corresponding to the measurement point.

The reference-plane acquiring section 4 acquires a reference plane on the basis of one or a plurality of coordinates calculated by the coordinate calculating section 13 according to one or a plurality of reference points acquired by the position-information acquiring section 2. Concerning the measurement point acquired by the position-information acquiring section 2, the measurement manager can input an allowable value for height. The allowable value is used for inspection of the measurement object S in the measurement mode explained below and includes a design value and a tolerance from the design value. The allowable-value acquiring section 5 receives the input allowable value.

The registering section 6 registers the reference image data acquired by the reference-image acquiring section 1, the position acquired by the position-information acquiring section 2, and the allowable value set by the allowable-value acquiring section 5 in association with one another. Specifically, the registering section 6 causes the storing section 320 to store registration information indicating a relation among the reference image data, the positions of the measurement point and the reference point, and allowable values corresponding to measurement values. A plurality of reference planes may be set. In this case, the registering section 6 registers, for each of the reference planes, a reference point corresponding to the reference plane, a measurement point corresponding to the reference plane, and allowable values corresponding to the measurement values in association with one another.

The deflecting-direction acquiring section 7 acquires the angles of the reflecting sections 271b and 272b respectively from the reading sections 275 and 276 shown in FIG. 7. The detecting section 8 detects deflecting directions of the deflecting sections 271 and 272 respectively on the basis of the angles of the reflecting sections 271b and 272b acquired by the deflecting-direction acquiring section 7. The imaging of the imaging section 220 is continued, whereby the measurement light on the measurement object S appears in the reference image. The image analyzing section 9 analyzes the reference image data acquired by the reference-image acquiring section 1. The detecting section 8 detects, on the basis of a result of the analysis by the image analyzing section 9, a plane coordinate indicating an irradiation position on the reference image of the measurement light deflected by the deflecting sections 271 and 272.

The reference-position acquiring section 10 acquires positions of the movable sections 252a and 252b respectively from the reading sections 257a and 257b of the reference section 250 shown in FIG. 5. The light-reception-signal acquiring section 11 acquires a light reception signal from the light receiving section 232d shown in FIG. 4. The distance-information calculating section 12 performs, on the basis of the light reception signal acquired by the light receiving section 232d, a predetermined arithmetic operation and predetermined processing on data indicating a relation between a wavelength and a received light amount of interference light. The arithmetic operation and the processing include, for example, a frequency axis conversion from a wavelength to a wave number and Fourier transform of the wave number.

The distance-information calculating section 12 calculates a difference between the optical path length of the measurement light and the optical path length of the reference light on the basis of the data obtained by the processing and the positions of the movable sections 252a and 252b acquired by the reference-position acquiring section 10. The distance-information calculating section 12 calculates, on the basis of the calculated difference, distance information indicating the distance between the emitting position of the measurement light in the measurement head 200 and the irradiation position of the measurement light in the measurement object S shown in FIG. 2. The emitting position of the measurement light in the measurement head 200 is, for example, the position of the port 245d of the light guide section 240 shown in FIG. 3.

The coordinate calculating section 13 calculates a three-dimensional coordinate (Xc, Yc, Zc) of the irradiation position of the measurement light on the measurement object S on the basis of the deflecting directions of the deflecting sections 271 and 272 detected by the detecting section 8 and the distance information calculated by the distance-information calculating section 12. The three-dimensional coordinate (Xc, Yc, Zc) of the irradiation position of the measurement light includes a coordinate Zc in the height direction and a plane coordinate (Xc, Yc) in a plane orthogonal to the height direction.

The coordinate calculating section 13 may calculate, using, for example, the triangulation system, a three-dimensional coordinate of the irradiation position of the measurement light on the measurement object S on the basis of a plane coordinate indicating an irradiation position on the reference image of the measurement light detected by the detecting section 8 and the deflecting directions of the deflecting sections 271 and 272. Alternatively, the coordinate calculating section 13 may calculate a three-dimensional coordinate of the irradiation position of the measurement light on the measurement object S on the basis of a plane coordinate indicating the irradiation position on the reference image of the measurement light detected by the detecting section 8 and the distance information calculated by the distance-information calculating section 12.

The determining section 14 determines whether the measurement light is irradiated on the portion of the measurement object S corresponding to the measurement point or a portion near the portion. Specifically, the coordinate calculating section 13 acquires, on the basis of the calculated coordinate in the height direction and the coordinate conversion information stored in the storing section 320, a plane coordinate (a plane coordinate (Xa', Ya') explained below) corresponding the measurement point registered by the registering section 6. The determining section 14 determines whether the plane coordinate (Xc, Yc) calculated by the coordinate calculating section 13 is present within a range decided in advance from the plane coordinate (Xa', Ya') corresponding to the measurement point.

Alternatively, the image analyzing section 9 may perform an image analysis of the reference image data to thereby specify a plane coordinate (a plane coordinate (Uc, Vc) explained below) of the irradiation position of the measurement light in the reference image. In this case, the determining section 14 determines whether the plane coordinate (Uc, Vc) of the irradiation position of the measurement light specified by the image analyzing section 9 is present within a range decided in advance from the plane coordinate (Ua, Va) of the measurement point registered by the registering section 6.

When the determining section 14 determines that the measurement light is not irradiated on the portion of the measurement object S corresponding to the measurement point and the portion near the portion, the driving control section 3 controls the driving circuits 273 and 274 shown in FIG. 7 and the driving circuits 256a and 256b shown in FIG. 5 to move the irradiation position of the measurement light. When the determining section 14 determines that the measurement light is irradiated on the portion of the measurement object S corresponding to the measurement point and the portion near the portion, the driving control section 3 controls the driving circuits 273 and 274 and the driving circuits 256a and 256b to fix the irradiation position of the measurement light.

The coordinate calculating section 13 gives the coordinate calculated concerning the reference point to the reference-plane acquiring section 4. The height calculating section 15 calculates, on the basis of the three-dimensional coordinate (Xc, Yc, Zc) calculated by the coordinate calculating section 13 according to the measurement point, height of the portion of the measurement object S based on the reference plane acquired by the reference-plane acquiring section 4. For example, when the reference plane is a plane, the height calculating section 15 calculates, as height, length from the reference plane to three-dimensional coordinate (Xc, Yc, Zc) in the perpendicular of the reference plane passing the three-dimensional coordinate (Xc, Yc, Zc). The height calculating section 15 causes the display section 340 to display the calculated height. The registering section 6 registers, as registration information, the three-dimensional coordinate (Xc, Yc, Zc) calculated by the coordinate calculating section 13 and the height calculated by the height calculating section 15 in association with the reference image data, the position of the measurement point, the position of the reference point, and the allowable value.

(c) The Measurement Mode

The measurement operator places the measurement object S of the same type as the measurement object S, the registration information of which is registered in the setting mode, on the optical surface plate 111 shown in FIG. 2 and images the measurement object S with the imaging section 220 shown in FIG. 3. The measurement-image acquiring section 16 acquires, as measurement image data, image data generated by the imaging section 220 and causes the display section 340 shown in FIG. 1 to display, as a measurement image, an image based on the acquired measurement image data.

The correcting section 17 corrects deviation of the measurement image data with respect to the reference image data on the basis of the registration information registered by the registering section 6. Consequently, the correcting section 17 sets, in the measurement image data, a measurement point and a reference point corresponding to the registration information registered by the registering section 6.

The driving control section 3 controls the driving circuits 273 and 274 shown in FIG. 7 and the driving circuits 256a and 256b shown in FIG. 5 on the basis of the registration information registered by the registering section 6 in the setting mode. Consequently, three-dimensional coordinates of portions of the measurement object S corresponding to the measurement point and the reference point set by the correcting section 17 are calculated by the coordinate calculating section 13. The driving control section 3 performs the control on the basis of the three-dimensional coordinates and the heights registered in the setting mode. Therefore, the coordinate calculating section 13 can efficiently calculate the three-dimensional coordinates of the portions of the measurement object S corresponding to the measurement point and the reference point set by the correcting section 17.

The kinds of processing by the deflecting-direction acquiring section 7 and the detecting section 8 in the measurement mode are respectively the same as the kinds of processing by the deflecting-direction acquiring section 7 and the detecting section 8 in the setting mode. The processing by the image analyzing section 9 in the measurement mode is the same as the processing by the image analyzing section 9 in the setting mode except that the measurement image data acquired by the measurement-image acquiring section 16 is used instead of the reference image data acquired by the reference-image acquiring section 1. The kinds of processing by the reference-position acquiring section 10, the light-reception-signal acquiring section 11, and the distance-information calculating section 12 in the measurement mode are respectively the same as the kinds of processing by the reference-position acquiring section 10, the light-reception-signal acquiring section 11, and the distance-information calculating section 12 in the setting mode.

The coordinate calculating section 13 calculates a three-dimensional coordinate (Xb, Yb, Zb) of the irradiation position of the measurement light on the measurement object S on the basis of the deflecting directions of the deflecting sections 271 and 272 detected by the detecting section 8 and the distance information calculated by the distance-information calculating section 12. The coordinate calculating section 13 may calculate the three-dimensional coordinate (Xb, Yb, Zb) of the irradiation position of the measurement light on the measurement object S on the basis of the plane coordinate indicating the irradiation position on the measurement image of the measurement light detected by the detecting section 8 and the distance information calculated by the distance-information calculating section 12. The three-dimensional coordinate (Xb, Yb, Zb) of the irradiation position of the measurement light includes a coordinate Zb in the height direction and a plane coordinate (Xb, Yb) in the plane orthogonal to the height direction.

The processing by the determining section 14 in the measurement mode is the same as the processing by the determining section 14 in the setting mode except that the measurement point set by the correcting section 17 is used instead of the measurement point registered by the registering section 6 and that the three-dimensional coordinate (Xb, Yb, Zb) is used instead of the three-dimensional coordinate (Xc, Yc, Zc). Consequently, the coordinate calculating section 13 calculates a coordinate corresponding to the reference point set by the correcting section 17.

The reference-plane acquiring section 4 acquires a reference plane on the basis of a coordinate corresponding to the reference point calculated by the coordinate calculating section 13. The height-calculating section 15 calculates, on the basis of the three-dimensional coordinate (Xb, Yb, Zb) calculated by the coordinate calculating section 13, height of a portion of the measurement object S based on the reference plane acquired by the reference-plane acquiring section 4.

The inspecting section 18 inspects the measurement object S on the basis of the height of the portion of the measurement object S calculated by the height calculating section 15 and the allowable value registered in the registering section 6. Specifically, when the calculated height is within a range of the tolerance based on the design value, the inspecting section 18 determines that the measurement object S is a non-defective product. On the other hand, when the calculated height is outside the range of the tolerance based on the setting value, the inspecting section 18 determines that the measurement object S is a defective product.

Figure 11:
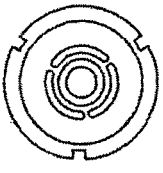
FIG. 11 is a diagram showing an example of a report prepared by a report preparing section.
Figure 12:
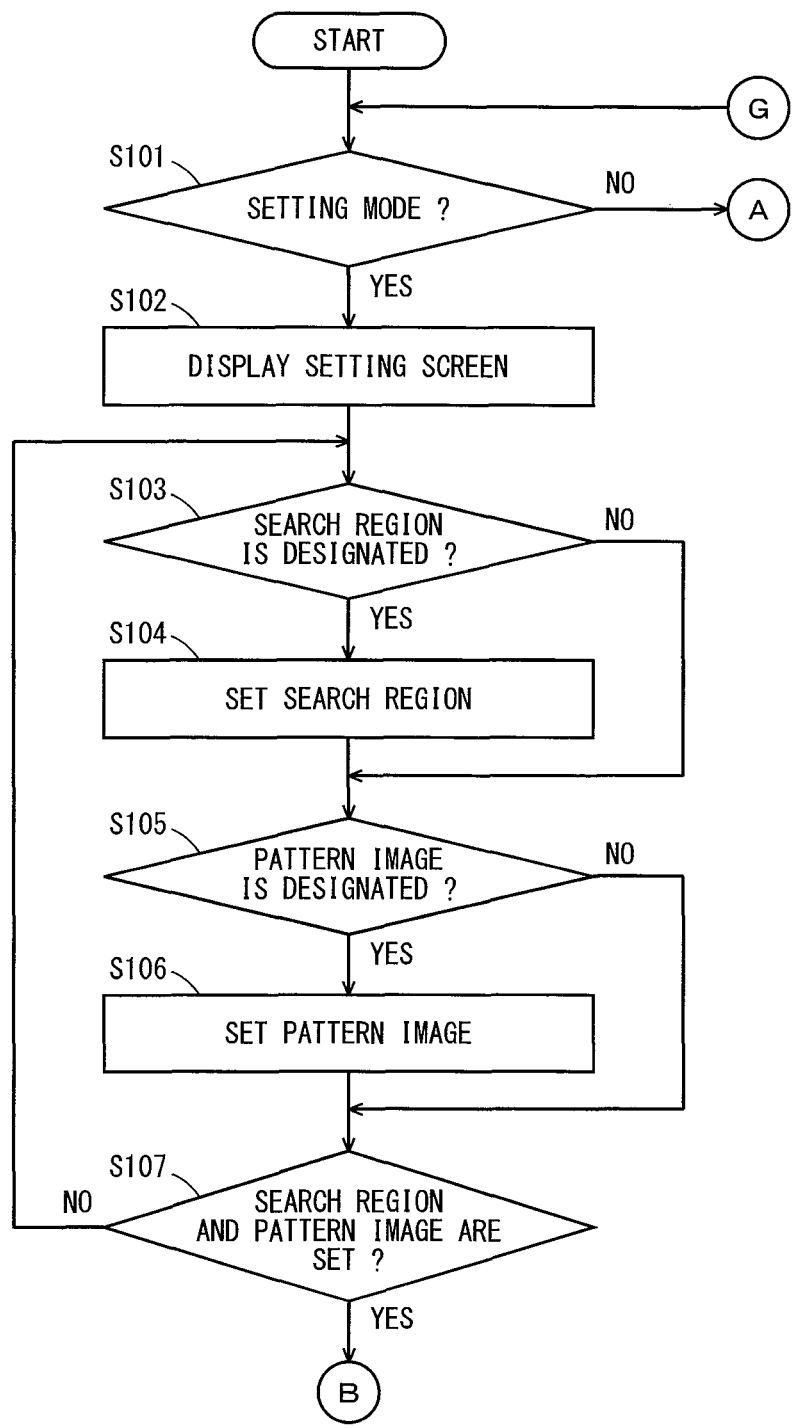
FIG. 12 is a flowchart for explaining an example of optical scanning height measurement processing executed in the optical-scanning-height measuring device shown in FIG. 1.
Figure 13:
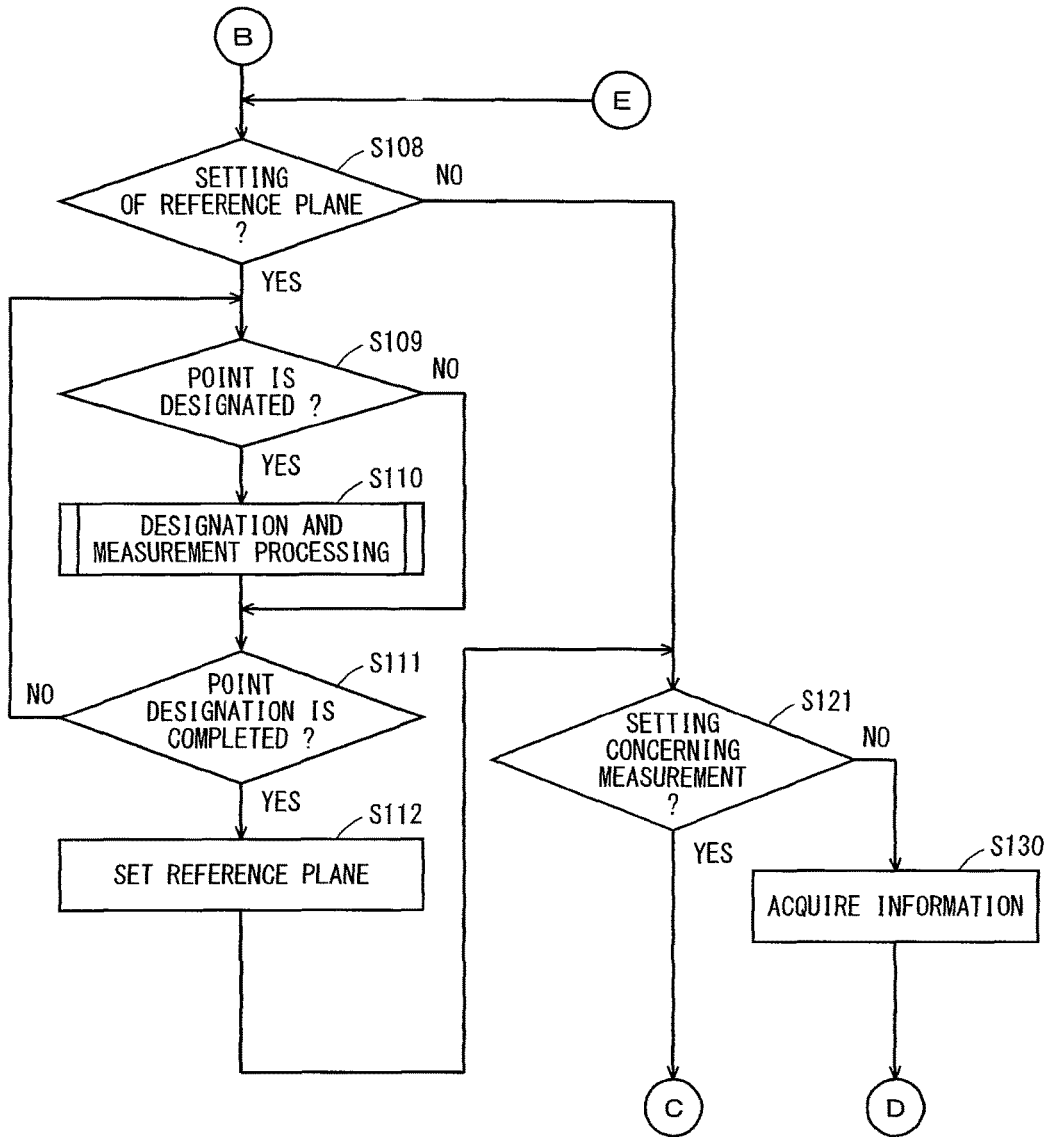
FIG. 13 is a flowchart for explaining the example of the optical scanning height measurement processing executed in the optical-scanning-height measuring device shown in FIG. 1.
Figure 14:
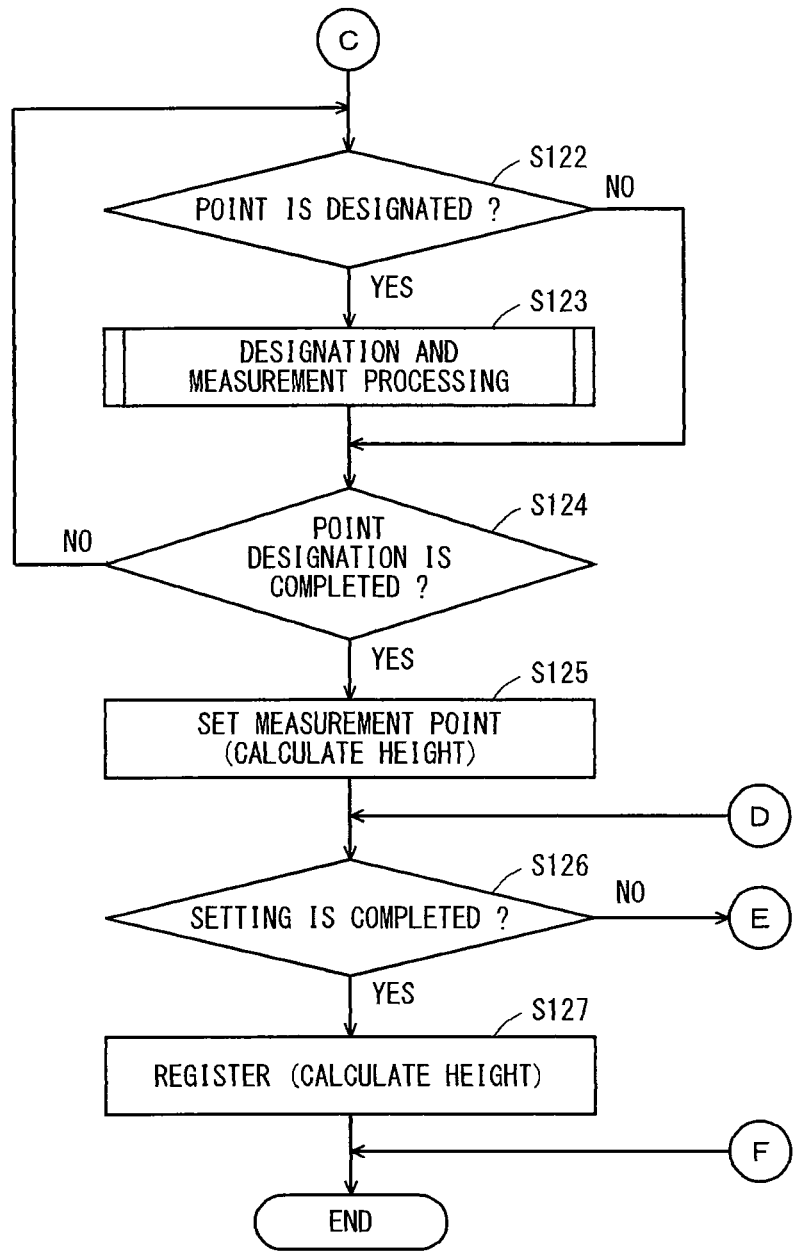
FIG. 14 is a flowchart for explaining the example of the optical scanning height measurement processing executed in the optical-scanning-height measuring device shown in FIG. 1.

The report preparing section 19 prepares a report on the basis of a result of the inspection by the inspecting section 18 and the reference image acquired by the measurement-image acquiring section 16. Consequently, the measurement operator can easily report the inspection result concerning the measurement object S to the measurement manager or the other users using the report. The report is prepared according to a description format determined in advance. FIG. 11 is a diagram showing an example of the report prepared by the report preparing section 19.

In the description format shown in FIG. 11, a report 420 includes a name display field 421, an image display field 422, a state display field 423, a result display field 424, and a guarantee display field 425. In the name display field 421, a name (in the example shown in FIG. 11, "inspection result sheet") of the report 420 is displayed. In the image display field 422, a measurement image of an inspection target is displayed. In the state display field 423, a name of the inspection target, an identification number of the inspection target, a name of a measurement operator, an inspection date and time, and the like are displayed.

In the result display field 424, an inspection result concerning the inspection target is displayed. Specifically, in the result display field 424, names, measurement values, and determination results of various inspection items set for the inspection target are displayed in a form of a list table in a state in which the measurement values and the determination results are associated with design values and tolerances. The guarantee display field 425 is a blank for a signature or a seal. The measurement operator and the measurement manager can guarantee an inspection result by signing or sealing the guarantee display field 425.

The report preparing section 19 may prepare the report 420 only concerning the measurement object S determined as a non-defective product by the inspecting section 18. The report 420 is attached to a statement of delivery in order to guarantee the quality of an inspection target product when the inspection target product is delivered to a customer. The report preparing section 19 may prepare the report 420 only concerning the measurement object S determined as a defective product by the inspecting section 18. The report 420 is used in the own company in order to analyze a cause of the determination that the inspection target product is the defective product.

(d) The Height Gauge Mode

The user places a desired measurement object S on the optical surface plate 111 shown in FIG. 2 and images the measurement object S with the imaging section 220 shown in FIG. 3. The reference-image acquiring section 1 acquires image data generated by the imaging section 220 and causes the display section 340 shown in FIG. 1 to display an image based on the acquired image data. The user designates, as a measurement point, a portion that should be measured on the image displayed on the display section 340.

The position-information acquiring section 2 receives designation of a measurement point on an image acquired by the reference-image acquiring section 1 and acquires a position (the plane coordinate (Ua, Va) explained above) of the received measurement point. The position-information acquiring section 2 receives designation of a reference point using the reference image and acquires a position of the received reference point. The position-information acquiring section 2 is also capable of receiving a plurality of measurement points and capable of receiving a plurality of reference points.

The driving control section 3 controls the driving circuits 273 and 274 shown in FIG. 7 and the driving circuits 256a and 256b shown in FIG. 5 on the basis of the position conversion information stored in the storing section 320 shown in FIG. 1 and the position acquired by the position-information acquiring section 2. Consequently, measurement light is irradiated on portions of the measurement object S corresponding to the measurement point and the reference point and an optical path length of reference light is adjusted.

According to the operation of the driving control section explained above, coordinates of the portions of the measurement object S corresponding to the measurement point and the reference point are calculated by the coordinate calculating section 13. The reference-plane acquiring section 4 acquires a reference plane on the basis of the coordinate calculated by the coordinate-calculating section 13 according to the reference point acquired by the position-information acquiring section 2.

The kinds of processing by the deflecting-direction acquiring section 7, the detecting section 8, the image analyzing section 9, the reference-position acquiring section 10, the light-reception-signal acquiring section 11, and the distance-information calculating section 12 in the height gauge mode are respectively the same as the kinds of processing by the deflecting-direction acquiring section 7, the detecting section 8, the image analyzing section 9, the reference-position acquiring section 10, the light-reception-signal acquiring section 11, and the distance-information calculating section 12 in the setting mode.

The coordinate calculating section 13 calculates a three-dimensional coordinate (Xb, Yb, Zb) of the irradiation position of the measurement light on the measurement object S on the basis of the deflecting directions of the deflecting sections 271 and 272 or the irradiation position of the measurement light detected by the detecting section 8 and the distance information calculated by the distance-information calculating section 12. The coordinate calculating section 13 may calculate the three-dimensional coordinate (Xb, Yb, Zb) of the irradiation position of the measurement light on the measurement object S on the basis of the plane coordinate indicating the irradiation position on the measurement image of the measurement light detected by the detecting section 8 and the distance information calculated by the distance-information calculating section 12. The kinds or processing by the determining section 14 and the height calculating section 15 in the height gauge mode are respectively the same as the kinds of processing by the determining section 14 and the height calculating section 15 in the setting mode.

(8) An Overall Flow of the Control System

FIGS. 12 to 15 are flowcharts for explaining an example of optical scanning height measurement processing executed in the optical-scanning-height measuring device 400 shown in FIG. 1. A series of processing explained below is executed at a fixed cycle by the control section 310 and the control board 210 when a power supply of the optical-scanning-height measuring device 400 is in an ON state. Note that the optical scanning height measurement processing includes designation and measurement processing and actual measurement processing explained below. In the following explanation, either one of the designation and measurement processing and the actual measurement processing in the optical scanning height measurement processing is executed by the control board 210. The other of the designation and measurement processing and the actual measurement processing in the optical scanning height measurement processing is executed by the control section 310. However, the present invention is not limited to this. For example, both of the designation and measurement processing and the actual measurement processing in the optical scanning height measurement processing may be executed by the control board 210 or the control section 310.

In an initial state, it is assumed that the power supply of the optical-scanning-height measuring device 400 is on in a state in which the measurement object S is placed on the optical surface plate 111 shown in FIG. 2. At this point, the selection screen 341 shown in FIG. 8 is displayed on the display section 340 shown in FIG. 1.

When the optical scanning height measurement processing is started, the control section 310 determines whether the setting mode is selected by operation of the operation section 330 by the user (step S101). More specifically, the control section 310 determines whether the setting button 341a shown in FIG. 8 is operated by the user.

Figure 15:
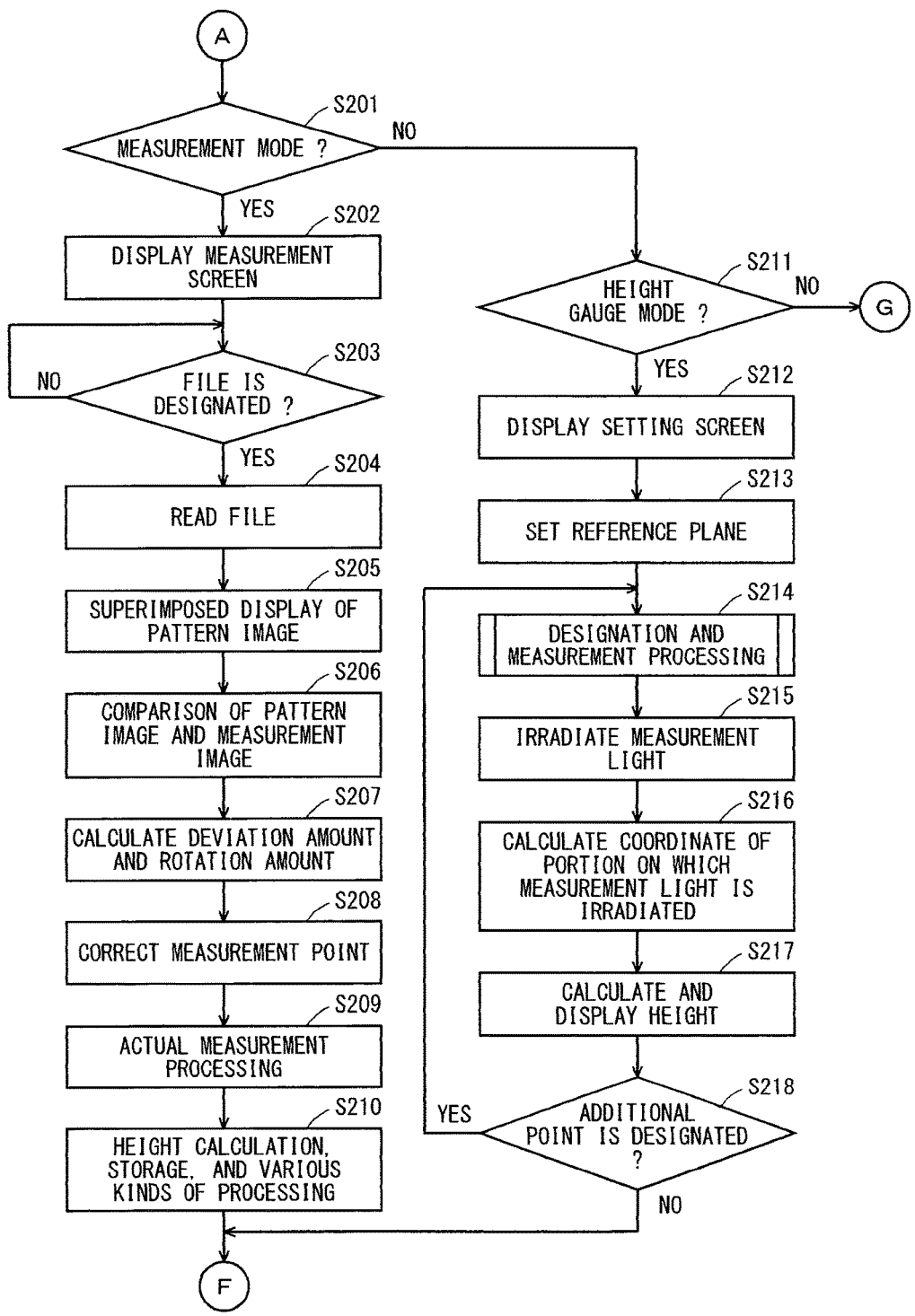
FIG. 15 is a flowchart for explaining the example of the optical scanning height measurement processing executed in the optical-scanning-height measuring device shown in FIG. 1.

When the setting mode is not selected, the control section 310 proceeds to processing in step S201 of FIG. 15 explained below. On the other hand, when the setting mode is selected, the control section 310 causes the display section 340 shown in FIG. 1 to display a setting screen 350 shown in FIG. 23 explained below (step S102). On the setting screen 350, a reference image of the measurement region V shown in FIG. 2 acquired at a fixed cycle by the imaging section 220 is displayed on a real-time basis.

In the optical-scanning-height measuring device 400 according to this embodiment, in order to realize a correcting function of the correcting section 17 shown in FIG. 10, it is necessary to set a pattern image and a search region in the setting mode. The pattern image means an image of a portion including at least the measurement object S in an entire region of a reference image displayed at a point in time designated by the user. The search region means a range (a range in an imaging visual field of the imaging section 220) in which, after the pattern image is set in the setting mode, a portion similar to the pattern image is searched in a measurement image in the measurement mode.

Thus, the control section 310 determines whether a search region is designated by the operation of the operation section 330 by the user (step S103). When a search region is not designated, the control section 310 proceeds to processing in step S105 explained below. On the other hand, when a search region is designated, the control section 310 sets the designated search region by storing information concerning the designated search region in the storing section 320 (step S104).

Subsequently, the control section 310 determines whether a pattern image is designated by the operation of the operation section 330 by the user (step S105). When a pattern image is not designated, the control section 310 proceeds to processing in step S107 explained below. On the other hand, when a pattern image is designated, the control section 310 sets the designated pattern image by storing information concerning the designated pattern image in the storing section 320 (step S106). Note that the information concerning the pattern image includes information indicating a position of the pattern image in the reference image. Specific setting examples of the pattern image and the search region by the user are explained below.

Subsequently, the control section 310 determines whether the search region and the pattern image are set by the processing in steps S104 and S105 (step S107). When at least one of the search region and the pattern image is not set, the control section 310 returns to the processing in step S103. On the other hand, when the search region and the pattern image are set, the control section 310 determines whether a setting command for a reference plane is received (step S108).

When the setting command for the reference plane is received in step S108, the control section 310 determines whether designation of a point serving as a reference point is received on the reference image displayed on the display section 340 by the operation of the operation section 330 by the user (step S109). When the designation of the point is not received, the control section 310 proceeds to processing in the following step S111. On the other hand, when the designation of the point is received, the control section 310 instructs the control board 210 to perform the designation and measurement processing and gives a plane coordinate (Ua, Va) specified by the point designated on the image to the control board 210 (see FIG. 9A). Consequently, the control board 210 performs the designation and measurement processing (step S110) and gives a coordinate (Xc, Yc, Zc) specified by the designation and measurement processing to the control section 310. Details of the designation and measurement processing are explained below.

Thereafter, the control section 310 determines whether the designation of the point serving as the reference point is completed by the operation of the operation section 330 by the user (step S111). When the designation of the point is not completed, the control section 310 returns to the processing in step S109. On the other hand, when the designation of the point is completed, the control section 310 sets the reference plane on the basis of one or a plurality of coordinates (Xc, Yc, Zc) acquired in the designation and measurement processing in step S110 (step S112). In this example, on the basis of coordinates (Xc, Yc, Zc) corresponding to one or a plurality of reference points, information indicating coordinates of the reference plane, for example, plane coordinates (Xc, Yc) corresponding to the reference points or coordinates (Xc, Yc, Zc) corresponding to the reference points are stored in the storing section 320.

The information indicating the coordinates of the reference plane may include a reference plane constraint condition for determining the reference plane. The reference plane constraint condition includes a condition that, for example, the reference plane is parallel to a placing surface or the reference plane is parallel to another surface stored in advance. In the case of the reference plane constraint condition, when a coordinate (Xb, Yb, Zb) corresponding to one reference point is designated, a plane represented by Z=Zb is acquired as the reference plane.

After the processing in step S112 or when the setting command for the reference plane is not received in step S108, the control section 310 determines whether setting to be received is setting concerning measurement of the measurement object S (step S121). More specifically, the control section 310 determines whether the setting to be received is setting for specifying a portion of the measurement object S, the height of which should be measured.

When the measurement to be received is not the setting concerning measurement, the control section 310 acquires information concerning the setting by the operation of the operation section 330 by the user and stores the information in the storing section 320 (step S130). Examples of the information acquired in step S130 include information such as the allowable value and an indicator and a comment that should be displayed on a measurement image during the measurement mode. Thereafter, the control section 310 proceeds to processing in step S126 explained below.

When the setting received in step S121 is the setting concerning the measurement, the control section 310 determines whether designation of a point serving as a measurement point is received on the reference image displayed on the display section 340 by the operation of the operation section 330 by the user (step S122). When the designation of the point is not received, the control section 310 proceeds to processing in the following step S124. On the other hand, when the designation of the point is received, as in step S111 explained above, the control section 310 instructs the control board 210 to perform the designation and measurement processing and gives a plane coordinate (Ua, Va) specified by the designated point on the image to the control board 210. Consequently, the control board 210 performs the designation and measurement processing (step S123) and gives a coordinate (Xc, Yc, Zc) specified by the designation and measurement processing to the control section 310.

Thereafter, the control section 310 determines whether the designation of the point serving as the measurement point is completed by the operation of the operation section 330 by the user (step S124). When the designation of the point is not completed, the control section 310 returns to the processing in step S122.

On the other hand, when the designation of the point is completed, the control section 310 performs setting of the measurement point by storing, in the storing section 320, coordinates (Xc, Yc, Zc) of one or a plurality of measurement points acquired in the designation and measurement processing in step S123 (step S125).

After the processing in either one of steps S125 and S130 explained above, the control section 310 determines whether completion of the setting is instructed or new setting is instructed (step S126). When new setting is instructed, that is, when the completion of the setting is not instructed, the control section 310 returns to the processing in step S108.

On the other hand, when the completion of the setting is instructed, the control section 310 registers, as registration information, the pieces of information set in any one of steps S103 to S112, S121 to S125, and S130 explained above in association with each other (step S127). Thereafter, the optical scanning height measurement processing ends in the setting mode. A file of the registration information to be registered is saved in the storing section 320 after a specific file name is attached to the file by the user. At this point, the information temporarily stored in the storing section 320 for setting in any one of steps S103 to S112, S121 to S125, and S130 may be erased.

In step S127, when the reference plane is set by the processing in step S112 explained above, the control section 310 calculates height of the measurement point on the basis of the reference plane and the specified coordinate (Xc, Yc, Zc) and includes a result of the calculation in the registration information. Note that, when the reference plane is already set at a point in time of step S125 explained above, in step S125, height of the measurement point may be calculated on the basis of the set reference plane and the acquired coordinate (Xc, Yc, Zc). In this case, a result of the calculation may be displayed on the setting screen 350 (FIG. 27) as the height of the measurement point.

When the setting mode is not selected in step S101 explained above, the control section 310 determines whether the measurement mode is selected by the operation of the operation section 330 by the user (step S201). More specifically, the control section 310 determines whether the measurement button 341*b* shown in FIG. 8 is operated by the user. When the measurement mode is selected, the control section 310 causes the display section 340 shown in FIG. 1 to display a measurement screen 360 shown in FIG. 32 explained below (step S202). On the measurement screen 360, a measurement image in the measurement region V shown in FIG. 2 acquired at a fixed cycle by the imaging section 220 is displayed on a real-time basis.

Subsequently, the control section 310 determines whether a file of the registration information is designated by the operation of the operation section 330 by the user (step S203). Specifically, the control section 310 determines whether a filename of the registration information is designated by the user. When a file is not designated, the control section 310 stays on standby until designation of a file is received. On the other hand, when receiving designation of a file, the control section 310 reads the designated file of the registration information from the storing section 320 (step S204). Note that, when the designated file of the registration information is not stored in the storing section 320, the control section 310 may display, on the display section 340, information indicating that the designated file is absent.

Subsequently, the control section 310 acquires registered information concerning a pattern image from the read registration information and superimposes and displays the acquired pattern image on the measurement image displayed on the display section 340 (step S205). At this point, the control section 310 acquires a search region in addition to the pattern image. Note that, as explained above, the information concerning the pattern image also includes information indicating a position of the pattern image in the reference image. Therefore, the pattern image is superimposed and displayed on the measurement image in the same position as the position set in the setting mode.

The pattern image may be displayed semitransparent. In this case, the user can easily compare a currently captured measurement image of the measurement object S and the reference image of the measurement object S acquired during the setting mode. Then, the user can perform work for positioning the measurement object S on the optical surface plate 111.

Subsequently, the control section 310 performs comparison of the pattern image and the measurement image (step S206). Specifically, the control section 310 extracts, as a reference edge, an edge of the measurement object S in the pattern image and searches whether an edge having a shape corresponding to the reference edge is present in the acquired search region.

In this case, an edge portion of the measurement object S in the measurement image is considered to be most similar to the reference edge. When a portion of the measurement image most similar to the reference edge is detected, the control section 310 calculates how much the detected portion deviates from the reference edge on the image and calculates how much the detected portion rotates from the reference edge on the image (step S207).

Subsequently, the control section 310 acquires information concerning a registered measurement point from the read registration information and corrects the acquired information concerning the measurement point on the basis of a calculated deviation amount and a calculated rotation amount (step S208). The processing in steps S206 to S208 is equivalent to the function of the correcting section 17 shown in FIG. 10. With this configuration, even when a measurement object in a corrected image is displaced or rotated with respect to the measurement object in the pattern image, it is possible to highly accurately and easily specify and correct a measurement point.

Subsequently, the control section 310 instructs the control board 210 to perform actual measurement processing for each of corrected measurement points and gives coordinates (Xc, Yc, Zc) of the corrected measurement points to the control board 210 (see FIG. 9B). Consequently, the control board 210 performs the actual measurement processing (step S209) and gives a coordinate (Xb, Yb, Zb) specified by the actual measurement processing to the control section 310. Details of the actual measurement processing are explained below.

Subsequently, the control section 310 acquires registered information concerning a reference plane, calculates height of a measurement point on the basis of the reference plane and the acquired coordinate (Xb, Yb, Zb), and stores a result of the calculation in the storing section 320 as a measurement result. The control section 310 performs various kinds of processing corresponding to registered other kinds of information (step S210). As the various kinds of information corresponding to the registered other kinds of information, for example, when an allowable value is included in read registration information, inspection processing for determining whether the calculation result of the height is within a range of a tolerance set by the allowable value may be performed. Thereafter, the optical scanning height measurement processing ends in the measurement mode.

When the measurement mode is not selected in step S201 explained above, the control section 310 determines whether the height gauge mode is selected by the operation of the operation section 330 by the user (step S211). More specifically, the control section 310 determines whether the height gauge button 341*c* shown in FIG. 8 is operated by the user. When the height gauge mode is not selected, the control section 310 returns to the processing in step S101.

Figure 25:
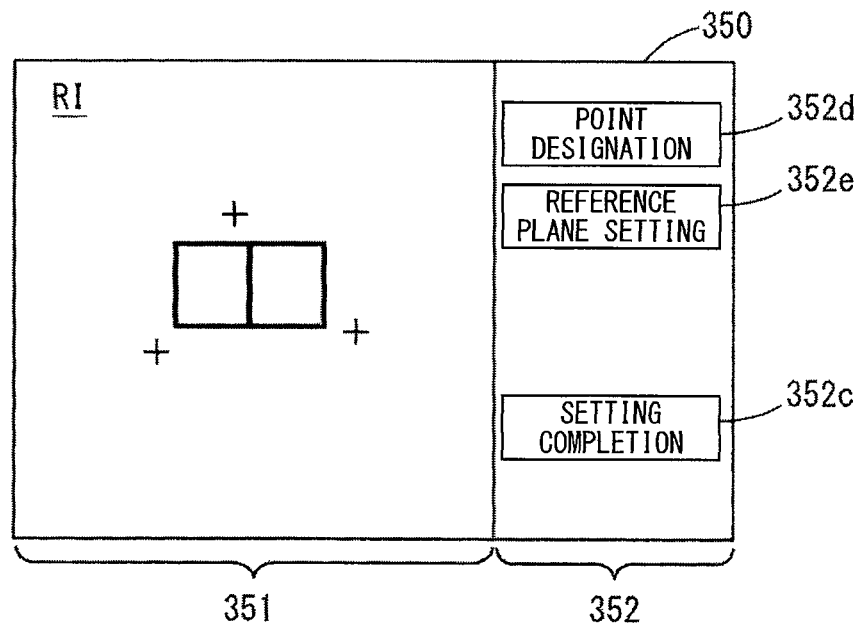
FIG. 25 is a diagram for explaining the operation example of the optical-scanning-height measuring device in the setting mode.
Figure 26:
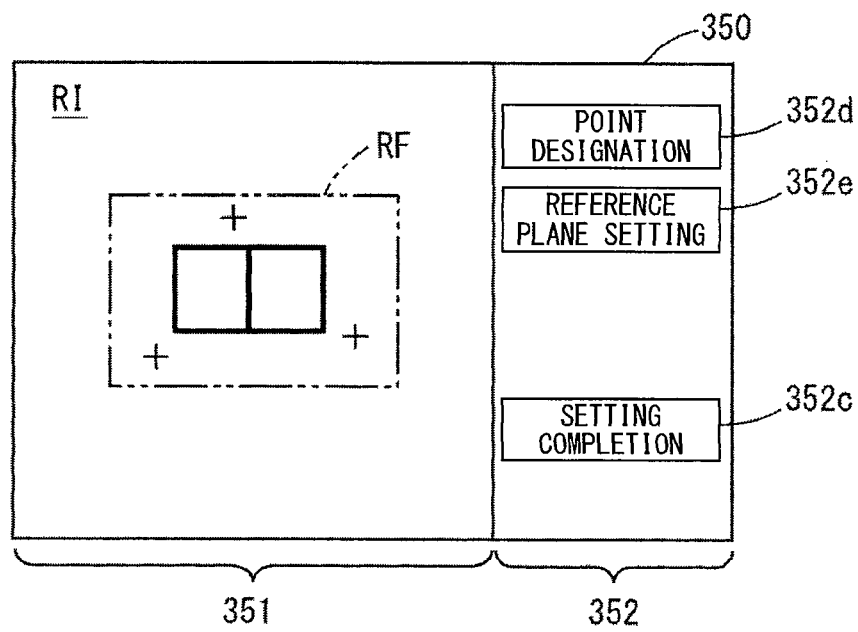
FIG. 26 is a diagram for explaining the operation example of the optical-scanning-height measuring device in the setting mode.

On the other hand, when the height gauge mode is selected, the control section 310 causes the display section 340 shown in FIG. 1 to display the setting screen 350 shown in FIG. 25 explained below (step S212). Thereafter, the control section 310 performs setting of a reference plane on the basis of the operation of the operation section 330 by the user (step S213). This setting processing is the same as the processing in steps S109 to S112 explained above.

Thereafter, when receiving designation of a point, the control section 310 instructs the control board 210 to perform the designation and measurement processing and gives a plane coordinate (Ua, Va) specified by a point designated on the image to the control board 210 (see FIG. 9C). Consequently, the control board 210 performs the designation and measurement processing (step S214). The control board 210 adjusts the positions of the movable sections 252a and 252b shown in FIG. 5 and the angles of the reflecting sections 271b and 272b shown in FIG. 7 on the basis of the coordinate (Xc, Yc, Zc) specified by the designation and measurement processing and the position conversion information and irradiates measurement light (step S215).

Subsequently, the control board 210 calculates, on the basis of the light reception signal output from the light receiving section 232d shown in FIG. 4, the positions of the movable sections 252a and 252b shown in FIG. 5, and the deflecting directions of the deflecting sections 271 and 272 shown in FIG. 7, a three-dimensional coordinate (Xb, Yb, Zb) of a portion on which the measurement light is irradiated on the measurement object S and gives the three-dimensional coordinate (Xb, Yb, Zb) to the control section 310 (step S216).

Note that, in step S216 explained above, the control board 210 may calculate, on the basis of the light reception signal output from the light receiving section 232d shown in FIG. 4, the positions of the movable sections 252a and 252b shown in FIG. 5, and the plane coordinate indicating the irradiation position of the measurement light on the image acquired by the imaging section 220 shown in FIG. 1, the three-dimensional coordinate (Xb, Yb, Zb) of the portion on which the measurement light is irradiated on the measurement object S.

Subsequently, the control section 310 acquires information concerning the set reference plane, calculates, on the basis of the reference plane and the acquired coordinate (Xb, Yb, Zb), height of the portion on which the measurement light is irradiated on the measurement object S, and displays a result of the calculation on the display section 340 as a measurement result. For example, when the reference plane is a plane, the control section 310 calculates, as height, the length of a perpendicular of the reference plane, which passes the acquired coordinate (Xb, Yb, Zb), from the reference plane to the coordinate (Xb, Yb, Zb) at the time when the perpendicular is drawn and displays a result of the calculation on the display section 340 as a measurement result. The control section 310 displays, on the display section 340, a green "+" mark, which indicates that the height of the portion of the measurement object S corresponding to the measurement point can be calculated, in a plane coordinate indicating the irradiation position of the measurement light on the image acquired by the imaging section 220 or a plane coordinate specified by the point designated on the image (step S217).

Subsequently, the control section 310 determines whether an additional point is designated by the operation of the operation section 330 by the user (step S218). When an additional point is designated, the control section 310 returns to the processing in step S214. Consequently, the processing in steps S214 to S218 is repeated until no additional point is designated. When an additional point is not designated, the optical scanning height measurement processing ends in the height gauge mode.

With the height gauge mode explained above, the user can designate a reference point and a reference plane by designating a point on an image. The user can acquire a measurement result of height by designating a measurement point on a screen. Further, the user can continue the measurement while continuously maintaining the reference plane by designating a plurality of measurement points.

(9) An Example of the Designation and Measurement Processing

Figure 16:
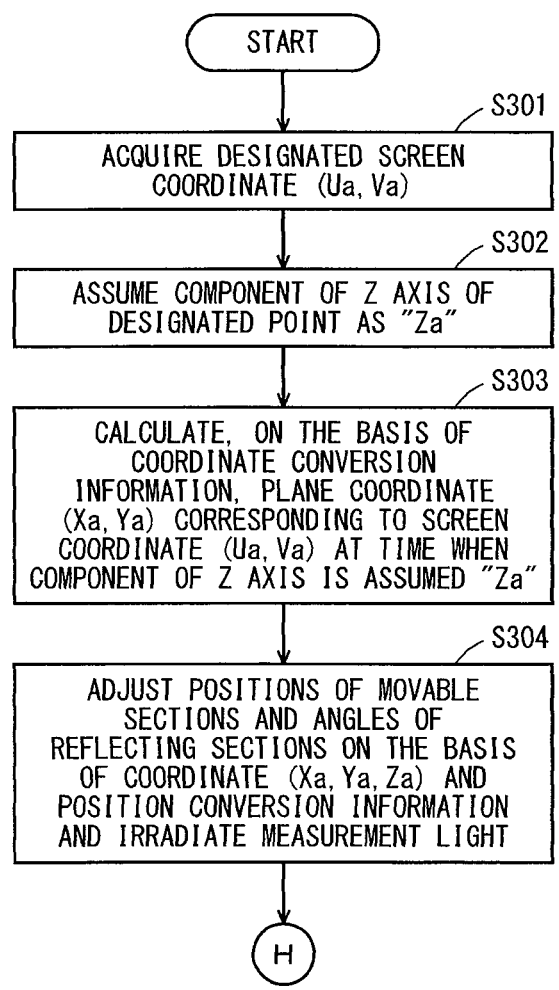
FIG. 16 is a flowchart for explaining an example of designation and measurement processing by the control board.
Figure 17:
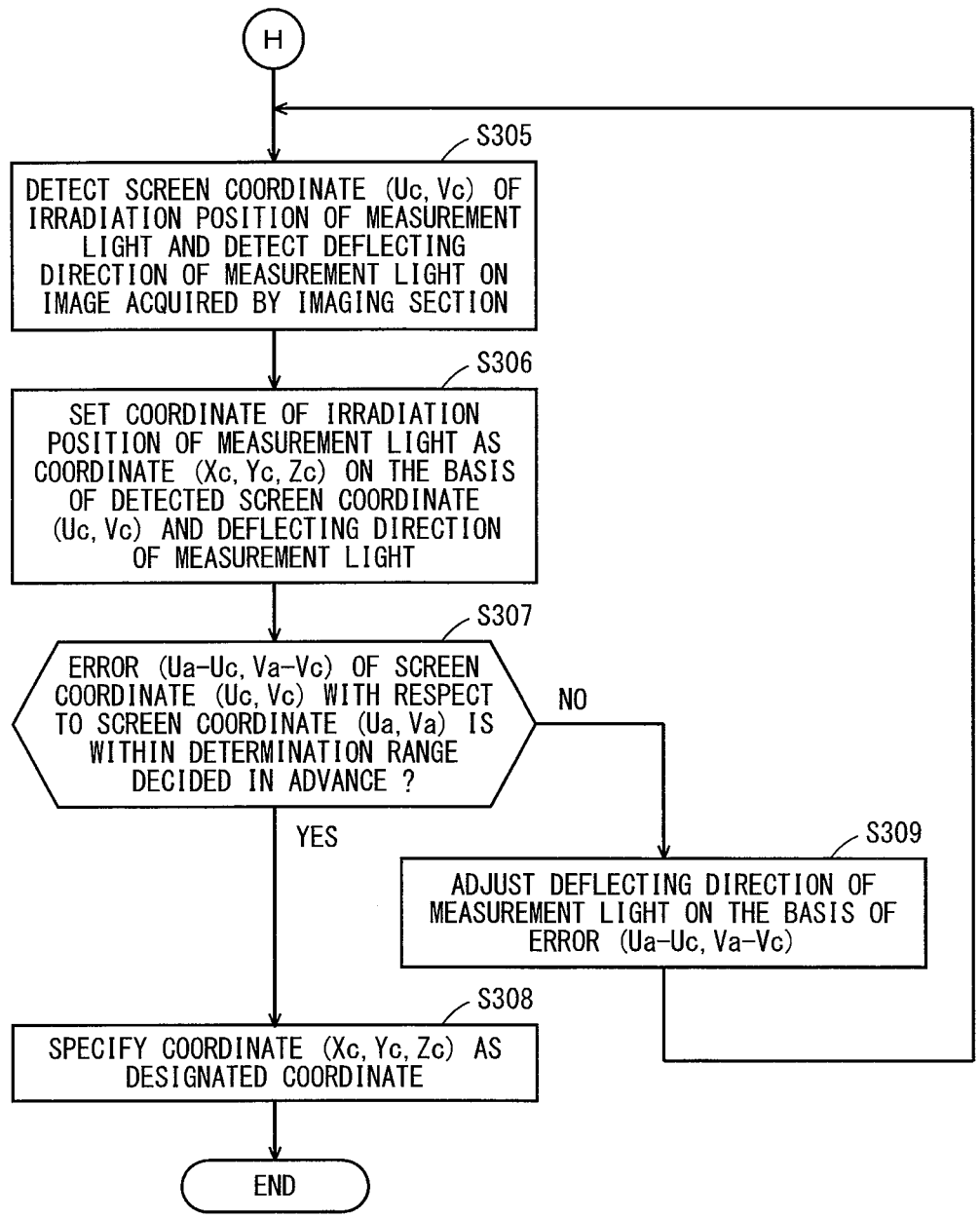
FIG. 17 is a flowchart for explaining the example of the designation and measurement processing by the control board.

FIGS. 16 and 17 are flowcharts for explaining an example of the designation and measurement processing by the control board 210. FIGS. 18A to 19B are explanatory diagrams for explaining the designation and measurement processing shown in FIGS. 16 and 17. In each of FIGS. 18A to 18C and FIGS. 19A and 19B, on the left side, a positional relation between the measurement object S placed on the optical surface plate 111 and the imaging section 220 and the scanning section 270 is shown as a side view and, on the right side, an image displayed on the display section 340 by imaging of the imaging section 220 is shown. The image displayed on the display section 340 includes an image SI of the measurement object S. In the following explanation, a plane coordinate on the image displayed on the display section 340 is referred to as screen coordinate.

The control board 210 starts the designation and measurement processing by receiving a command for the designation and measurement processing from the control section 310. Therefore, the control board 210 acquires a screen coordinate (Ua, Va) given from the control section 310 together with the command (step S301).

Figure 18A:
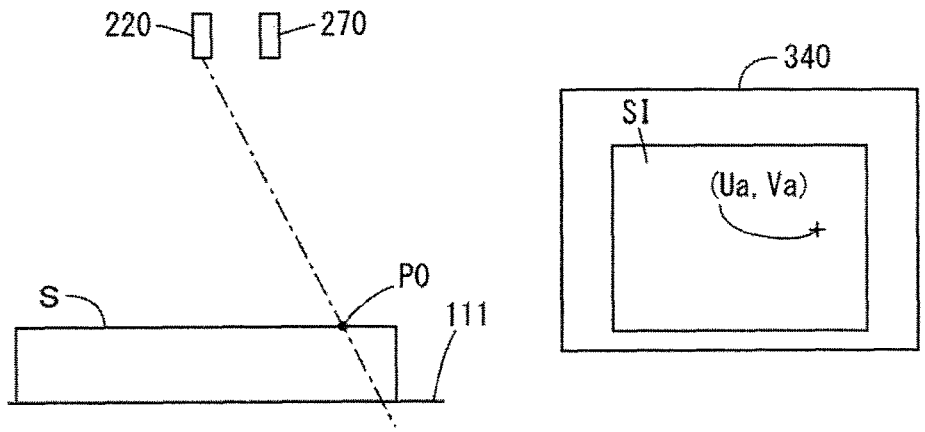
FIGS. 18A to 18C are explanatory diagrams for explaining the designation and measurement processing shown in FIGS. 16 and 17.

On the right side of FIG. 18A, the screen coordinate (Ua, Va) is shown on the image displayed on the display section 340. On the left side of FIG. 18A, a portion of the measurement object S corresponding to the screen coordinate (Ua, Va) is indicated by a point P0.

Figure 18B:
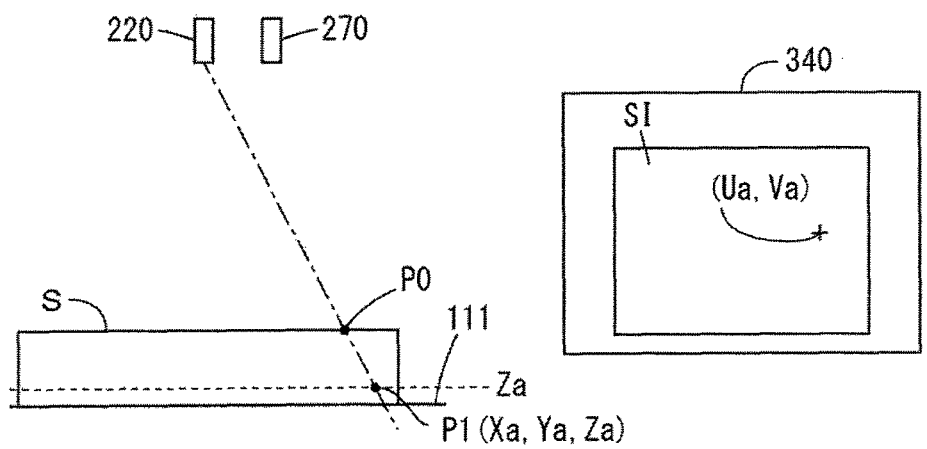

In step S301, a component of the Z axis (a component in the height direction) in a coordinate of the point P0 corresponding to the screen coordinate (Ua, Va) is unknown. Therefore, the control board 210 assumes the component of the Z axis of the point P0 designated by the user as "Za" (step S302). In this case, as shown in FIG. 18B, the assumed component of the Z axis does not always coincide with a component of the Z axis of an actually designated point P0.

Subsequently, the control board 210 calculates, on the basis of the coordinate conversion information explained above, a plane coordinate (Xa, Ya) corresponding to the screen coordinate (Ua, Va) at the time when the component of the Z axis is the assumed "Za" (step S303). Consequently, as shown in FIG. 18B, a coordinate (Xa, Ya, Za) of an imaginary point P1 corresponding to the screen coordinate (Ua, Va) and the assumed component of the Z axis is obtained. Note that, in this example, it is assumed that "Za" is an intermediate position in the Z direction in the measurement region V shown in FIG. 2.

Subsequently, the control board 210 adjusts the positions of the movable sections 252a and 252b shown in FIG. 5 and the angles of the reflecting sections 271b and 272b shown in FIG. 7 on the basis of the coordinate (Xa, Ya, Za) obtained by processing in step S303 and the position conversion information and irradiates the measurement light (step S304).

Figure 18C:
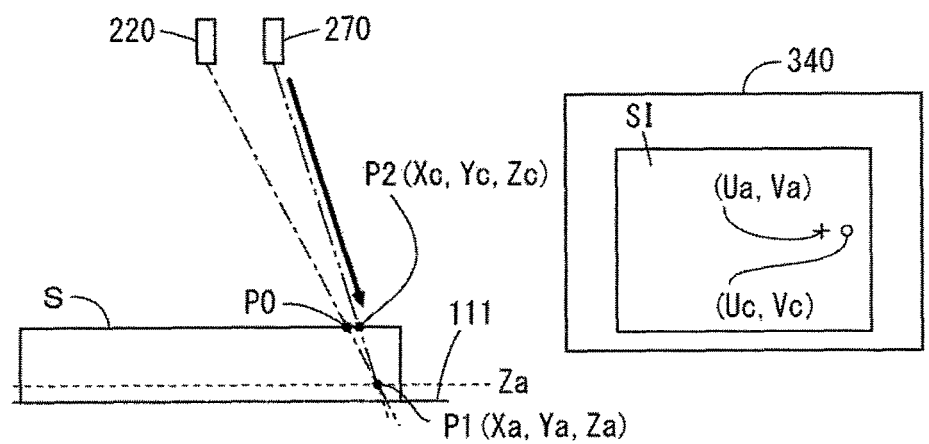

In this case, when the component of the Z axis assumed in step S302 greatly deviates from a component of the Z axis of the actually designated point P0, as shown in the side view on the left side of FIG. 18C, an irradiation position of the measurement light on the measurement object S greatly deviates from the actually designated point P0. Therefore, processing explained below is performed.

According to processing in step S304, an irradiation portion (a light spot) of the measurement light irradiated on the measurement object S from the scanning section 270 appears on the image acquired by the imaging section 220. In this case, it is possible to easily detect a screen coordinate of the irradiation portion of the measurement light using image processing and the like. In the figure on the right side of FIG. 18C, an irradiation portion (a light spot) of the measurement light appearing on an image displayed on the display section 340 is indicated by a circle.

After the processing in step S304, the control board 210 detects, as a screen coordinate (Uc, Vc), a plane coordinate indicating an irradiation position of the measurement light on the image acquired by the imaging section 220 and detects a deflecting direction of the measurement light from the angles of the reflecting sections 271b and 272b shown in FIG. 7 (step S305).

Subsequently, the control board 210 sets, as a coordinate (Xc, Yc, Zc), a coordinate of an irradiation position P2 of the measurement light on the measurement object S or the optical surface plate 111 on the basis of the detected screen coordinate (Uc, Vc) and the deflecting direction (step S306).

As shown in FIG. 18C, when the irradiation position P2 deviates from the point P0, the screen coordinate (Uc, Vc) deviates from the screen coordinate (Ua, Va). Therefore, the control board 210 calculates an error (Ua−Uc, Va−Vc) of the detected screen coordinate (Uc, Vc) with respect to the screen coordinate (Ua, Va) and determines whether the calculated error is within a determination range decided in advance (step S307). The determination range used at this point may be able to be set by the user or may be set in advance during factory shipment of the optical-scanning-height measuring device 400.

When, in step S307, the error (Ua−Uc, Va−Vc) is within the determination range decided in advance, the control board 210 specifies, as a coordinate designated by the user, the coordinate (Xc, Yc, Zc) decided in the immediately preceding step S306 (step S308) and ends the designation and measurement processing. Thereafter, the control board 210 gives the specified coordinate (Xc, Yc, Zc) to the control section 310.

When, in step S307, the error (Ua−Uc, Va−Vc) is outside the determination range decided in advance, the control board 210 adjusts the deflecting direction of the measurement light on the basis of the error (Ua−Uc, Va−Vc) (step S309). Specifically, for example, a relation between errors on screen coordinates corresponding to the X axis and the Y axis and angles of the reflecting sections 271b and 272b that should be adjusted is stored in the storing section 320 in advance as an error correspondence relation. Then, as indicated by a white arrow in FIG. 19A, the control board 210 finely adjusts the deflecting direction of the measurement light on the basis of the calculated error (Ua−Uc, Va−Vc) and the error correspondence relation.

Figure 19A:
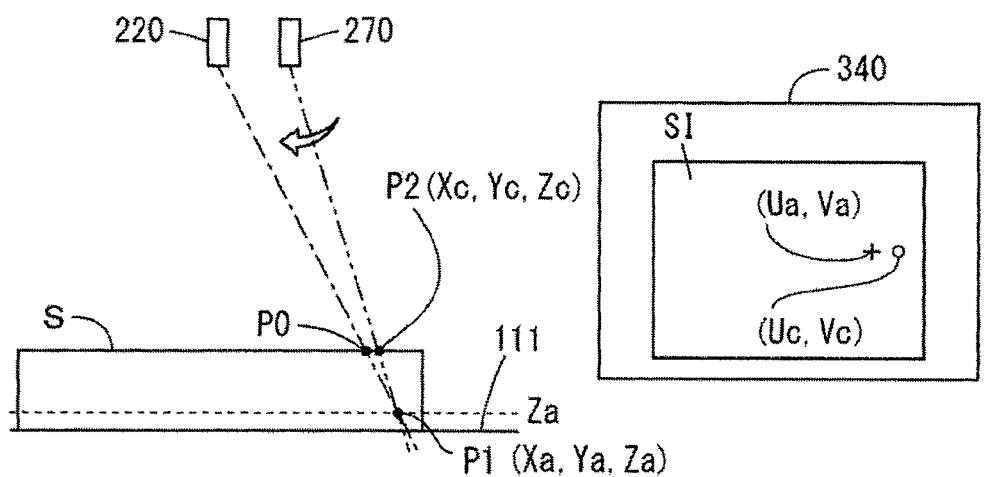
FIGS. 19A and 19B are explanatory diagrams for explaining the designation and measurement processing shown in FIGS. 16 and 17.
Figure 19B:
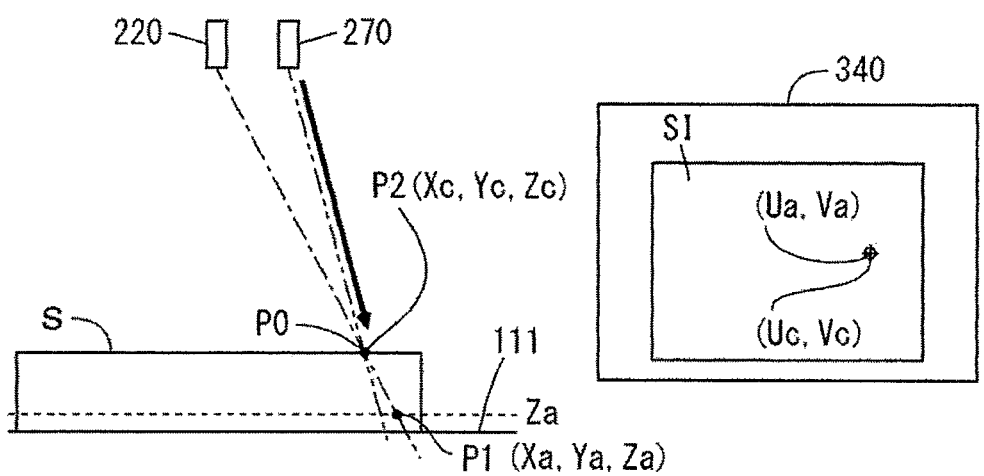

Thereafter, the control board 210 returns to the processing in step S305. Consequently, after the deflecting direction of the measurement light is finely adjusted, the processing in steps S305 to S307 is performed again. As a result, finally, as shown in FIG. 19B, the error (Ua−Uc, Va−Vc) is within the determination range. Consequently, a coordinate (Xc, Yc, Zc) corresponding to the measurement point designated by the user is specified.

In this example, the coordinate of the irradiation position P2 is calculated as the coordinate (Xc, Yc, Zc) by the processing in step S306. However, the present invention is not limited to this. The coordinate of the irradiation position P2 may be calculated as the coordinate (Xc, Yc, Zc) by processing in steps S405 and S406 in the designation and measurement processing shown in FIGS. 20 and 21 explained below.

(10) Another Example of the Designation and Measurement Processing

Figure 20:
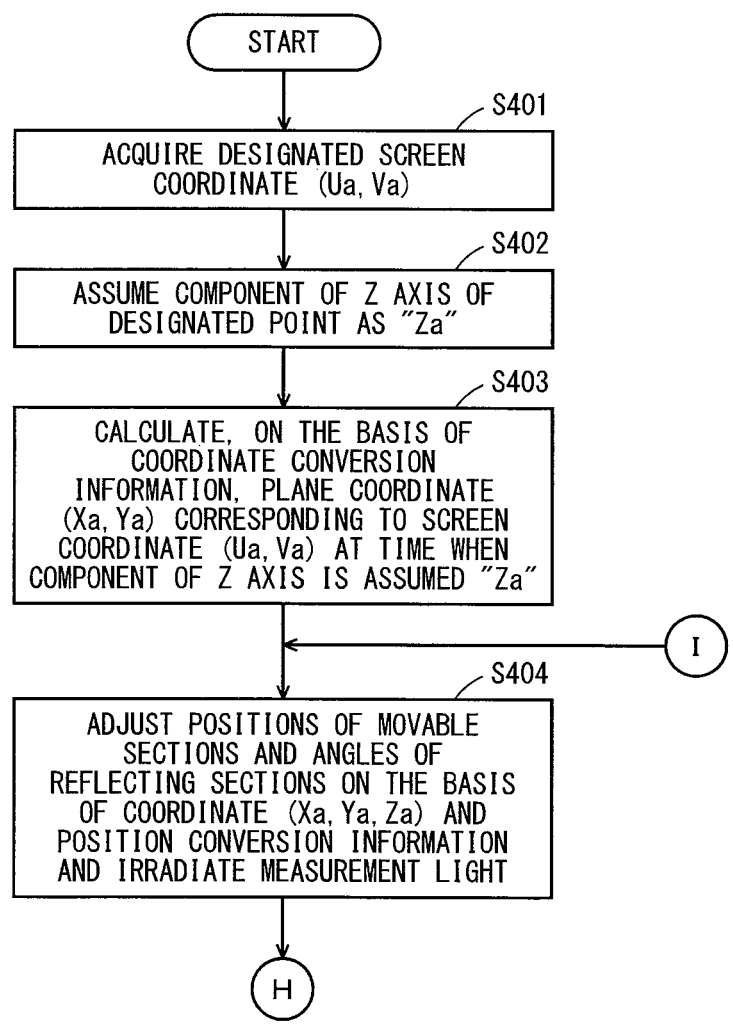
FIG. 20 is a flowchart for explaining another example of the designation and measurement processing by the control board.
Figure 21:
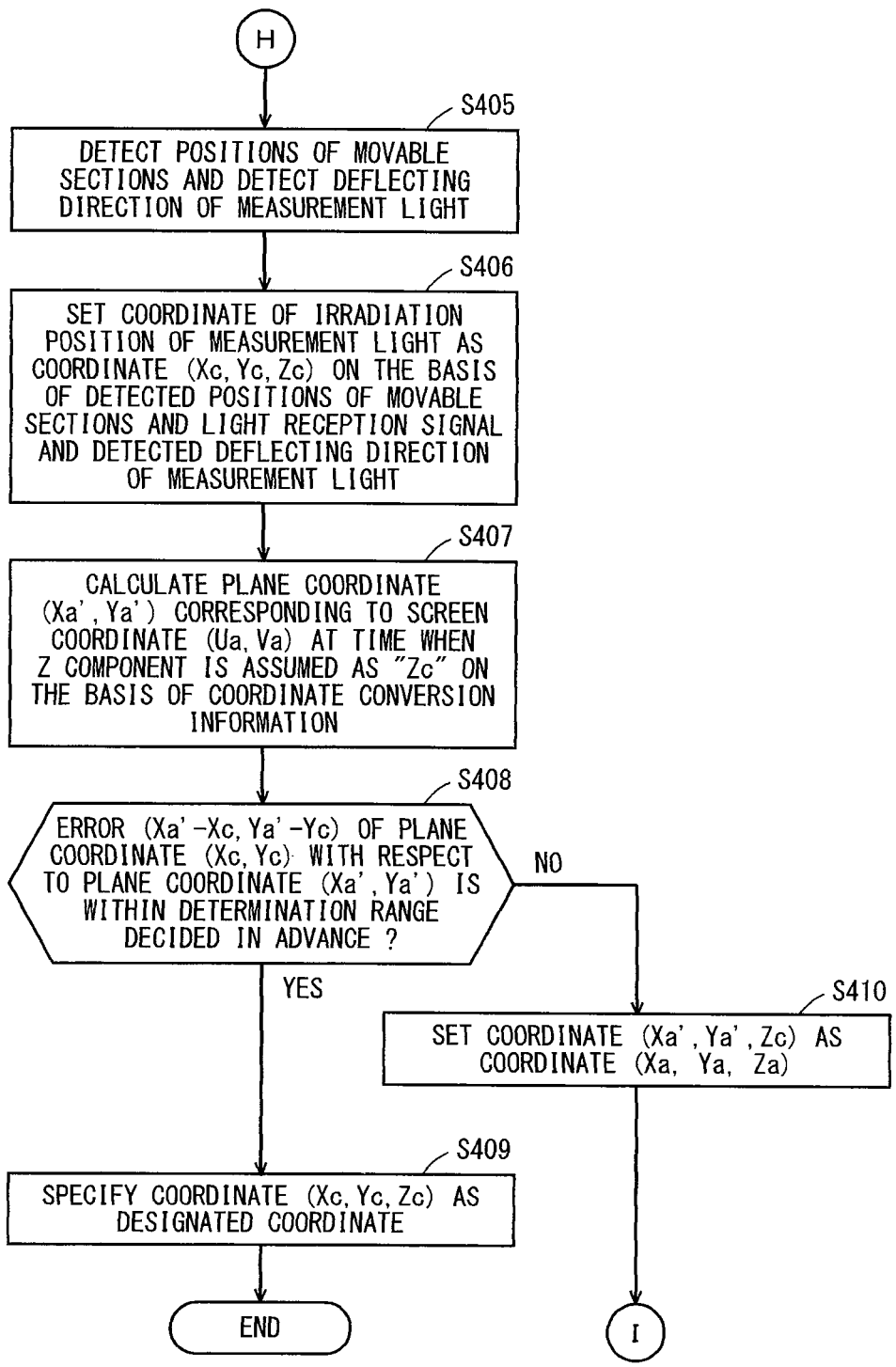
FIG. 21 is a flowchart for explaining the other example of the designation and measurement processing by the control board.
Figure 22A:
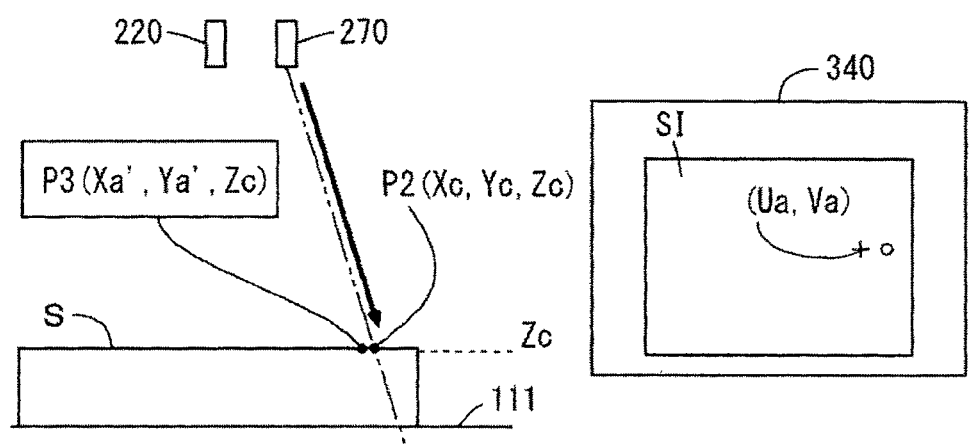
FIGS. 22A and 22B are explanatory diagrams for explaining the designation and measurement processing shown in FIGS. 20 and 21.
Figure 22B:
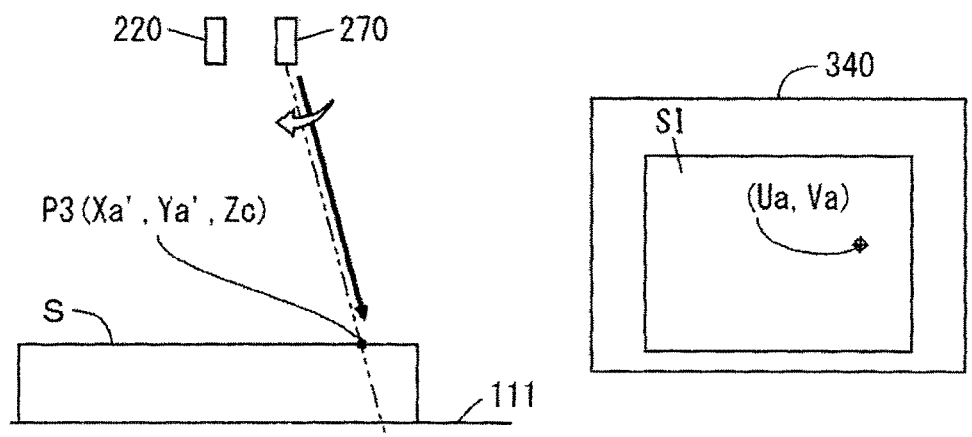

FIGS. 20 and 21 are flowcharts for explaining another example of the designation and measurement processing by the control board 210. FIGS. 22A and 22B are explanatory diagrams for explaining the designation and measurement processing shown in FIGS. 20 and 21. In each of FIGS. 22A and 22B, on the left side, a positional relation between the measurement object S placed on the optical surface plate 111 and the imaging section 220 and the scanning section 270 is shown as a side view and, on the right side, an image displayed on the display section 340 by imaging of the imaging section 220 is shown.

When the designation and measurement processing is started, the control board 210 acquires a screen coordinate (Ua, Va) given from the control section 310 together with a command (step S401). Subsequently, as in the processing in step S302 explained above, the control board 210 assumes a component of the Z axis of the point P0 designated by the user as "Za" (step S402). In this case, as in the example shown in FIG. 18B, the assumed component of the Z axis does not always coincide with a component of the Z axis of the actually designated point P0.

Subsequently, as in the processing in step S303 explained above, the control board 210 calculates a plane coordinate (Xa, Ya) corresponding to a screen coordinate (Ua, Va) at the time when the assumed component of the Z axis is "Za" (step S403). As in the processing in step S304 explained above, the control board 210 adjusts the positions of the movable sections 252a and 252b shown in FIG. 5 and the angles of the reflecting sections 271b and 272b shown in FIG. 7 on the basis of a coordinate (Xa, Ya, Za) of the imaginary point P1 obtained by the processing in step S403 and the position conversion information and irradiates the measurement light (step S404). In step S404, a relation between the point P0 designated by the user and an irradiation position of the measurement light irradiated on the measurement object S is the same as the relation shown in FIG. 18C. Thereafter, the following processing is performed such that the irradiation position of the measurement light on the measurement object S coincides with or is close to the actually designated point P0.

First, the control board 210 detects the positions of the movable sections 252a and 252b shown in FIG. 5 and detects a deflecting direction of the measurement light from the angles of the reflecting sections 271b and 272b shown in FIG. 7 (step S405).

Subsequently, the control board 210 calculates a distance between the emitting position of the measurement light (the position of the port 245d of the light guide section 240) and the irradiation position of the measurement light in the measurement object S on the basis of the positions of the movable sections 252a and 252b detected in the immediately preceding step S405 and the light reception signal acquired by the light receiving section 232d shown in FIG. 4. The control board 210 sets, as a coordinate (Xc, Yc, Zc), a coordinate of the irradiation position P2 of the measurement light on the measurement object S or the optical surface plate 111 on the basis of the calculated distance and the deflecting direction of the measurement light detected in the immediately preceding step S405 (step S406).

According to the processing in step S406 explained above, it is estimated that the component "Zc" of the Z axis of the irradiation position P2 of the measurement light is a value coinciding with or close to the component of the Z axis of the point P0 designated by the user. Therefore, the control board 210 calculates, on the basis of the coordinate conversion information, a plane coordinate (Xa', Ya') corresponding to a screen coordinate (Ua, Va) at the time when the component of the Z axis is the assumed "Zc" (step S407). Consequently, as shown in FIG. 22A, a coordinate (Xa', Ya', Za') of an imaginary point P3 corresponding to the screen coordinate (Ua, Va) and the assumed component of the Z axis is obtained.

Subsequently, the control board 210 calculates an error (Xa'−Xc, Ya'−Yc) of the plane coordinate (Xc, Yc) of the irradiation position P2 with respect to the plane coordinate (Xa', Ya') of the imaginary point P3 and determines whether the calculated error is within a determination range decided in advance (step S408). The determination range used at this point may be able to be set by the user or may be set in advance during factory shipment of the optical-scanning-height measuring device 400.

When, in step S408, the error (Xa'−Xc, Ya'−Yc) is within the determination range decided in advance, the control board 210 specifies, as a coordinate designated by the user, the coordinate (Xc, Yc, Zc) of the irradiation position P2 decided in the immediately preceding step S406 (step S409) and ends the designation and measurement processing. Thereafter, the control board 210 gives the specified coordinate (Xc, Yc, Zc) to the control section 310.

When, in step S408, the error (Xa'−Xc, Ya'−Yc) is outside the determination range decided in advance, the control board 210 sets, as the coordinate (Xa, Ya, Za) set as an irradiation target of the measurement light in step S404 explained above, the coordinate (Xa', Ya', Za') of the imaginary point P3 obtained in the immediately preceding step S407 (step S410). Thereafter, the control board 210 returns to the processing in step S404.

Consequently, after the deflecting direction of the measurement light is changed, the processing in steps S404 to S408 is performed again. As a result, finally, as shown in FIG. 22B, since the error (Xa'−Xc, Ya'−Yc) is within the determination range, a coordinate (Xc, Yc, Zc) corresponding to the measurement point designated by the user is specified.

In this example, the coordinate of the irradiation position P2 is calculated as the coordinate (Xc, Yc, Zc) by the processing in steps S405 and S406. However, the present invention is not limited to this. The coordinate of the irradiation position P2 may be calculated as the coordinate (Xc, Yc, Zc) by processing in step S306 in the designation and measurement processing shown in FIGS. 16 and 17.

(11) The Actual Measurement Processing

The control board 210 receives a command for the actual measurement processing from the control section 310 to thereby start the actual measurement processing. When the actual measurement processing is started, first, the control board 210 acquires a coordinate (Xc, Yc, Zc) of the measurement point given from the control section 310 together with the command.

Even if the measurement light is irradiated on the basis of the coordinate (Xc, Yc, Zc) of the measurement point set in the setting mode and the position conversion information, a plane coordinate of an irradiation position of the measurement light on the measurement object S greatly deviates from the coordinate of the measurement point depending on a shape of the measurement object S measured in the measurement mode.

For example, when a component of the Z axis of the portion of the measurement object S corresponding to the measurement point greatly deviates from "Zc", the plane coordinate of the irradiation position of the measurement light greatly deviates from the set plane coordinate (Xc, Yc) of the measurement point. Therefore, in the actual measurement processing, the plane coordinate of the irradiation position of the measurement light is adjusted to fit within a fixed range from the plane coordinate (Xc, Yc) of the measurement point.

Specifically, for example, after setting a screen coordinate corresponding to the acquired coordinate (Xc, Yc, Zc) of the measurement point as (Ua, Va), the control board 210 sets the acquired coordinate (Xc, Yc, Zc) of the measurement point as the coordinate (Xa, Ya, Za) of the imaginary point P1 obtained in the processing in step S303 in FIG. 16. Subsequently, the control board 210 performs steps S304 to S308 in FIGS. 16 and 17. Subsequently, the control board 210 adjusts the positions of the movable sections 252a and 252b shown in FIG. 5 and the angles of the reflecting sections 271b and 272b shown in FIG. 7 on the basis of the coordinate (Xc, Yc, Zc) specified in the processing in step S308 and the position conversion information and irradiates the measurement light.

Thereafter, the control board 210 calculates, on the basis of the light reception signal output from the light receiving section 232d shown in FIG. 4, the positions of the movable sections 252a and 252b shown in FIG. 5, and the deflecting directions of the deflecting sections 271 and 272 shown in FIG. 7, a three-dimensional coordinate (Xb, Yb, Zb) of a portion on which the measurement light is irradiated on the measurement object S and gives the three-dimensional coordinate (Xb, Yb, Zb) to the control section 310. Consequently, the actual measurement processing ends. Note that the control board 210 may calculate, on the basis of the light reception signal output from the light receiving section 232d shown in FIG. 4, the positions of the movable sections 252a and 252b shown in FIG. 5, and the plane coordinate indicating the irradiation position of the measurement light on the image acquired by the imaging section 220 shown in FIG. 1, the three-dimensional coordinate (Xb, Yb, Zb) of the portion on which the measurement light is irradiated on the measurement object S.

Alternatively, the control board 210 may execute the actual measurement processing as explained below. For example, after setting a screen coordinate corresponding to the acquired coordinate (Xc, Yc, Zc) of the measurement point to (Ua, Va), the control board 210 sets the acquired coordinate (Xc, Yc, Zc) of the measurement point as the coordinate (Xa, Ya, Za) of the imaginary point P1 obtained in the processing in step S403 in FIG. 20. Subsequently, the control board 210 performs processing in steps S404 to S409 shown in FIGS. 20 and 21. Subsequently, the control board 210 adjusts the positions of the movable sections 252a and 252b shown in FIG. 5 and the angles of the reflecting sections 271b and 272b shown in FIG. 7 on the basis of the coordinate (Xc, Yc, Zc) specified in the processing in step S408 and the position conversion information and irradiates the measurement light.

Thereafter, as in the example explained above, the control board 210 calculates, on the basis of the light reception signal output from the light receiving section 232d shown in FIG. 4, the positions of the movable sections 252a and 252b shown in FIG. 5, and the deflecting directions of the deflecting sections 271 and 272 shown in FIG. 7, a three-dimensional coordinate (Xb, Yb, Zb) of the portion on which the measurement light is irradiated on the measurement object S and gives the three-dimensional coordinate (Xb, Yb, Zb) to the control section 310. Alternatively, the control board 210 calculates, on the basis of the light reception signal output from the light receiving section 232d shown in FIG. 4, the positions of the movable sections 252a and 252b shown in FIG. 5, and the plane coordinate indicating the irradiation position of the measurement light on the image acquired by the imaging section 220 shown in FIG. 1, the three-dimensional coordinate (Xb, Yb, Zb) of the portion on which the measurement light is irradiated on the measurement object S and gives the three-dimensional coordinate (Xb, Yb, Zb) to the control section 310.

(12) An Operation Example in which the Setting Mode and the Measurement Mode are Used FIGS. 23 to 28 are diagrams for explaining an operation example of the optical-scanning-height measuring device 400 in the setting mode. In the following explanation, the users of the optical-scanning-height measuring device 400 are distinguished as the measurement manager and the measurement operator and explained.

Figure 23:
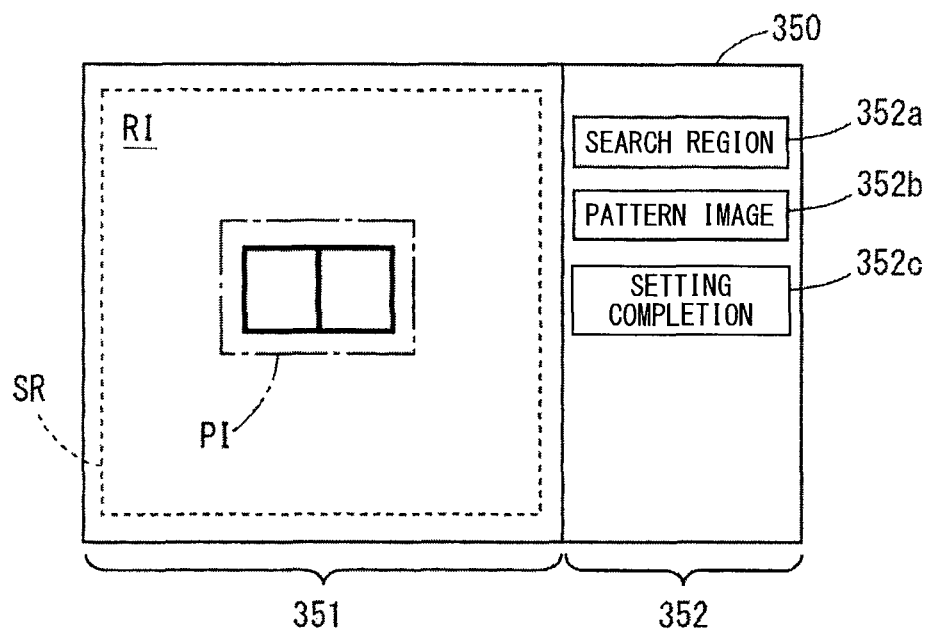
FIG. 23 is a diagram for explaining an operation example of the optical-scanning-height measuring device in a setting mode.

First, the measurement manager positions the measurement object S, which serves as a reference of height measurement, on the optical surface plate 111 and operates the setting button 341a shown in FIG. 8 using the operation section 330 shown in FIG. 1. Consequently, the optical-scanning-height measuring device 400 starts the operation in the setting mode. In this case, for example, as shown in FIG. 23, the setting screen 350 is displayed on the display section 340 shown in FIG. 1. The setting screen 350 includes an image display region 351 and a button display region 352. In the image display region 351, a currently captured image of the measurement object S is displayed in the image display region 351 as a reference image RI. In the diagrams of FIGS. 23 to 28 and the diagrams of FIGS. 29 to 34 referred to below, a contour indicating a shape of the measurement object S in the reference image RI and a measurement image MI explained below displayed in the image display region 351 is indicated by a thick solid line.

At a start point in time of the setting mode, in the button display region 352, a search region button 352a, a pattern image button 352b, and a setting completion button 352c are displayed. The measurement manager operates, for example, the search region button 352a to perform drag operation or the like on the image display region 351. Consequently, the measurement manager sets a search region SR as indicated by a dotted line in FIG. 23. The measurement manager operates, for example, the pattern image button 352b to perform the drag operation or the like on the image display region 351. Consequently, it is possible to set a pattern image PI as indicated by an alternate long and short dash line in FIG. 23.

Figure 24:
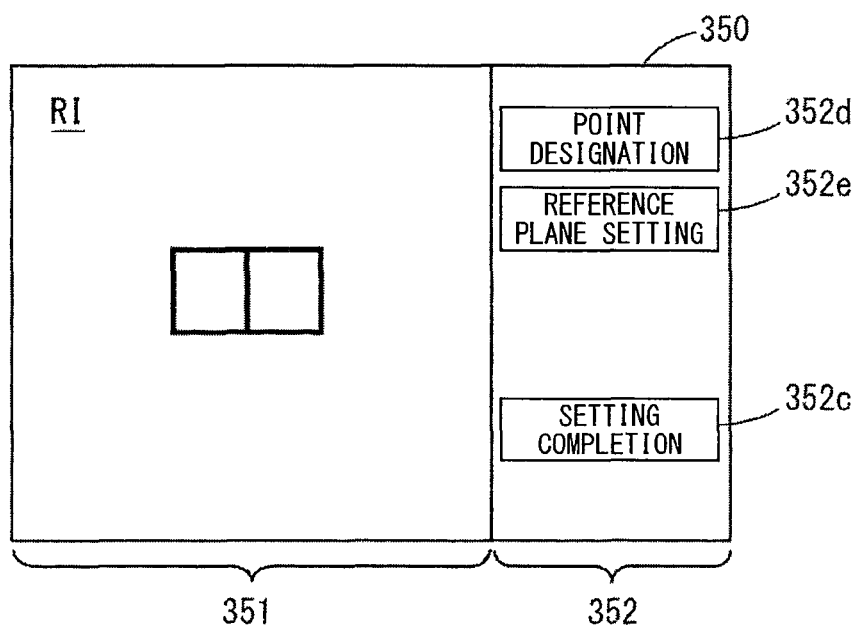
FIG. 24 is a diagram for explaining the operation example of the optical-scanning-height measuring device in the setting mode.

After setting the search region SR and the pattern image PI, the measurement manager operates the setting completion button 352c. Consequently, the setting of the search region SR and the pattern image PI is completed. A display form of the setting screen 350 is switched as shown in FIG. 24. Specifically, in the image display region 351, indicators indicating the set search region SR and the set pattern image PI are removed. In the button display region 352, a point designation button 352d and a reference plane setting button 352e are displayed instead of the search region button 352a and the pattern image button 352b shown in FIG. 23.

The measurement manager operates the point designation button 352d to perform, for example, click operation on the image display region 351. Consequently, one or a plurality of (in this example, three) reference points are designated as indicated by "+" marks in FIG. 25. Thereafter, the measurement manager operates the reference plane setting button 352e. Consequently, a reference plane including the designated one or plurality of reference points is set. As indicated by an alternate long and two short dashes line in FIG. 26, an indicator indicating a reference plane RF set in the image display region 351 is displayed. When four or more reference points are designated, all of the four or more reference points are not always included in the reference plane RF. In this case, the reference plane RF is set such that, for example, distances among the plurality of reference points are small as a whole. Similarly, when a reference plane constraint condition for determining a reference plane is decided, for example, when a condition that, for example, the reference plane is parallel to a placing surface or the reference plane is parallel to other surfaces stored in advance, is decided, when two or more reference points are designated, all of the two or more reference points do not always need to be included in the reference plane RF. Note that a plurality of reference planes RF may be set by repeating the operation of the point designation button 352d and the reference plane setting button 352e.

Figure 27:
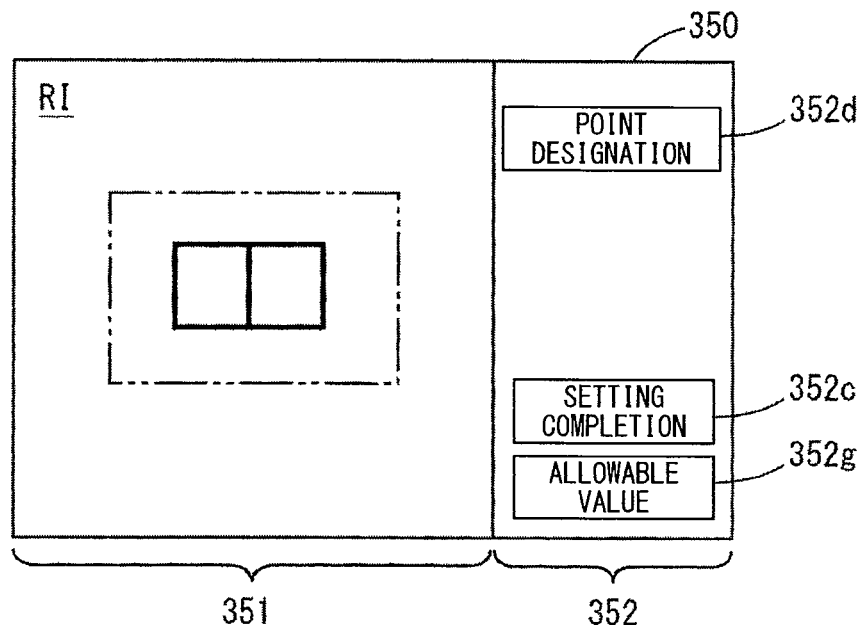
FIG. 27 is a diagram for explaining the operation example of the optical-scanning-height measuring device in the setting mode.
Figure 28:
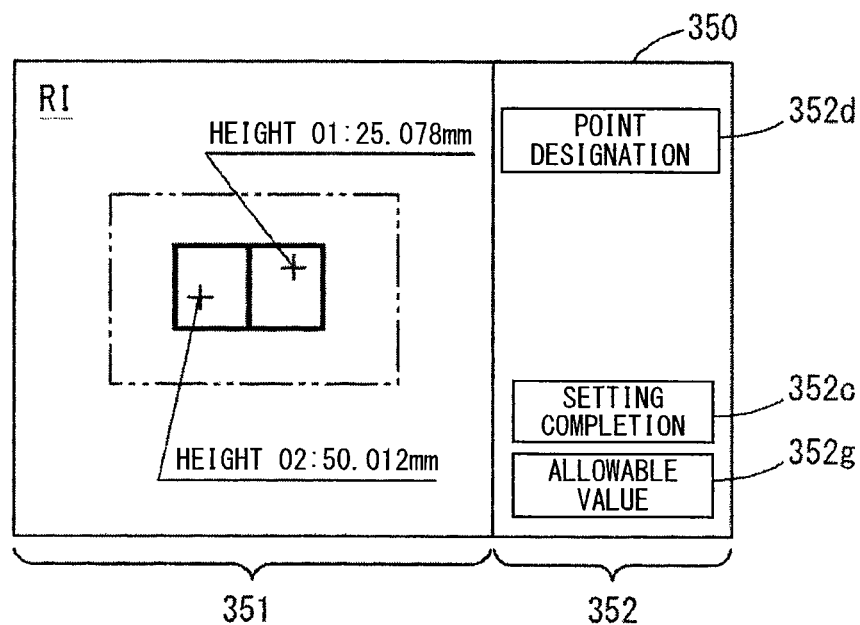
FIG. 28 is a diagram for explaining the operation example of the optical-scanning-height measuring device in the setting mode.

Thereafter, the measurement manager operates the setting completion button 352c. Consequently, the setting of the reference plane RF is completed. A display form of the setting screen 350 is switched as shown in FIG. 27. Specifically, in the image display region 351, the indicators indicating the one or plurality of reference points used for the setting of the reference plane RF are removed. In the button display region 352, an allowable value button 352g is displayed instead of the reference plane setting button 352e shown in FIG. 26.

The measurement manager operates the point designation button 352d to perform, for example, click operation on the image display region 351. Consequently, as indicated by "+" marks in FIG. 28, measurement points are designated. When a plurality of reference planes RF are set, one reference plane RF is selected out of the plurality of reference planes RF set as the reference plane RF serving as a reference for designated measurement points. When the designation and measurement processing explained above is performed concerning the designated measurement points and heights of portions of the measurement object S corresponding to the measurement points can be calculated, the heights of the portions of the measurement object S corresponding to the measurement points are displayed on the image display region 351. At this point, a color of the "+" marks may be changed to, for example, green to indicate that the heights of the portions of the measurement object S corresponding to the measurement points can be calculated.

On the other hand, when the designation and measurement processing explained above is performed concerning the designated measurement points and the heights of the portions of the measurement object S corresponding to the measurement points cannot be calculated, an error message such as "FAIL" may be displayed on the image display region 351. Further, the color of the "+" marks may be changed to, for example, red to indicate that the heights of the portions of the measurement object S corresponding to the measurement points cannot be calculated.

When a plurality of measurement points are designated, it may be possible to designate measurement route information. It may be possible to set information indicating that, for example, a measurement route is set in the order of the designation of the plurality of measurement points or a measurement route is set to be the shortest.

During the designation of the measurement points, by further operating the allowable value button 352g, the measurement manager can set a design value and a tolerance as allowable values for each of the measurement points. Lastly, the measurement manager operates the setting completion button 352c. Consequently, a series of information including the reference plane RF, the plurality of measurement points, and the allowable values are stored in the storing section 320 as registration information in association with one another. At this point, a specific file name is given to the registration information. Note that the file name may be capable of being set by the measurement manager.

As shown in FIGS. 25 to 28, indicators "+" indicating the positions of the reference points and the measurement points designated by the measurement manager are superimposed and displayed on the reference image RI. Consequently, the measurement manager can easily confirm the designated reference points and the designated measurement points by visually recognizing the indicators superimposed and displayed on the reference image RI of the measurement object S.

In the present invention, the order of the setting of reference points and measurement points in the setting mode is not limited to the example explained above. The setting of reference points and measurement points may be performed as explained below.

Figure 29:
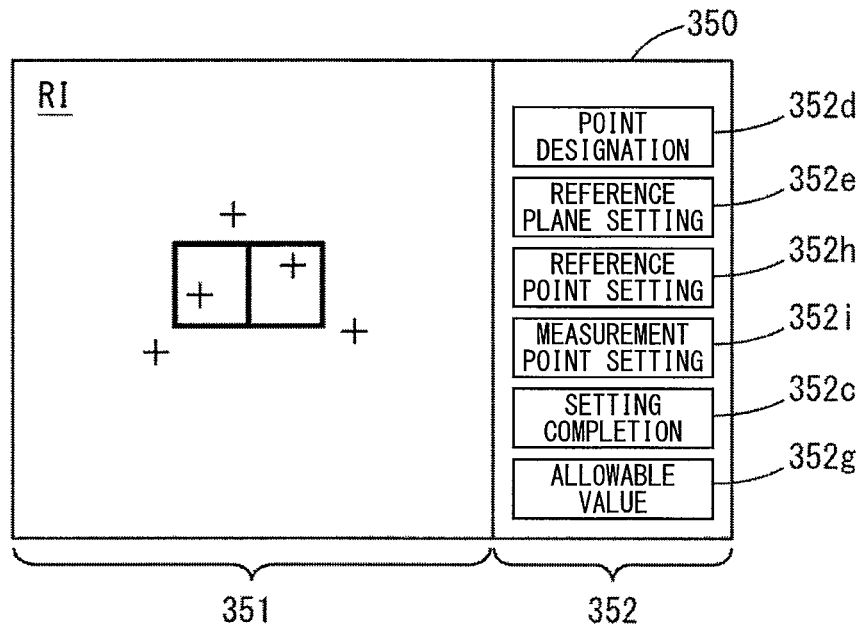
FIG. 29 is a diagram for explaining another operation example of the optical-scanning-height measuring device in the setting mode.
Figure 30:
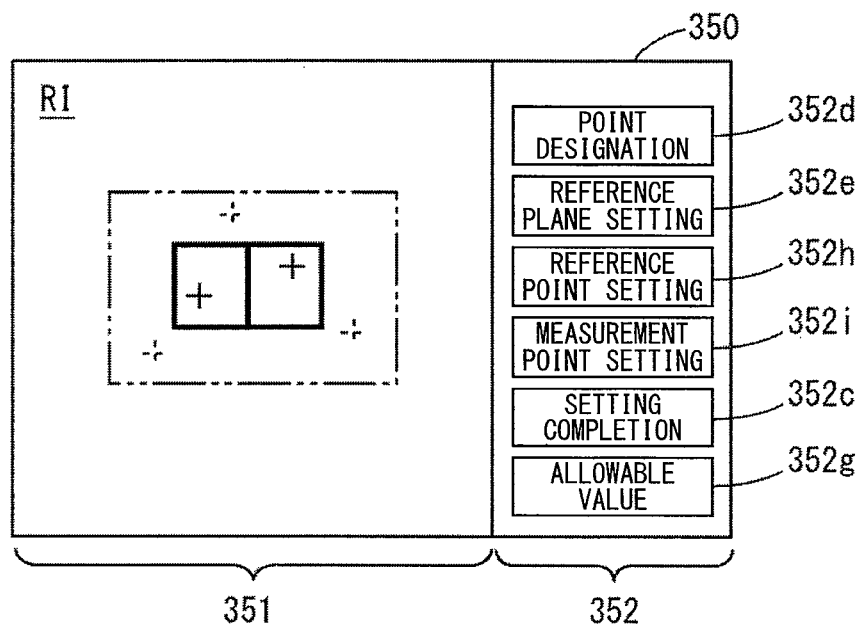
FIG. 30 is a diagram for explaining the other operation example of the optical-scanning-height measuring device in the setting mode.
Figure 31:
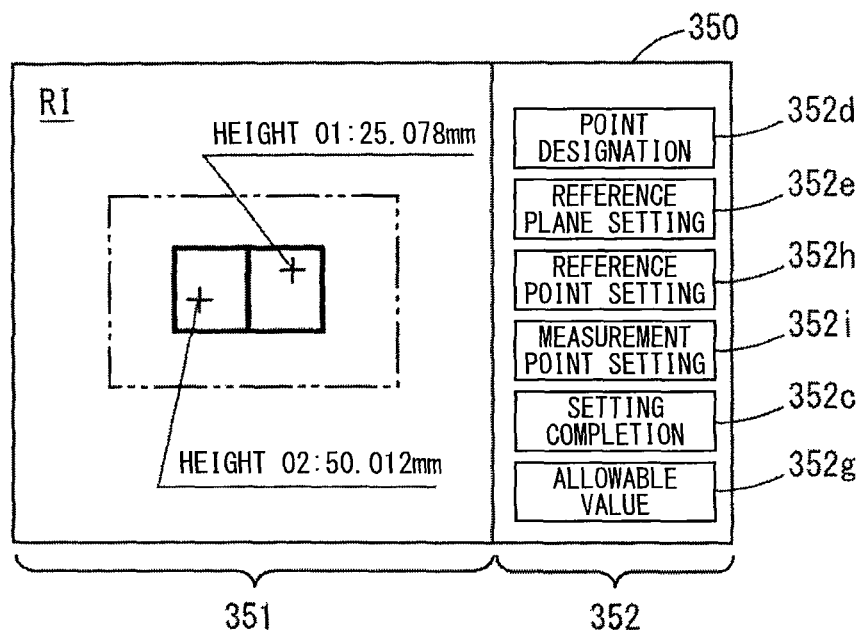
FIG. 31 is a diagram for explaining the other operation example of the optical-scanning-height measuring device in the setting mode.

FIGS. 29 to 31 are diagrams for explaining another operation example of the optical-scanning-height measuring device 400 in the setting mode. In this example, after the setting of the search region SR and the pattern image PI, as shown in FIG. 29, the setting completion button 352c, the point designation button 352d, the reference plane setting button 352e, the allowable value button 352g, a reference point setting button 352h, and a measurement point setting button 352i are displayed in the button display region 352.

In this state, the measurement manager operates the point designation button 352d to perform click operation or the like on the image display region 351. At this point, as indicated by the "+" marks in FIG. 25, the measurement manager designates a plurality of (in this example, five) points that can be reference points or measurement points.

Subsequently, the measurement manager operates the reference point setting button 352h or the measurement point setting button 352i for each of the designated points to thereby determine whether the point is used as a reference point or used as a measurement point. Further, after determining one or a plurality of points as reference points, the measurement manager operates the reference plane setting button 352e. Consequently, as shown in FIG. 30, one or a plurality of (in this example, three) reference points are displayed in the image display region 351 as indicated by dotted line "+" marks. A reference plane based on the one or plurality of reference points is displayed as indicated by an alternate long and two short dashes line. Further, one or a plurality of (in this example, two) measurement points are displayed as indicated by solid line "+" marks.

Thereafter, as shown in FIG. 31, heights of portions of the measurement objects S corresponding to the designated measurement points are displayed on the image display region 351. At this point, as in the example explained above, the measurement manager can set design values and tolerances as allowable values for each of the measurement points by operating the allowable value button 352g. Lastly, the measurement manager operates the setting completion button 352c.

Figure 32:
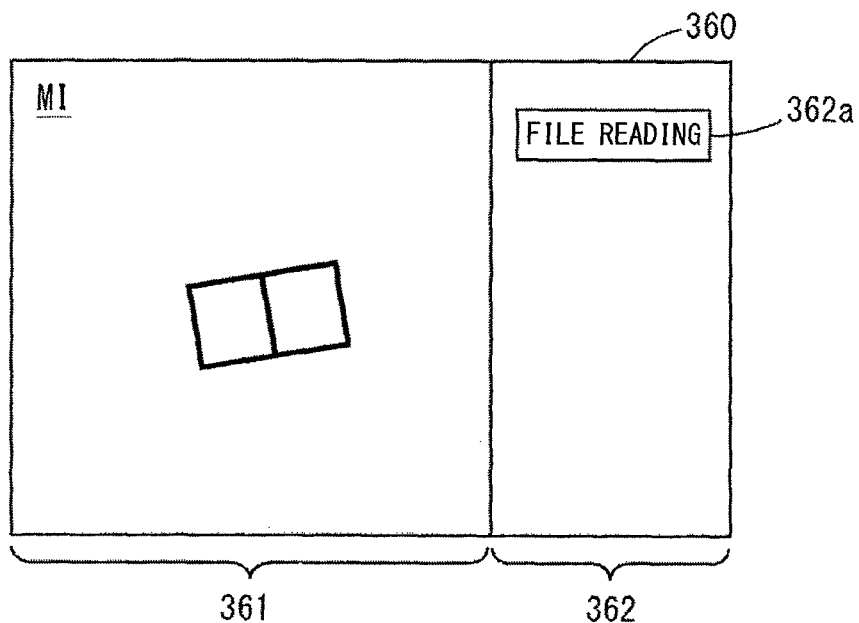
FIG. 32 is a diagram for explaining an operation example of the optical-scanning-height measuring device in a measurement mode.
Figure 33:
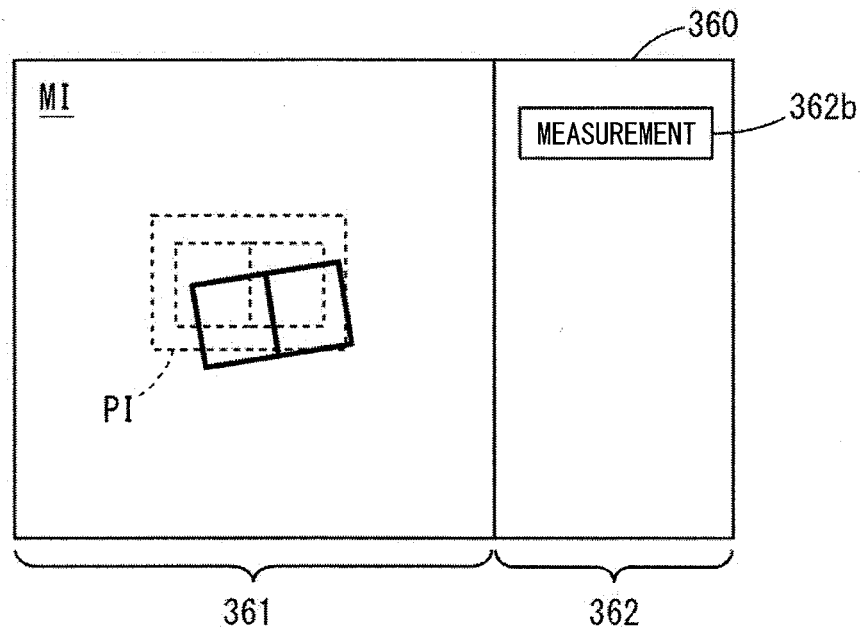
FIG. 33 is a diagram for explaining the operation example of the optical-scanning-height measuring device in the measurement mode.
Figure 34:
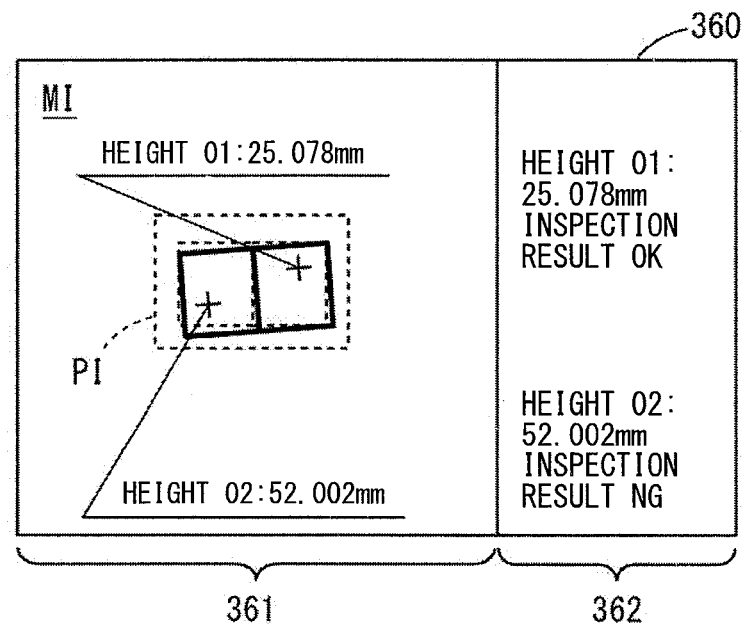
FIG. 34 is a diagram for explaining the operation example of the optical-scanning-height measuring device in the measurement mode.

FIGS. 32 to 34 are diagrams for explaining an operation example of the optical-scanning-height measuring device 400 in the measurement mode. The measurement operator positions the measurement object S set as a target of height measurement on the optical surface plate 111 and operates the measurement button 341b shown in FIG. 8 using the operation section 330 shown in FIG. 1. Consequently, the optical-scanning-height measuring device 400 starts the operation in the measurement mode. In this case, for example, as shown in FIG. 32, the measurement screen 360 is displayed on the display section 340 shown in FIG. 1. The measurement screen 360 includes an image display region 361 and a button display region 362. In the image display region 361, a currently captured image of the measurement object S is displayed as the measurement image MI.

At a start point in time of the measurement mode, a file reading button 362a is displayed in the button display region 362. The measurement operator selects a file name pointed by the measurement manager by operating the file reading button 362a. Consequently, registration information of height measurement corresponding to the measurement object S placed on the optical surface plate 111 is read.

When the registration information is read, as shown in FIG. 33, the pattern image PI corresponding to the read registration information is superimposed and displayed on the measurement image MI of the image display region 361 in a semitransparent state. A measurement button 362b is displayed in the button display region 362. In this case, the measurement operator can position the measurement object S in a more appropriate position on the optical surface plate 111 while referring to the pattern image PI.

Thereafter, the measurement operator operates the measurement button 362b after performing the more accurate positioning work for the measurement object S. Consequently, heights from a reference plane of a plurality of portions of the measurement object S corresponding to a plurality of measurement points of the read registration information are measured. When an allowable value is included in the read registration information, pass/fail determination of the portions corresponding to the measurement points is performed on the basis of the allowable value.

As a result, as shown in FIG. 34, the heights of the portions of the measurement object S respectively corresponding to the set measurement points are displayed on the image display region 361. The heights of the portions of the measurement object S respectively corresponding to the set measurement points are displayed on the button display region 362. A result of the pass/fail determination based on the allowable value is displayed as an inspection result.

(13) Effects

In the optical-scanning-height measuring device 400 according to this embodiment, in order to calculate a distance between the deflecting sections 271 and 272 and the measurement object S, the interference light of the measurement light returning from the measurement object S to the light guide section 240 and the reference light returning from the reflecting member 254c to the light guide section 240 is generated. In order to obtain interference light appropriate for the calculation of the distance, the optical path length of the reference light is adjusted.

The movable sections 252a and 252b supported by the supporting section 251 move on the linear guides 251g, whereby the optical path length of the reference light changes. At this point, the movable sections 252a and 252b move in the opposite directions each other. Consequently, even if the movable sections 252a and 252b intermittently repeat movement and stop, the position of the center of gravity of the optical-scanning-height measuring device 400 hardly changes. Therefore, the optical-scanning-height measuring device 400 does not unstably vibrate. It is unnecessary to increase the optical-scanning-height measuring device 400 in size and weight. It is possible to move the movable sections 252a and 252b at high speed. As a result, it is possible to quickly and highly accurately measure the height of the surface of the measurement object S while compactly configuring the optical-scanning-height measuring device 400.

In the reference section 250 explained above, the reflecting members 253, 254a, and 254b are provided between the optical fiber 243 and the reflecting member 254c used as the reference body. The reflecting members 253, 254a, and 254b reflect the reference light output from the optical fiber 243 to guide the reference light to the reflecting member 254c and reflect the reference light reflected by the reflecting member 254c to return the reference light to the optical fiber 243. With such a configuration, it is possible to compactly configure the optical-scanning-height measuring device 400 while securing a large optical path length of the reference light.

In the reference section 250 explained above, the reflecting members 254a and 254c are attached to the movable section 252a and the reflecting member 254b is attached to the movable section 252b. Consequently, during the movement of the movable sections 252a and 252b, the reflecting members 254a and 254c and the reflecting member 254b move close to or away from each other. In this case, the reflecting members 254a and 254c and the reflecting member 254b move close to each other, whereby the optical path length of the reference light decreases. The reflecting members 254a and 254c and the reflecting member 254b move away from each other, whereby the optical path length of the reference light increases. Therefore, an adjustable range of the optical path length of the reference light is expanded. It is possible to more quickly change the optical path length of the reference light.

Figure 35:
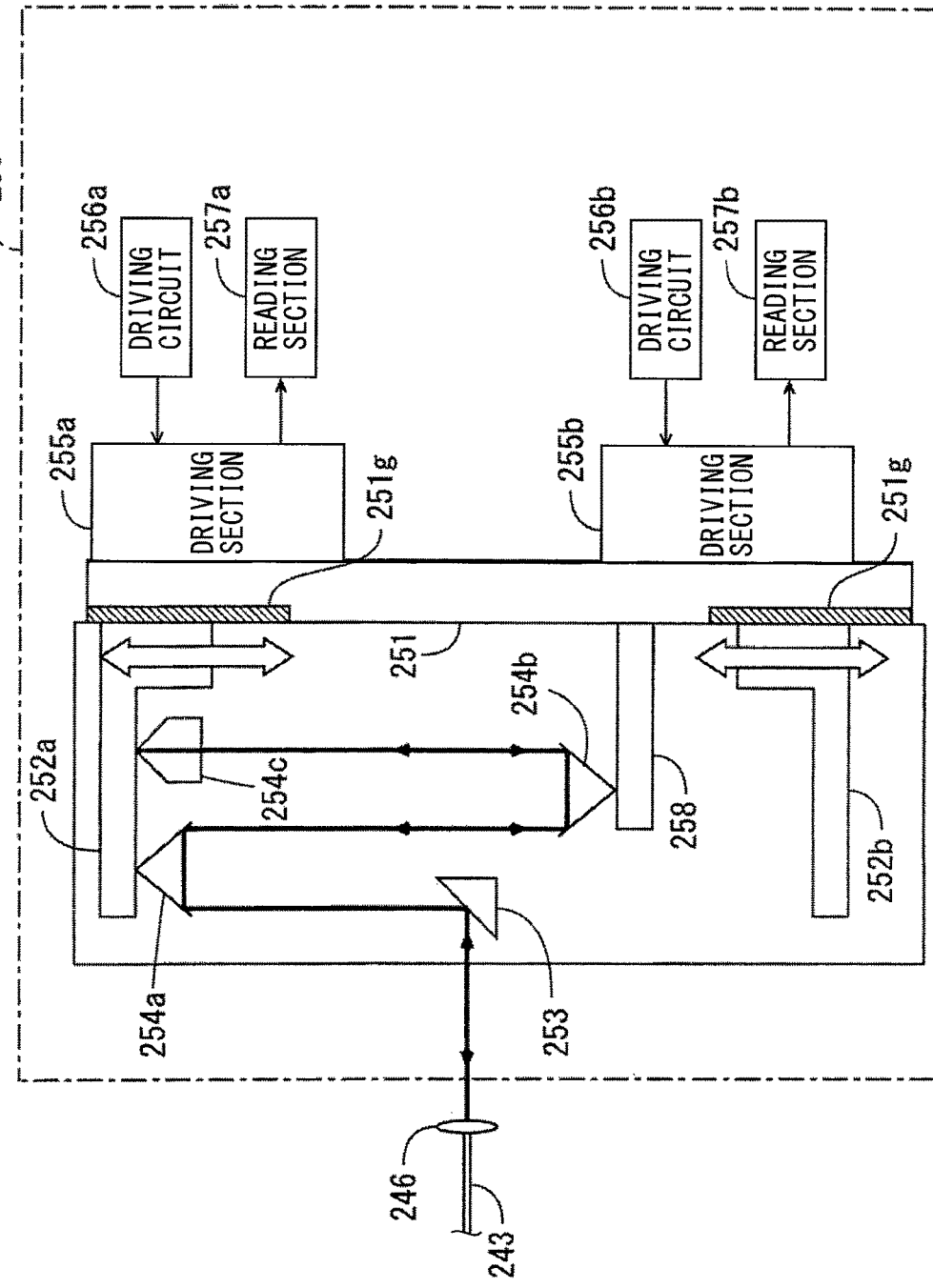
FIG. 35 is a schematic diagram showing another configuration example of the reference section.

(14) Other Embodiments (a) In the embodiment explained above, the reflecting members 254a and 254c and the reflecting member 254b are respectively attached to the movable section 252a and the movable section 252b that move in the opposite directions each other. However, the present invention is not limited to this. Any one of the reflecting members 254a, 254b, and 254c may be attached to only one of the movable sections 252a and 252b. FIG. 35 is a schematic diagram showing another configuration example of the reference section 250. Concerning the reference section 250 shown in FIG. 35, differences from the reference section 250 shown in FIG. 5 are explained.

As shown in FIG. 35, in the reference section 250 in this example, the reflecting members 254b among the reflecting members 254a, 254b, and 254c is fixed to the supporting section 251 by a fixed section 258. Therefore, the reflecting member 254b does not move with respect to the supporting section 251. The reflecting members 254a and 254c are attached to the movable section 252a as in the example shown in FIG. 5. The weight of the movable section 252b is set to be equal to a total of the weight of the movable section 252a and the weight of the reflecting members 254a and 254c or to be in a fixed range from the total.

In the configuration explained above, as in the embodiment, the driving circuits 256a and 256b move the movable sections 252a and 252b with respect to the supporting section 251 in the opposite directions each other when the optical path length of the reference light is adjusted. In this case, the movable section 252b functions as a balancing section with respect to the movable section 252a and the reflecting members 254a and 254c. Therefore, even if the movable sections 252a and 252b intermittently repeat movement and stop, the position of the center of gravity of the optical-scanning-height measuring device 400 hardly changes. Therefore, the position of the center of gravity of the optical-scanning-height measuring device 400 is stabilized during the movement of the movable sections 252a and 252b.

(b) In the embodiment explained above, the four reflecting members 253, 254a, 254b, and 254c are used in order to form the optical path of the reference light in the reference section 250. However, the present invention is not limited to this. In the reference section 250, only one reflecting member functioning as the reference body may be provided or two, three, or five or more reflecting members may be provided. Note that, when only one reflecting member functioning as the reference body is provided in the reference section 250, the reflecting member is provided on one movable member that moves in a direction parallel to the optical axis of the lens 246. Another movable member that moves in the opposite direction of the moving direction of the one movable member is provided in the reference section 250. Consequently, it is possible to obtain the same effects as the effects in the embodiment explained above.

(c) In the embodiment explained above, the reflecting member 254c functioning as the reference body is provided in the movable section 252a in the reference section 250. However, the reflecting member 254c may be fixedly attached to the supporting section 251. In this case as well, since the other reflecting members 254a and 254b are attached to the movable sections 252a and 252b, it is possible to change the optical path length of the reference light.

Figure 36:
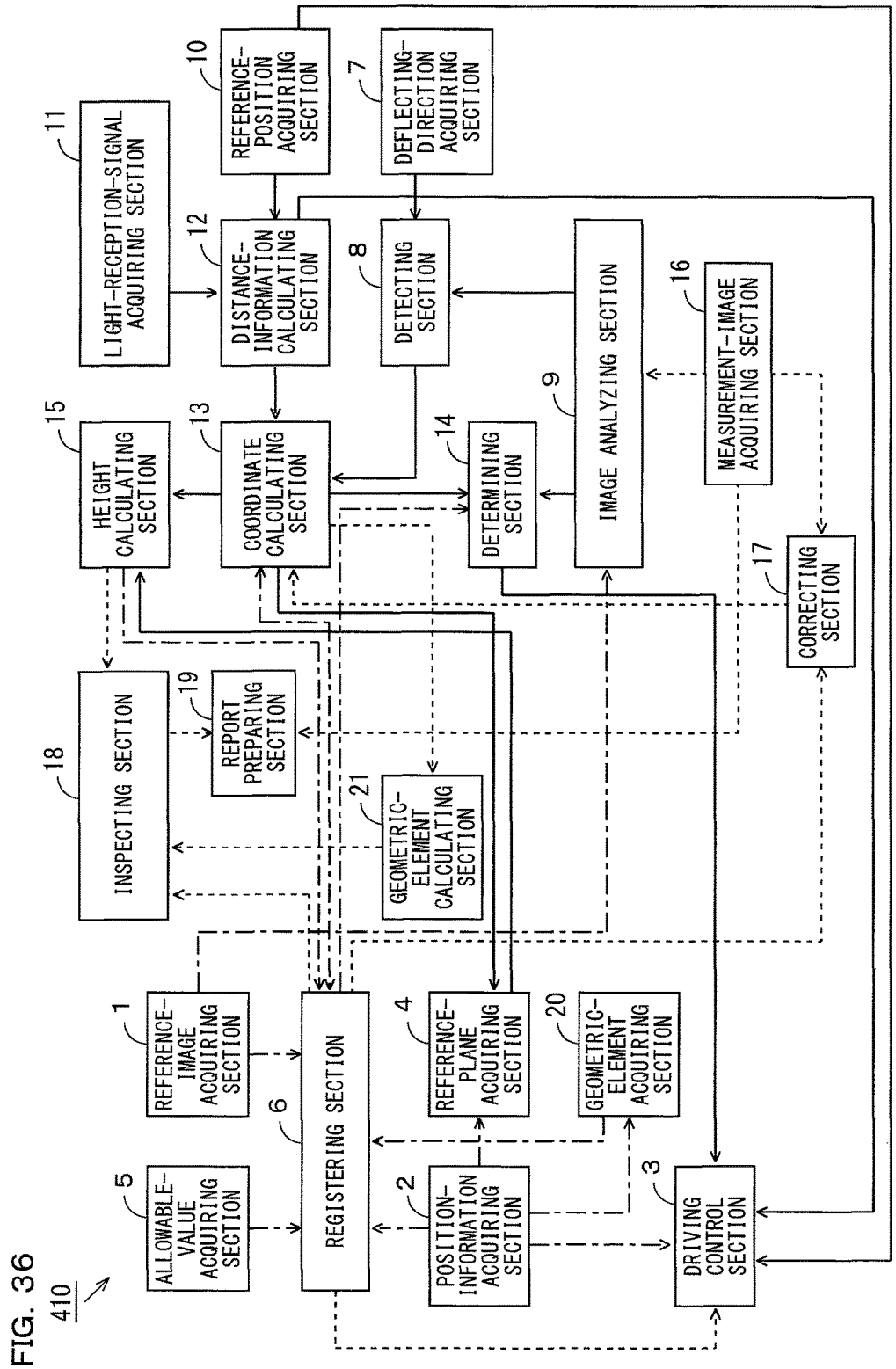
FIG. 36 is a block diagram showing another configuration example of the control system of the optical-scanning-height measuring device.

(d) FIG. 36 is a block diagram showing another configuration example of the control system 410 of the optical-scanning-height measuring device 400. Concerning the control system 410 shown in FIG. 36, differences from the control system 410 shown in FIG. 10 are explained. As shown in FIG. 36, in this example, the control system 410 further includes a geometric-element acquiring section 20 and a geometric-element calculating section 21.

In the setting mode, the geometric-element acquiring section 20 receives designation of geometric elements concerning a position of a measurement point acquired by the position-information acquiring section 2. The geometric elements concerning the position of the measurement point are various elements that can be calculated on the basis of a coordinate of a portion of the measurement object S corresponding to the measurement point. The geometric elements include, for example, flatness of a desired surface of the measurement object S and distances and angles of a plurality of portions of the measurement object S. Allowable values corresponding to the designated geometric elements may be further input to the allowable-value acquiring section 5.

The registering section 6 registers the geometric elements received by the geometric-element acquiring section in association with the measurement point. When the allowable values corresponding to the geometric elements are input to the allowable-value acquiring section 5, the registering section 6 registers the allowable values received by the allowable-value acquiring section 5 in association with the geometric elements. The coordinate calculating section 13 further calculates a coordinate related to the geometric elements registered in the registering section 6. The geometric-element calculating section 21 calculates, on the basis of the coordinate related to the geometric elements calculated by the coordinate calculating section 13, values of the geometric elements registered in the registering section 6.

In the measurement mode, the correcting section 17 further sets, in the measurement image data, the geometric elements corresponding to the registration information registered by the registering section 6. The coordinate calculating section 13 further calculates a coordinate related to the geometric elements set by the correcting section 17. The geometric-element calculating section 21 calculates, on the basis of the coordinate related to the geometric elements calculated by the coordinate calculating section 13, geometric elements set by the correcting section 17.

With this configuration, since the measurement manager designates the geometric elements in the setting mode, in the measurement mode, even when the measurement operator is not skilled, it is possible to uniformly acquire a calculation result of the geometric elements of the corresponding portion of the measurement object S. Consequently, it is possible to accurately and easily measure various geometric elements including flatness and an assembling dimension of the measurement object S.

When the allowable values corresponding to the geometric elements are registered in the registering section 6, the inspecting section 18 further inspects the measurement object S on the basis of the geometric elements calculated by the geometric-element calculating section 21 and the allowable values registered in the registering section 6. Specifically, when the calculated geometric elements are within ranges of tolerances based on design values, the inspecting section 18 determines that the measurement object S is a non-defective product. On the other hand, when the calculated geometric elements are outside the ranges of the tolerances based on the design values, the inspecting section 18 determines that the measurement object S is a defective product.

The report preparing section 19 prepares the report 420 shown in FIG. 11 on the basis of the inspection result of the inspecting section 18 and the reference image acquired by the measurement-image acquiring section 16. In this case, inspection results of various geometric elements other than height are described in the report 420. In the example shown in FIG. 11, as the geometric elements, in addition to the height of the portion of the measurement object S, flatness, a difference in level, and an angle are described. Consequently, the measurement operator can inspect an assembling dimension of the measurement object S and can easily report a result of the inspection to the measurement manager or the other users using the report 420.

Figure 37:
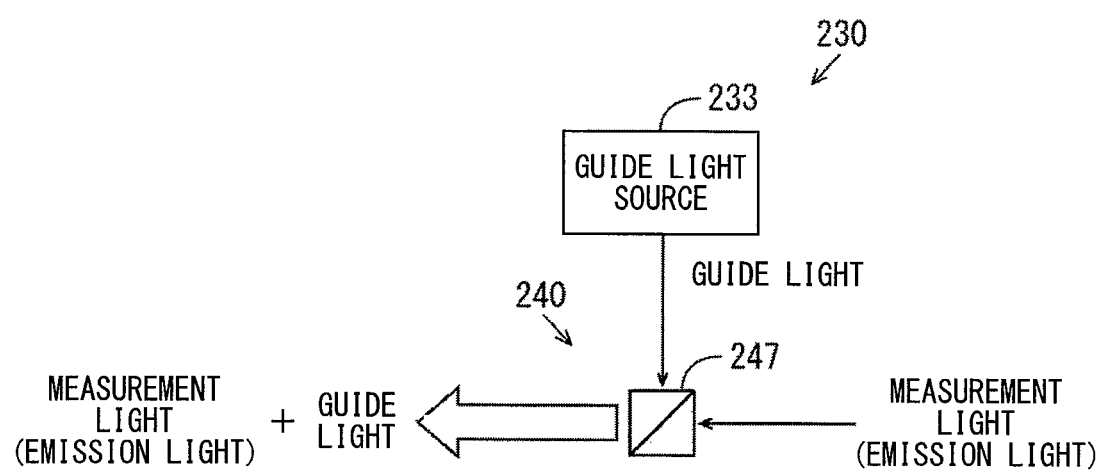
FIG. 37 is a schematic diagram showing another configuration example of the optical section of the optical-scanning-height measuring device.

(e) FIG. 37 is a schematic diagram showing another configuration example of the optical section 230 of the optical-scanning-height measuring device 400. As shown in FIG. 37, the optical section 230 further includes a guide light source 233 that emits, for example, light in a visible region. The light emitted by the guide light source 233 is referred to as guide light. The light guide section 240 further includes a half mirror 247.

The half mirror 247 is disposed in a desired position on an optical path of measurement light output from the port 245d of the fiber coupler 245 shown in FIG. 3. The half mirror 247 superimposes the guide light emitted from the guide light source 233 and the measurement light output from the port 245d one on top of the other. Consequently, the guide light is scanned by the scanning section 270 shown in FIG. 3 and is irradiated on the measurement object S in a state in which the guide light is superimposed on the measurement light.

With this configuration, the user can easily recognize an irradiation position of light on the measurement object S from the scanning section 270 by visually recognizing an irradiation position of the guide light on the measurement object S. The imaging section 220 shown in FIG. 3 can clearly image the guide light on the measurement object S together with the measurement light. Consequently, the image analyzing section 9 shown in FIG. 10 can easily detect, as a plane coordinate indicating an irradiation position of the measurement light, a plane coordinate indicating an irradiation position of the guide light on a reference image or a measurement image. Note that, typically, the measurement light is infrared light having low coherency. Typically, the imaging section 220 cannot image the infrared light. Therefore, in this case, the imaging section 220 image the irradiation position of the guide light as the irradiation position of the measurement light.

In this example, the guide light source 233 and the half mirror 247 are provided such that the guide light overlaps the measurement light output from the port 245d of the fiber coupler 245. However, the present invention is not limited to this. The guide light source 233 and the half mirror 247 may be provided such that the guide light overlaps emission light output from the light emitting section 231 shown in FIG. 3. In this case, the half mirror 247 is disposed in a desired position on an optical path of the emission light between the light emitting section 231 and the port 245a of the fiber coupler 245.

In this example, the guide light and the measurement light are superimposed one on top of the other by the half mirror 247. However, the present invention is not limited to this. Typically, the measurement light is infrared light having low coherency. The guide light includes light in a visible region. Therefore, for example, the guide light and the measurement light may be superimposed one on top of the other by a wavelength selective mirror such as a dichroic mirror that shows high reflectance to light having a wavelength smaller than a cutoff wavelength and shows high transmittance to light having a wavelength larger than the cutoff wavelength. The guide light and the measurement light may be superimposed one on top of the other by, for example, a fiber coupler and an optical fiber. In this case, the fiber coupler has a so-called 2×1 type configuration.

(f) The height calculating section 15 may calculate height of a portion of the measurement object S based on an origin in a peculiar three-dimensional coordinate system defined in the optical-scanning-height measuring device 400. In this case, the user can acquire the absolute value of the height of the portion of the measurement object S in the peculiar three-dimensional coordinate system. The height calculating section 15 may be capable of selectively operating in a relative value calculation mode for calculating the relative value of height based on a reference plane and an absolute value calculation mode for calculating the absolute value of height in a peculiar three-dimensional coordinate system. In the absolute value calculation mode, since the reference plane is unnecessary, the reference point may be not designated.

(g) In the setting mode, when height of the portion of the measurement object S corresponding to the measurement point cannot be calculated, the height calculating section 15 may cause the display section 340 to display an error message such as "FAIL". In this case, by visually recognizing the display section 340, the measurement manager can recognize that height of the portion of the measurement object S corresponding to the measurement point cannot be calculated. Consequently, the measurement manager can change the disposition of the measurement object S or the optical-scanning-height measuring device 400 or change the position of a measurement point to be designated such that height of the portion of the measurement object S can be calculated.

(h) The optical-scanning-height measuring device 400 may be capable of inserting a drawing and a comment into the reference image acquired in the setting mode or the measurement image acquired in the measurement mode. Consequently, it is possible to record a measurement state of the measurement object S more in detail. The drawing and the comment inserted into the reference image may be registered as the registration information.

For example, a frame line indicating the search region set in the setting mode may be drawn in the reference image. In this case, in the measurement mode, the frame line is displayed on the measurement image. Consequently, in the measurement mode, it is easy for the measurement operator to place the measurement object S on the optical surface plate 111 such that the measurement object S fits inside the frame line displayed on the measurement image. As a result, it is possible to efficiently correct deviation of the measurement image data with respect to the reference image data.

(i) The reference-image acquiring section 1 may cause the display section 340 to display the acquired reference image in a bird's eye view fashion by performing image processing of the reference image. Similarly, the measurement-image acquiring section 16 may cause the display section 340 to display the acquired measurement image in a bird's eye view fashion by performing image processing of the measurement image.

(j) In the embodiment explained above, the reference-image acquiring section 1 and the measurement-image acquiring section 16 acquire the captured image of the measurement object S by the imaging section 220 respectively as the reference image and the measurement image. However, the present invention is not limited to this. The reference-image acquiring section 1 and the measurement-image acquiring section 16 may acquire a CAD (Computer Aided Design) image of the measurement object S prepared in advance respectively as the reference image and the measurement image.

Alternatively, when the measurement light is irradiated on a plurality of portions of the measurement object S, the height calculating section 15 is capable of calculating heights of the plurality of portions of the measurement object S. Therefore, the reference-image acquiring section 1 and the measurement-image acquiring section 16 may acquire a distance image of the measurement object S respectively as the reference image and the measurement image on the basis of the heights of the plurality of portions of the measurement object S.

When the CAD image or the distance image is used as the reference image, the measurement manager can accurately designate a desired reference point and a desired measurement point on the CAD image or the distance image while recognizing a three-dimensional shape of the measurement object S. When the distance image is used as the reference image and the measurement image, the distance image may be quickly generated by reducing resolution.

(k) In the embodiment explained above, the measurement operator designates the file of the registration information during the start of the measurement mode. However, the present invention is not limited to this. For example, an ID (identification) tag corresponding to the file of the registration information may be stuck to the measurement object S. In this case, the ID tag is imaged by the imaging section 220 together with the measurement object S during the start of the measurement mode, whereby the file of the registration information corresponding to the tag is automatically designated. With this configuration, the measurement operator does not need to designate the file of the registration information during the start of the measurement mode. Therefore, the processing in step S203 in FIG. 15 is omitted.

(l) In the embodiment explained above, the height of the measurement object S is calculated by the spectral interference system. However, the present invention is not limited to this. The height of the measurement object S may be calculated by another system such as a white interference system, a confocal system, a triangulation system, or a TOF (time of flight) system.

(m) In the embodiment explained above, the light guide section 240 includes the optical fibers 241 to 244 and the fiber coupler 245. However, the present invention is not limited to this. The light guide section 240 may include a half mirror instead of the optical fibers 241 to 244 and the fiber coupler 245.

(15) A Correspondence Relation Between the Constituent Elements of the Claims and the Sections of the Embodiments An example of correspondence between the constituent elements of the claims and the sections of the embodiments is explained below. However, the present invention is not limited to the example explained below.

In the embodiments explained above, the measurement object S is an example of the measurement object, the position-information acquiring section 2 is an example of the position-information acquiring section, the light emitting section 231 is an example of the light emitting section, the light guide section 240 is an example of the dividing section and the interference-light generating section, the deflecting sections 271 and 272 are examples of the deflecting section, the driving control section 3 is an example of the driving control section, the detecting section 8 is an example of the detecting section, one of the two linear guides 251g is an example of the first movement axis, and the other of the two linear guides 251g is an example of the second movement axis.

The reflecting member 254c is an example of the reference body, the movable section 252a is an example of the movable section, the supporting section 251 is an example of the supporting section, the reading section 257a is an example of the movable-section-position detecting section, the light receiving section 232d is an example of the light receiving section, the distance-information calculating section 12 is an example of the distance-information calculating section, the height calculating section 15 is an example of the height calculating section, the movable section 252b is an example of the balancing section, the driving sections 255a and 255b and the driving circuits 256a and 256b are examples of the reference driving section, and the optical-scanning-height measuring device 400 is an example of the optical-scanning-height measuring device.

The reflecting members 253, 254a, and 254b are examples of the one or plurality of reflecting members, the focusing section 260 is an example of the focusing section, the movable lens 263 is an example of the lens, the movable section 262, the fixed section 261, the driving section 264, and the driving circuit 265 are examples of the lens moving section, and the control board 210 is an example of the lens control section.

As the constituent elements of the claims, other various elements having the configurations or the functions described in the claims can also be used.

The present invention can be effectively used for various optical-scanning-height measuring devices.

What is claimed is:

1. An optical-scanning-height measuring device comprising:
   a position-information receiver configured to receive designation of a measurement point;
   a light emitter configured to emit temporally low-coherent light;
   a light splitter configured to divide the light emitted from the light emitter and output a part of the divided light as measurement light and output another part of the divided light as reference light;
   a light deflector configured to deflect the measurement light output from the light splitter and irradiate the measurement light on a measurement object;
   a driving controller configured to control the light deflector to irradiate light on a portion of the measurement object corresponding to the measurement point received by the position-information receiver;
   a deflection detector configured to detect a deflecting direction of the light deflector or an irradiation position of the measurement light deflected by the light deflector;
   a reference body configured to reflect the reference light output from the light splitter to return to the light splitter;
   a movable stage configured to move the reference body along a first movement axis to change an optical path length of the reference light leading from the light splitter to the reference body;
   a supporting member configured to movably support the movable stage on the first movement axis;
   a position detector configured to detect a relative position of the movable stage with respect to the supporting member;
   an interference-light generating section configured to generate interference light of the measurement light irradiated on the measurement object by the light deflector to return to the light splitter from the measurement object and the reference light reflected by the reference body to return to the light splitter;
   a light receiver configured to receive the generated interference light and generate a light reception signal indicating a received light amount of the interference light;
   a distance-information calculator configured to calculate a distance between the light splitter and the measurement object on the basis of the position of the movable stage detected by the position detector and the received light amount of the interference light in the light reception signal output by the light receiver;
   a height calculator configured to calculate height of a portion of the measurement object corresponding to the designated measurement point on the basis of the deflecting direction of the light deflector and the irradiation position of the measurement light deflected by the light deflector detected by the deflection detector and the distance calculated by the distance-information calculator;
   a balancing body movably supported on a second movement axis extending substantially in parallel to the first movement axis with respect to the supporting member; and
   a reference driver configured to move the movable stage and the balancing body with respect to the supporting member in opposite directions each other during the movement of the movable stage.

2. The optical-scanning-height measuring device according to claim 1, further comprising one or a plurality of reflecting members configured to reflect the reference light output from the light splitter to guide the reference light to the reference body and reflect the reference light reflected by the reference body to return the reference light to the light splitter, wherein
   a part of the reference body and the one or plurality of reflecting members is attached to the movable stage.

3. The optical-scanning-height measuring device according to claim 2, wherein
   at least a remaining part of the reference body and the one or plurality of reflecting members is attached to the balancing body,
   the position detector further detects a relative position of the balancing body with respect to the supporting member, and
   the distance-information calculator calculates a distance between the light deflector and the measurement object on the basis of the position of the movable stage and the position of the balancing body detected by the position detector and the light reception signal output by the light receiver.

4. The optical-scanning-height measuring device according to claim 3, wherein a total of weight of a part of the reference body and the one or plurality of reflecting members and weight of the movable stage is set to be in a fixed range from a total of weight of at least the remaining part of the reference body and the one or plurality of reflecting members and weight of the balancing body.

5. The optical-scanning-height measuring device according to claim 1, wherein the reference body is a corner cube reflector.

6. The optical-scanning-height measuring device according to claim 1, wherein
   the distance-information calculator calculates a difference between an optical path length of the measurement light irradiated on the measurement object by the light deflector and returning from the measurement object to the light splitter and an optical path length of the reference light reflected by the reference body to return to the light splitter and calculates a distance between the light deflector and the measurement object on the basis of a result of the calculation, and
   the driving controller controls the reference driver such that an optical path length of the reference light leading from the light splitter to the reference body is maintained when the difference calculated by the distance-information calculator is equal to or smaller than a threshold decided in advance and controls the reference driver such that the optical path length of the reference light leading from the light splitter to the reference body changes when the difference calculated by the distance-information calculator is larger than the threshold decided in advance.

7. The optical-scanning-height measuring device according to claim 1, further comprising a focusing section, wherein
   the focusing section includes:
   a lens disposed on an optical path of the measurement light from the light splitter to the light deflector;
   a lens moving section configured to move the lens on the optical path of the measurement light to thereby adjust a position of a focus of the measurement light irradiated on the measurement object; and a lens control section configured to control the lens moving section on the basis of the distance calculated by the distance-information calculator to focus the measurement light on a surface of the measurement object.

* * * * *